(12) United States Patent
Kadkhodayan et al.

(10) Patent No.: US 7,662,936 B2
(45) Date of Patent: Feb. 16, 2010

(54) MASS SPECTROMETRY OF ANTIBODY CONJUGATES

(75) Inventors: Miryam Kadkhodayan, Belmont, CA (US); Emily Mann, Richland, MI (US)

(73) Assignee: Genentech, Inc., South San Francisco, CA (US)

( * ) Notice: Subject to any disclaimer, the term of this patent is extended or adjusted under 35 U.S.C. 154(b) by 407 days.

(21) Appl. No.: 11/101,018

(22) Filed: Apr. 6, 2005

(65) Prior Publication Data

US 2005/0232929 A1   Oct. 20, 2005

Related U.S. Application Data

(60) Provisional application No. 60/560,530, filed on Apr. 7, 2004, provisional application No. 60/654,020, filed on Feb. 17, 2005.

(51) Int. Cl.
  *A61K 39/395* (2006.01)
  *C07K 16/00* (2006.01)
  *C07K 1/22* (2006.01)
(52) U.S. Cl. ............... 530/413; 424/9.2; 424/178.1; 424/181.1; 424/183.1; 436/173; 436/825; 530/391.7; 530/391.9
(58) Field of Classification Search ............... 424/9.2, 424/178.1, 181.1, 183.1; 436/173; 530/391.7, 530/391.9
See application file for complete search history.

(56) References Cited

U.S. PATENT DOCUMENTS

| 6,020,208 A | 2/2000 | Hutchens et al. | 436/174 |
| 7,329,353 B2 * | 2/2008 | Dillon et al. | 210/635 |
| 2002/0197694 A1 * | 12/2002 | Shao | 435/188.5 |
| 2003/0027216 A1 | 2/2003 | Kiernan et al. | 435/7.1 |

FOREIGN PATENT DOCUMENTS

| WO | WO 03/046571 | 6/2003 |
| WO | WO 03/046572 | 6/2003 |

OTHER PUBLICATIONS

Abdel-Hamid et al., "Liquid chromatographic-mass spectrometric determination of celecoxib in plasma using single-ion monitoring and its use in clinical pharmacokinetics" *J. of Chrom.* B 753:401-408 (2001).
Alley, S.C. et al., "Controlling the location of drug attachment in antibody-drug conjugates, Abstract No. 627, American Association for Cancer Research, 2004 Annual Meeting, Mar. 27-31, 2004 Proceedings of the AACR" 45:52 (2004).
Beaudry, F. et al., "In Vivo pharmacokinetic screening in cassette dosing experiments: the use of on-line Prospekt$^R$ liquid chromatography/atmospheric pressure chemical ionization tandem mass spectrometry technology in drug discovery" *Rapid Commun. Mass Spectrom.* 12:1216-1222 (1998).

Bier, Mark E., "Analysis of proteins by mass spectrometry" *Modern Protein Chemistry*, Howard and Brown, CRC Press, Chapter 4, pp. 71-88 (2002).
DiJoseph et al., "Antibody-targeted chemotherapy with CMC-544: a CD22-targeted immunoconjugate of calicheamicin for the treatment of B-lymphoid malignancies" *Blood* 103:1807-1814 (2004).
Doronina et al., "Development of potent monoclonal antibody auristatin conjugates for cancer therapy" *Nature Biotechnology* 21:778-784 (2003).
Francisco et al., "cAC10-vcMMAE, an anti-CD30 monomethyl auristatin E conjugate with potent and selective antitumor activity" *Blood* 102:1458-1465 (2003).
Hamblett, K. J. et al., "Effect of drug loading on the pharmacology, pharmacokinetics and toxicity of an anti-CD30 antibody-drug conjugate, Abstract No. 624, American Association for Cancer Research; 2004 Annual Meeting, Mar. 27-31, 2004. Proceedings of the AACR" 45 144 (2004).
Hamblett, K. J. et al., "Effects of drug loading on the antitumor activity of a monoclonal antibody drug conjugate" *Clin. Cancer Res.* 10:7063-7070 (2004).
Kadkhodayan, M. and Mann, E., "New strategies in characterization and quantitation of antibody-targeted drug conjugates in plasma using LC/LC/MS, 51st Conference on Mass Spectrometry and Allied Topics, American Society for Mass Spectrometry, Montreal, Quebec, Jun. 8-12, 2003" (2003).
Kirchner et al., "Clinical pharmacokinetics of everolimus" *Clin. Pharmacokinetics* 43(2) :83-95 (2004).
Marques et al., "Enantioselective assay of nisoldipine in human plasma by chiral high-performance liquid chromatography combined with gas chromatographic-mass spectrometry: applications to pharmacokinetics" *J. of Chrom.* 762:87-95 (2001).
Martin et al., "Antibody-directed enzyme prodrug therapy: pharmacokinetics and plasma levels of prodrug and drug in a phase I clinical trial" *Cancer Chemother. Pharmacol.* 40:189-201 (1997).
Murray, S. et al., "Identification of human serum interferants in the recombinant P-selectin glycoprotein ligand-1 clinical ELISA using MALDI MS and RP-HPLC" *J. Imm. Methods* 255:41-56 (2001).
Royer et al., "Paclitaxel metabolites in human plasma and urine: identification of 6α-hydroxytaxol, 7-epitaxol and taxol hydrolysis products using liquid chromatography/atmospheric-pressure chemical ionization mass spectrometry" *Rapid Comm. in Mass Spec.* 9:495-502 (1995).

(Continued)

Primary Examiner—David A Saunders
(74) Attorney, Agent, or Firm—Alex Andrus

(57) ABSTRACT

Methods to detect, screen, and quantitate biological samples after administration of antibody conjugates, antibody-drug conjugates of Formula I, antibodies, and fragments and metabolites thereof, by affinity separation, chromatography, and mass spectrometry are disclosed.

$$Ab\text{-}(L\text{-}D)_p \qquad\qquad I$$

wherein
Ab is an antibody;
D is a drug moiety;
L is a linker covalently attached to Ab, and covalently attached to D; and
p is 1, 2, 3, 4, 5, 6, 7, or 8.

3 Claims, 24 Drawing Sheets

OTHER PUBLICATIONS

Sanderson, R. J. et al., "In Vivo drug-linker stability of an anti-CD30 dipeptide-linked auristatin immunoconjugate" *Clin. Cancer Res.* 11:843-852 (2005).

Senter, P. et al., "Immunoconjugates comprised of drugs with impaired cellular permeability: a new approach to targeted therapy, Abstract No. 623, presented on Mar. 28, 2004, Proceedings of the American Association for Cancer Research" 45: 144 (2004).

Simpson, H. et al., "High throughput liquid chromatography/mass spectrometry bioanalysis using 96-well disk solid phase extraction plate for the sample preparation" *Rapid Commun. Mass Spectrom.* 12:75-82 (1998).

Souppart et al., "Development and validation of a high-performance liquid chromatography-mass spectrometry assay for the determination of artemether and its metabolite dihydroartemisinin in human plasma" *J. of Chrom.* B 774:195-203 (2002).

Wong et al., "Liquid chromatography-mass spectrometry assay of a thiadiazole derivative in mice: application to pharmacokinetic studies" *J. of Chrom.* 765:55-62 (2001).

Yao et al., "Quantitation of itraconazole in rat heparinized plasma by liquid chromatography-mass spectrometry" *J. Chrom.* B 752:9-16 (2001).

Yao et al., "Sensitive liquid chromatographic-mass spectrometric assay for the simultaneous quantitation of nefazodone and its metabolites hydroxynefazodone m-chlorophenylpiperazine and triazole-dione in human plasma using single-ion monitoring" *J. of Chrom.* B 718:77-85 (1998).

Kruppa et al., "Multiple ion isolation applications in FY-ICR MS: exact-mass MSn internal calibration and purification/interrogation of protein-drug complexes" *Anal Chem.* 74(15):3877-3886 (Aug. 1, 2002).

Mao et al., "EphB2 as a Therapeutic Antibody Drug Target for the Treatment of Colorectal Cancer" *Cancer Research* 64:781-788 (2004).

Siegel et al., "Calicheamicin derivatives conjugated to monoclonal antibodies: determination of loading values and distributions by infrared and UV matrix-assisted laser desorption/ionization mass spectrometry and electrospray ionization mass spectrometry" *Anal Chem.* 69(14):2716-2726 (Jul. 15, 1997).

Siegel et al., "Determination of loading values and distributions for drugs conjugated to proteins and antibodies by MALDI-MS and ESI-MS" *Methods Mol Biol.* 61:211-226 (1996).

Xie et al, "Pharmacokinetics and biodistribution of the antitumor immunoconjugate, cantuzumab mertansine (huC242-DM1), and its two components in mice" *J Pharmacol Exp Ther.* 308(3):1073-1082 (Mar. 2004).

Kadkhodayan et al., "A novel approach to characterization of Trastuzumab-DM1 conjugates using LC-MS for confirmation of statistically calculated distributions, 51st Conference on Mass Spectrometry and Allied Topics, American Society for Mass Spectrometry, Montreal, Quebec, Jun. 8-12, 2003" (2003).

Kadkhodayan, M. and Mann, E., "Rapid antibody characterization and Quantitation using automated chip-based nanoelectrospray/MS, 52nd Conference on Mass Spectrometry and Allied Topics, American Society for Mass Spectrometry, Nashville, TN, May 23-27, 2004" (2004).

Mann and Kadkhodayan, "Antibody isolation and Quantitation using LC/MS and a novel 96-well immunoaffinity membrane" *52nd Conference on Mass Spectrometry and Allied Topics, American Society for Mass Spectrometry* (Nashville, TN, May 23-27, 2004).

\* cited by examiner

|   | 1 | 2 | 3 | 4 | 5 | 6 | 7 | 8 | 9 | 10 | 11 | 12 | % CV |
|---|---|---|---|---|---|---|---|---|---|----|----|----|------|
| A | 401000 | 403000 | 364000 | 416000 | 370000 | 367000 | 420000 | 417000 | 377000 | 432000 | 402000 | 362000 | 6.3 |
| B | 426000 | 437000 | 446000 | 473000 | 424000 | 443000 | 456000 | 403000 | 445000 | 431000 | 413000 | 424000 | 4.4 |
| C | 423000 | 438000 | 417000 | 406000 | 386000 | 426000 | 386000 | 391000 | 427000 | 401000 | 393000 | 377000 | 4.9 |
| D | 416000 | 403000 | 413000 | 387000 | 421000 | 363000 | 368000 | 417000 | 415000 | 403000 | 387000 | 382000 | 5.0 |
| E | 406000 | 401000 | 370000 | 421000 | 397000 | 403000 | 401000 | 416000 | 384000 | 384000 | 382000 | 355000 | 4.8 |
| F | 388000 | 393000 | 398000 | 378000 | 339000 | 420000 | 421000 | 398000 | 425000 | 390000 | 391000 | 345000 | 6.9 |
| G | 394000 | 384000 | 391000 | 385000 | 395000 | 433000 | 414000 | 387000 | 384000 | 393000 | 393000 | 418000 | 3.9 |
| H | 386000 | 382000 | 389000 | 374000 | 397000 | 397000 | 392000 | 393000 | 410000 | 408000 | 387000 | 378000 | 2.8 |
| % CV | 3.8 | 5.3 | 6.7 | 8.0 | 7.0 | 7.3 | 6.6 | 3.1 | 6.0 | 4.4 | 2.5 | 7.4 | |
Avg = 399953
Std Dev = 24119
% CV = 6.0
Figure 11
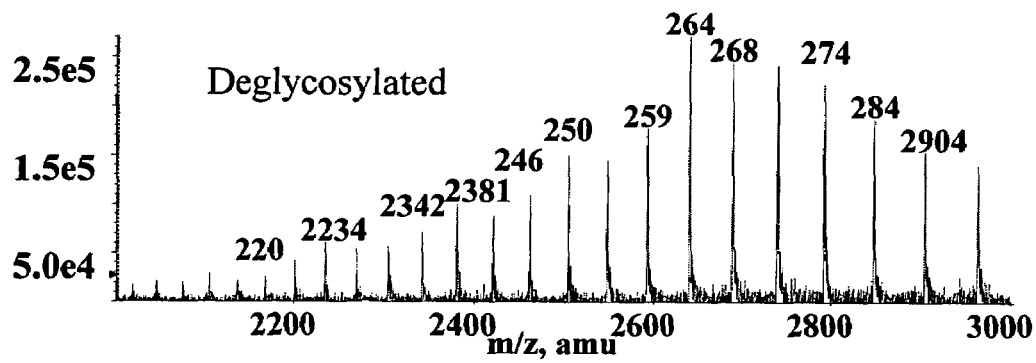
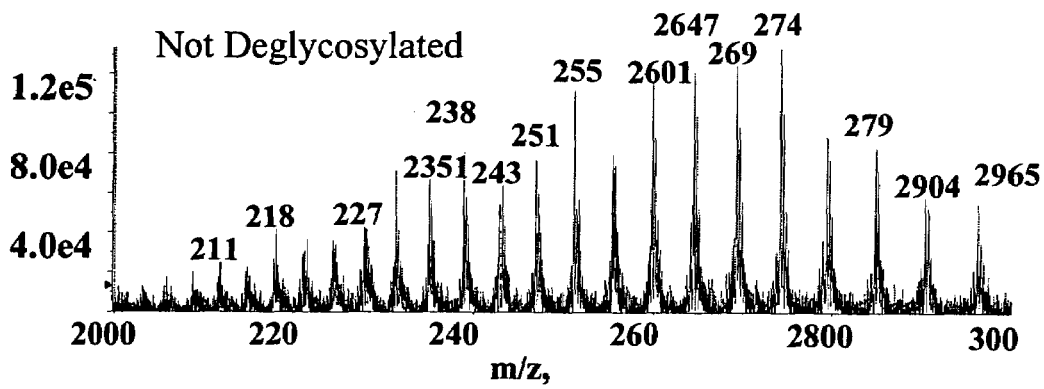
Figure 12

MASS SPECTROMETRY OF ANTIBODY CONJUGATES

This non-provisional application filed under 37 CFR §1.53 (b), claims the benefit under 35 USC §119(e) of U.S. Provisional Application Ser. No. 60/560,530 filed on Apr. 7, 2004 and U.S. Provisional Application Ser. No. 60/654,020 filed on Feb. 17, 2005.

FIELD OF THE INVENTION

The invention relates generally to methods to detect, analyze, screen, characterize, and quantitate antibody conjugate compounds, including antibody-drug conjugates, and their fragments and metabolites, by mass spectrometry. The invention also relates to methods to prepare mass spectrometric samples for pharmacokinetic studies.

BACKGROUND OF THE INVENTION

Targeted anti-cancer therapeutics are designed to reduce nonspecific toxicities and increase efficacy relative to conventional cancer chemotherapy. This approach is embodied by the powerful targeting ability of monoclonal antibodies to specifically deliver highly potent, conjugated small molecule therapeutics to a cancer cell. The pharmacokinetics and biodistribution of an antibody play a major role in determining whether its use in the clinic will be successful. Thus the antibody must be capable of being delivered to the site of action and be retained there for the length of time necessary to achieve its purpose. To evaluate properties such as pharmacokinetics and toxicity of these antibody-drug conjugates, it is useful to be able to characterize and quantitate them from plasma, urine, and other biological samples. Additionally, the ability to quantitate the free drug (not conjugated to the antibody) in the method from the same sample and the same chromatographic injection would also be useful.

A variety of mass spectrometry techniques have been employed for identification and quantitation of small molecule therapeutics in pharmacokinetic studies, such as: electron impact (EI), chemical ionization (CI), desorption chemical ionization (DCI), fast atom bombardment (FAB), electrospray ionization (ESI), matrix-assisted laser desorption/ionization (MALDI), and tandem mass spectrometry (MS/MS)(Yao et al (2001) Jour. of Chrom. B 752:9-16; Royer et al (1995) Rapid Comm. in Mass Spec. 9:495-502), including single ion monitoring (SIM) mode of ion selection for deconvolution (Souppart et al (2002) Jour. of Chrom. B 774: 195-203; Wong et al (2001) Jour. of Chrom. 765:55-62; Yao et al (1998) Jour. of Chrom. B 718:77-85; Abdel-Hamid et al (2001) Jour. of Chrom. B 753:401-408; Marques et al (2001) Jour. of Chrom. 762:87-95). These methods and instrumentation require the separation of the various analytes from biological fluids for sufficient sensitivity. Such purification can be labor-intensive, slow, and require large volumes of sample fluids due to the low concentration of the analytes of interest in samples such as cell culture medium, human plasma, urine, and bile.

The direct combination of a separation/isolation/purification front-end step coupled with detection/characterization/quantitation by mass spectrometry is effective for metabolic studies of complex biological samples. Typically, LC/MS is used for characterization of antibodies (Martin et al (1997) Cancer Chemother. Pharmacol. 40:189-201; WO 03/046571; WO 03/046572), and ELISA is used for quantitation in biological matrices (Murray et al (2001) J. Imm. Methods 255: 41-56; Kirchner et al (2004) Clin. Pharmacokinetics 43(2): 83-95). ELISA assays typically are sensitive and amenable to high-throughput screens.

Recent advances in protein analysis by mass spectrometry (MS) are due to front-end gas phase ionization and introduction techniques such as electrospray ionization (ESI), matrix-assisted laser desorption ionization (MALDI, US 2003/0027216) and Surface Enhanced Laser Desorption Ionization (SELDI, U.S. Pat. No. 6,020,208), as well as improvements in instrument sensitivity, resolution, mass accuracy, bioinformatics, and software data deconvolution algorithms ("Electrospray Ionization Mass Spectrometry: Fundamentals, Instrumentation, and Applications", Cole, R. B., Ed. (1997) Wiley, N.Y.; "Modem Protein Chemistry: Practical Aspects", Howard, G. C. and Brown, W. E., Eds. (2002) CRC Press, Boca Raton, Fla., p. 71-102;). The primary (sequence), secondary, and tertiary structure of proteins can be probed and elucidated with MS. Electrospray ionization (ESI) provides for the atmospheric pressure ionization (API) of a liquid sample. The electrospray process creates highly-charged droplets that, under evaporation, create ions representative of the species contained in the solution. An ion-sampling orifice of a mass spectrometer may be used to sample these gas phase ions for mass analysis. The response for an analyte measured by the mass spectrometer detector is dependent on the concentration of the analyte in the fluid and independent of the fluid flow rate.

Antibody therapy has been established for the targeted treatment and diagnosis of patients with cancer, immunological and angiogenic disorders. One example, HERCEPTIN® (trastuzumab; Genentech, Inc.; South San Francisco, Calif.) is a recombinant DNA-derived humanized monoclonal antibody that selectively binds to the extracellular domain (ECD) of the human epidermal growth factor receptor2 protein, HER2 (ErbB2)(U.S. Pat. No. 5,821,337; U.S. Pat. No. 6,054, 297; U.S. Pat. No. 6,407,213; U.S. Pat. No. 6,639,055; Coussens et al (1985) Science 230:1132-9; Slamon, et al (1989) Science 244:707-12). Trastuzumab is an IgG1 kappa antibody that contains human framework regions with the complementarity-determining regions (cdr) of a murine antibody (4D5) that binds to HER2. Trastuzumab binds to the HER2 antigen and thus inhibits the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). HERCEPTIN® as a single agent is indicated for the treatment of patients with metastatic breast cancer whose tumors overexpress the HER2 protein and who have received one or more chemotherapy regimens for their metastatic disease. HERCEPTIN® in combination with paclitaxel is indicated for treatment of patients with metastatic breast cancer whose tumors overexpress the HER2 protein and who have not received chemotherapy for their metastatic disease. HERCEPTIN® is clinically active in patients with ErbB2-overexpressing metastatic breast cancers that have received extensive prior anti-cancer therapy (Baselga et al (1996) J. Clin. Oncol. 14:737-744).

The aim of antibody therapy and diagnosis is to exploit the combination of high specificity and affinity of the antibody-antigen interaction, to enable detection and/or treatment of a particular lesion or disorder. The antibody is used alone, or is conjugated, i.e. loaded, with another moiety such as a detection label, pharmacokinetic modifier, radioisotope, toxin, or drug. The use of antibody-drug conjugates (ADC), i.e. immunoconjugates, for the local delivery of cytotoxic or cytostatic agents to kill or inhibit tumor cells in the treatment of cancer (Syrigos and Epenetos (1999) Anticancer Research 19:605-

614; Niculescu-Duvaz and Springer (1997) Adv. Drug Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (eds), pp. 475-506). Maximal efficacy with minimal toxicity is sought thereby. Efforts to design and refine ADC have focused on the selectivity of monoclonal antibodies (MAbs) as well as drug-linking and drug-releasing properties. Both polyclonal antibodies and monoclonal antibodies linked to drugs including daunomycin, doxorubicin, methotrexate, and vindesine have been reported as useful in these strategies (Rowland et al, (1986) Cancer Immunol. Immunother., 21:183-87). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al, (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins and drugs may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Exemplary antibody-drug conjugates include MYLOTARG™ (gemtuzumab ozogamicin, Wyeth Pharmaceuticals), a huCD33 antibody linked to calicheamicin, which was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety DM1, is advancing into Phase II trials for the treatment of cancers that express CanAg, such as colon, pancreatic, gastric, and others. MLN-2704 (Millennium Pharm., BZL Biologics, Immunogen Inc.), an antibody-drug conjugate composed of the anti-prostate specific membrane antigen (PSMA) monoclonal antibody also linked to DM1, is under development for the potential treatment of prostate tumors. The auristatin peptides, auristatin E (AE) and monomethylauristatin (MMAE) synthetic analogs of dolastatin, were conjugated to chimeric monoclonal antibodies cBR96 (specific to Lewis Y on carcinomas) and cAC10 (specific to CD30 on hematological malignancies), and are under therapeutic development (Doronina et al (2003) Nature Biotechnology 21(7):778-784; Francisco et al (2003) Blood 102:1458-1465).

The above-mentioned antibody-drug conjugates (ADC) which are approved or under development for therapeutic use are heterogeneous mixtures where the process of covalent attachment of the drug moiety to the antibody is largely uncontrolled and the resulting conjugation products are incompletely characterized. In addition, the drug loading (drug/Ab ratio) is a statistical average for the collection of ADC molecules in a composition or formulation. Because of the heterogeneous nature of antibody-drug conjugate compositions, pharmacokinetic samples collected from biological sources after administration are difficult to evaluate. ELISA assays are limited to detection of antibody-antigen binding (DiJoseph et al (2004) Blood 103:1807-1814). UV spectroscopy can measure the total absorbance of certain fluorescent or UV-active drug moieties or metabolites, but cannot distinguish between free drug and antibody-drug conjugate.

SUMMARY OF THE INVENTION

An aspect of the invention includes methods to detect, screen, and quantitate antibody conjugate compounds and compositions, antibodies, and fragments and metabolites thereof, by affinity separation, chromatography, and mass spectrometry. Exemplary methods of mass spectrometry include electrospray ionization (ESI), single ion monitoring (SIM) mass spectrometry (MS). The practice or technique of SIM is sometimes referred to as selected ion monitoring or selective ion monitoring.

An aspect of the invention includes a method for detecting antibody-drug conjugate compounds comprising:

(i) providing an antibody-drug conjugate compound having Formula I:

$$\text{Ab-(L-D)}_p \qquad \qquad \text{I}$$

wherein

Ab is an antibody;

D is a drug moiety;

L is a linker covalently attached to Ab, and covalently attached to D; and p is 1, 2, 3, 4, 5, 6, 7, or 8;

(ii) contacting the antibody-drug conjugate compound, and optionally an antibody of Formula I where p is 0, or fragments or metabolites thereof, with a biological source;

(iii) collecting a biological sample from the biological source;

(iv) processing the biological sample to form an analysis sample;

(v) applying the analysis sample to a separation media to effect separation of more than one sample constituents wherein a separated sample constituent comprises an antibody-drug conjugate compound having the Formula I, or fragment or metabolite thereof, and where p is 0, 1, 2, 3, 4, 5, 6, 7, or 8; and (vi) establishing the mass or mass to charge ratio of one or more separated sample constituents by mass spectrometry.

The invention includes methods for screening a mixture of antibody-drug conjugate compounds to determine the relative clearance of the compounds, or fragments or metabolites thereof, in a biological source, such as a mammal, tissue, or cell culture.

The invention includes methods for detecting by mass spectrometry, compounds of a heterogeneous mixture of antibody-drug conjugate compounds having Formula I, wherein the mixture includes compounds having more than one drug loading value, p, where p may be 1, 2, 3, 4, 5, 6, 7, or 8; the method comprises performing mass spectrometry on a sample comprising the heterogeneous mixture of antibody-drug conjugate compounds and detecting more than one compound of the mixture, or fragments or metabolites thereof.

The invention includes methods to quantitate levels of both free drug and antibody-drug conjugates in plasma by LC/MS with a single analysis.

The invention includes methods for studying in vivo metabolism of antibody-drug conjugates.

The invention includes methods of pharmacokinetic analysis of antibody-drug conjugates after administration to mammals.

The invention includes methods of patient profiling by measuring susceptibility and response to antibody-drug conjugate therapeutic treatment.

The invention includes diagnostic methods of diagnosing the presence or absence of a condition or disease characterized by the over-expression of a protein or antigen by administration of an antibody-drug conjugate to a mammal, tissue, or cell culture.

The invention includes Immunoaffinity Membrane/LC/MS methods having immunoaffinity membrane (IAM) selection and reverse phase liquid chromatography (LC) front-end steps coupled with a back-end mass spectrometry (MS) detection step to isolate, cleanup, and detect antibody-drug conjugates in plasma.

The SIM results for antibody conjugates and antibodies analyzed by the methods of the present invention are surprising and unexpected because SIM has not been recognized as useful for such large molecules. The methods of the present invention combine high resolution of ions and stability of the ion envelope by control of the declustering potential, pH, and the mobile phase. In addition, selection of high mass ions, rather than the most abundant, highest peak, ion, for SIM avoids matrix interference typical at the lower mass range.

The invention may be understood by reference to the following detailed description of the exemplary embodiments, taken in conjunction with the accompanying drawings, figures, and Examples. The discussion below is descriptive, illustrative and exemplary and is not to be taken as limiting the scope defined by any appended claims.

BRIEF DESCRIPTION OF THE DRAWINGS

FIG. 11 shows whole plate accuracy and precision of a monoclonal antibody (3 μg) in plasma FIG. 12 shows the effect of deglycosylation of the heavy chain of a monoclonal antibody, conducted on the affinity membrane.

DETAILED DESCRIPTION OF THE EXEMPLARY EMBODIMENTS

Figure 1:
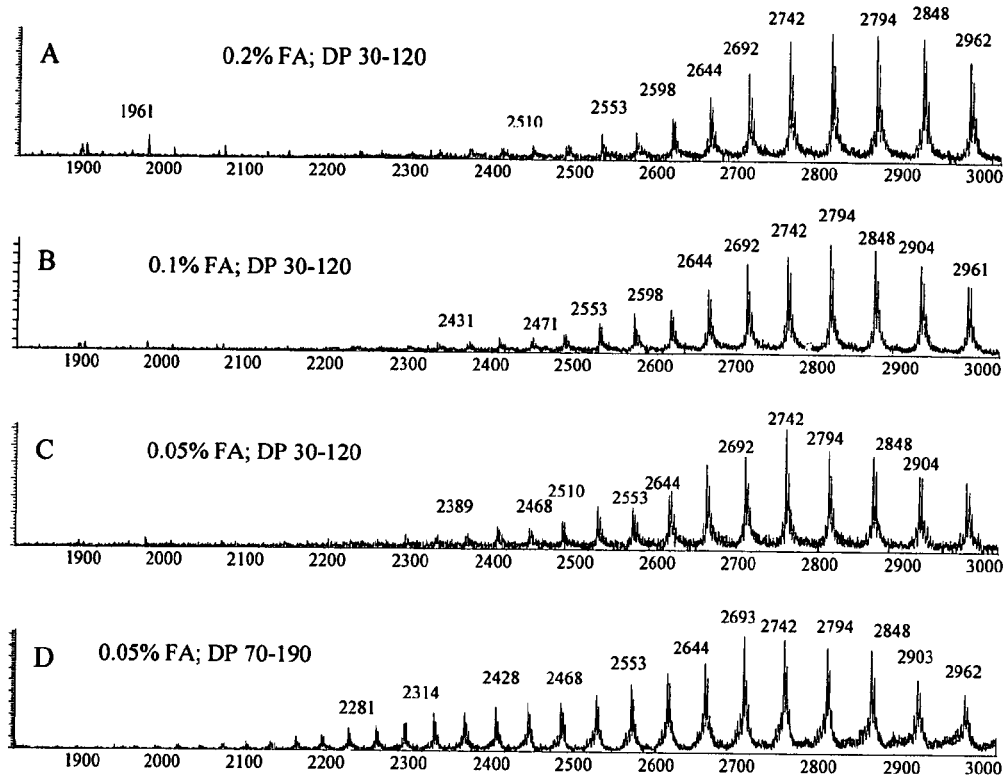
FIG. 1 shows the Q1 mass spectrum of the intact glycosylated antibody, trastuzumab, under different formic acid (FA) concentrations and declustering potential (DP).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York.

When trade names are used herein, applicants intend to independently include the trade name product formulation, the generic drug, and the active pharmaceutical ingredient(s) of the trade name product.

DEFINITIONS

Unless stated otherwise, the following terms and phrases as used herein are intended to have the following meanings:

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species.

An antibody is a protein generated by the immune system that is capable of recognizing and binding to a specific antigen. (Janeway, et al (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "antibody," as used herein, also refers to a full-length immunoglobulin molecule or an immunologically active portion of a full-length immunoglobulin molecule, i e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

An "intact antibody" herein is one comprising a VL and VH domains, as well as complete light and heavy chain constant domains.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized Uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

"Antibody fragments" comprise a portion of an intact antibody, e.g. comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragment(s).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g. IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native antibody or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (MAb) to an antigen-of-interest can be prepared by using any technique known in the art which provides for the production of antibody molecules by continuous cell lines in culture. These include, but are not limited to, the hybridoma technique originally described by Köhler and Milstein (1975, *Nature* 256, 495-497), the human B cell hybridoma technique (Kozbor et al, 1983, *Immunology Today* 4: 72), and the EBV-hybridoma technique (Cole et al, 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the MAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al, 1983, *Proc. Natl. Acad. Sci. U.S.A.* 80, 7308-7312; Kozbor et al, 1983, *Immunology Today* 4, 72-79; and Olsson et al, 1982, *Meth. Enzymol.* 92, 3-16).

The antibody can also be a bispecific antibody. Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al, *Methods in Enzymology*, 1986, 121:210; Rodrigues et al, 1993, *J. of Immunology* 151:6954-6961; Carter et al, 1992, *Bio/Technology* 10:163-167; Carter et al, 1995, *J. of Hematotherapy* 4:463-470; Merchant et al, 1998, *Nature Biotechnology* 16:677-681. Methods for making bispecific antibodies are known in the art (Milstein et al, 1983, *Nature* 305:537-539; WO 93/08829; Traunecker et al, *EMBO J.* 10:3655-3659 (1991). Using such techniques, bispecific antibodies can be prepared for conjugation as ADC in the treatment or prevention of disease as defined herein.

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, $C_H2$, and $C_H3$ regions. The first heavy-chain constant region ($C_H1$) may contain the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Hybrid or bifunctional antibodies can be derived either biologically, ie., by cell fusion techniques, or chemically, especially with cross-linking agents or disulfide-bridge forming reagents, and may comprise whole antibodies or fragments thereof (EP 105360; WO 83/03679; EP 217577).

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay)(See,for e.g., Kabat et al, 1991, *Sequences of Proteins of Immunological Interest*, Fifth Edition, National Institute of Health, Bethesda, Md.; Kabat E et al, 1980, *J. of Immunology* 125(3): 961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs)(e.g., as described in U.S. Pat. No. 4,946,778; Bird, (1988), *Science* 242:423-42; Huston et al, (1988) Proc. Natl. Acad. Sci. USA 85:5879-5883; and Ward et al, (1989) Nature 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions (U.S. Pat. No. 4,816,567; and U.S. Pat. No. 4,816,397, which are incorporated herein by reference in their entirety.) Chimeric and humanized monoclonal antibodies can be produced by recombinant DNA techniques known in the art, for example using methods described in WO 87/02671; EP 184,187; EP 171496; EP 173494; WO 86/01533; U.S. Pat. No. 4,816,567; EP 12023; Berter et al, (1988) Science 240:1041-1043; Liu et al, (1987) Proc. Natl. Acad. Sci. USA 84:3439-3443; Liu et al, (1987) J. Immunol. 139:3521-3526; Sun et al, (1987) Proc. Natl. Acad. Sci. USA 84:214-218; Nishimura et al, (1987) Cancer. Res. 47:999-1005; Wood et al, (1985) Nature 314: 446-449; and Shaw et al, (1988) J. Natl. Cancer Inst. 80:1553-1559; Morrison,(1985) Science 229: 1202-1207; Oi et al, (1986) BioTechniques 4:214; U.S. Pat. No. 5,225,539; Jones et al, (1986) Nature 321: 552-525; Verhoeyan et al. (1988) Science 239:1534; and Beidler et al, 1988, J. Immunol. 141: 4053-4060; each of which is incorporated herein by reference in its entirety.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, *Int. Rev. Immunol.* 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) *Biotechnology* 12:899-903). Human antibodies can also be produced using various techniques known in the art, including phage display libraries (Hoogenboom and Winter, J. Mol. Biol., 227:381 (1991); Marks et al, J. Mol. Biol., 222:581 (1991)).

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies include analogs and derivatives that are either modified, ie., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies in ADC include antibodies having modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see: WO 97/34631, which is incorporated herein by reference in its entirety). Antibodies immunospecific for a cancer cell antigen can be obtained commercially, for example, from Genentech, Inc. (South San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

The term "receptor" includes any peptide, protein, glycoprotein, polycarbohydrate, or lipid that is uniquely expressed or overexpressed on the surface of a cell, and is exposed on the surface of a cell in a manner that will allow interaction with a circulating targeting agent, such as an antibody-drug conjugate. Cells bearing receptors include tumor cells.

The term "patient" includes human and veterinary subjects. "Mammal" for purposes of administration of, or contact with, antibody-drug conjugates refers to any animal classified as a mammal, including human, domestic and farm animals, nonhuman primates, and any other animal that has mammalian tissue.

The term "Biological sample" means (i) blood, bile, urine, or feces; (ii) tissue extract; and (iii) cell culture media, cell lysate, or cell extract.

The term "Biological source" means (i) mammals such as a mouse, a rat, a rabbit, a dog, a monkey, or a human; (ii) mammalian tissue; and (iii) cultured cells.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

"Alkyl" is a $C_1$-$C_{18}$ hydrocarbon moiety containing normal, secondary, tertiary or cyclic carbon atoms. Examples of alkyl radicals include $C_1$-$C_8$ hydrocarbon moieties such as: methyl(Me, —$CH_3$), ethyl (Et, —$CH_2CH_3$), 1-propyl(n-Pr, n-propyl, —$CH_2CH_2CH_3$), 2-propyl(i-Pr, i-propyl, —CH ($CH_3$)$_2$), 1-butyl (n-Bu, n-butyl, —$CH_2CH_2CH_2CH_3$), 2-methyl-1-propyl(i-Bu, i-butyl, —$CH_2CH(CH_3)_2$), 2-butyl (s-Bu, s-butyl, —$CH(CH_3)CH_2CH_3$), 2-methyl-2-propyl(t-Bu, t-butyl, —$C(CH_3)_3$), 1-pentyl (n-pentyl, —$CH_2CH_2CH_2CH_2CH_3$), 2-pentyl(—$CH(CH_3)$ $CH_2CH_2CH_3$), 3-pentyl (—$CH(CH_2CH_3)_2$), 2-methyl-2-butyl(—$C(CH_3)_2CH_2CH_3$), 3-methyl-2-butyl(—$CH(CH_3)CH$ $(CH_3)_2$), 3-methyl-1-butyl(—$CH_2CH_2CH(CH_3)_2$), 2-methyl-1butyl(—$CH_2CH(CH_3)CH_2CH_3$), 1-hexyl(—$CH_2CH_2CH_2CH_2CH_2CH_3$), 2-hexyl(—$CH(CH_3)$ $CH_2CH_2CH_2CH_3$), 3-hexyl (—$CH(CH_2CH_3)$ ($CH_2CH_2CH_3$)), 2-methyl-2-pentyl(—$C(CH_3)_2$ $CH_2CH_2CH_3$), 3-methyl-2-pentyl(—$CH(CH_3)CH(CH_3)$ $CH_2CH_3$), 4-methyl-2-pentyl(—$CH(CH_3)CH_2CH(CH_3)_2$), 3-methyl-3-pentyl(—$C(CH_3)(CH_2CH_3)_2$), 2-methyl-3-pentyl(—$CH(CH_2CH_3)CH(CH_3)_2$), 2,3-dimethyl-2-butyl(—C ($CH_3$)$_2CH(CH_3)_2$), 3,3-dimethyl-2-butyl(—$CH(CH_3)C$ ($CH_3$)$_3$, 1-heptyl, 1-octyl, cyclopropyl, cyclobutyl, cyclopentyl, cyclohexyl, cycloheptyl, and cyclooctyl.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like.

"Substituted alkyl", and "substituted aryl" mean alkyl and aryl, respectively, in which one or more hydrogen atoms are each independently replaced with a substituent. Typical substituents include, but are not limited to, —X, —R, —O⁻, —OR, —SR, —S⁻, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NR$_2$, —SO$_3$⁻, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO⁻$_3$, —PO$_3$H$_2$, —C(=O)R, —C(=O)X, —C(=S)R,—CO$_2$R, —CO$_2$⁻, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently H, $C_1$-$C_{18}$ alkyl, $C_6$-$C_{20}$ aryl, $C_3$-$C_{14}$ heterocycle, or protecting group. Alkylene, alkenylene, and alkynylene groups as described above may also be similarly substituted.

"Heteroaryl", "heterocyclyl", and "heterocycle" all refer to a ring system in which one or more ring atoms is a heteroatom, e.g. nitrogen, oxygen, and sulfur. The heterocycle radical comprises 1 to 20 carbon atoms and 1 to 5 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl(piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" and "carbocyclyl" mean a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5],[5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

"Reactive functional groups" include, but are not limited to, olefins, acetylenes, alcohols, phenols, ethers, oxides, halides, aldehydes, ketones, carboxylic acids, esters, carbonates, amides, cyanates, isocyanates, thiocyanates, isothiocyanates, amines, hydrazines, hydrazones, hydrazides, diazo, diazonium, nitro, nitriles, mercaptans (thiols), sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, orthoesters, sulfites, enamines, ynamines, ureas, pseudoureas, semicarbazides, carbodiimides, carbamates, imines, azides, azo compounds, azoxy compounds, and nitroso compounds. Exemplary reactive functional groups include N-hydroxysuccinimide (NHS) esters, para-nitrophenyl (PNP) carbonates, pentafluorophenyl (PFP) carbonates, and maleimides. See: Sandler and Karo, Eds. "Organic Functional Group Preparations", Academic Press, San Diego, 1989.

"Linker", "Linker Unit", or "link" means a chemical moiety comprising a covalent bond or a chain of atoms that covalently attaches an antibody to a drug moiety. In various embodiments, a linker is specified as L. Linkers include a divalent radical such as an alkylene, an aryldiyl, a heteroaryldiyl, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Exemplary linker abbreviations include: MC=6-maleimidocaproyl, MP=maleimidopropanoyl, val-cit=valine-citrulline, dipeptide site in protease-cleavable linker, ala-phe=alanine-phenylalanine, dipeptide site in protease-cleavable linker, PAB=p-aminobenzyloxycarbonyl ("self immolative" portion of linker), SPP=N-Succinimidyl 4-(2-pyridylthio)pentanoate, SMCC=N-Succinimidyl 4-(N-maleimidomethyl)cyclohexane-1 carboxylate, SIAB=N-Succinimidyl(4-iodo-acetyl)aminobenzoate The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

The following acronyms, terms, and abbreviations are used herein and have the indicated definitions:

Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, LC/MS is liquid chromatography and mass spectrometry, MeOH is methanol, Mtr is 4-anisyldiphenylmethyl (or 4-methoxytrityl), nor is (1S,2R)-(+)-norephedrine, PBS is phosphate-buffered saline (Ph 7.4), PEG is polyethylene glycol, Ph is phenyl, Pnp is p-nitrophenyl, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Antibodies

The antibody unit (Ab-) of Formula I includes within its scope any unit of an antibody (Ab) that binds or reactively associates or complexes with a receptor, antigen or other receptive moiety associated with a given target-cell population. An antibody can be any protein or protein-like molecule that binds to, complexes with, or reacts with a moiety of a cell population sought to be therapeutically or otherwise biologically modified. In one aspect, the antibody unit acts to deliver the Drug unit to the particular target cell population with which the antibody unit reacts. Such antibodies include, but are not limited to, large molecular weight proteins such as, full-length antibodies and antibody fragments.

Useful non-immunoreactive protein, polypeptide, or peptide antibodies which comprise Ab in Formula I antibody-drug conjugates (ADC) include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Antibodies which comprise Ab in Formula I antibody-drug conjugates (ADC) and which may be useful in the treatment of cancer include, but are not limited to, antibodies against tumor-associated antigens (TAA). Such tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(35) listed below. For convenience, information relating to these antigens, all of which are known in the art, is listed below and includes names, alternative names, Genbank accession numbers and primary reference(s). Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4:
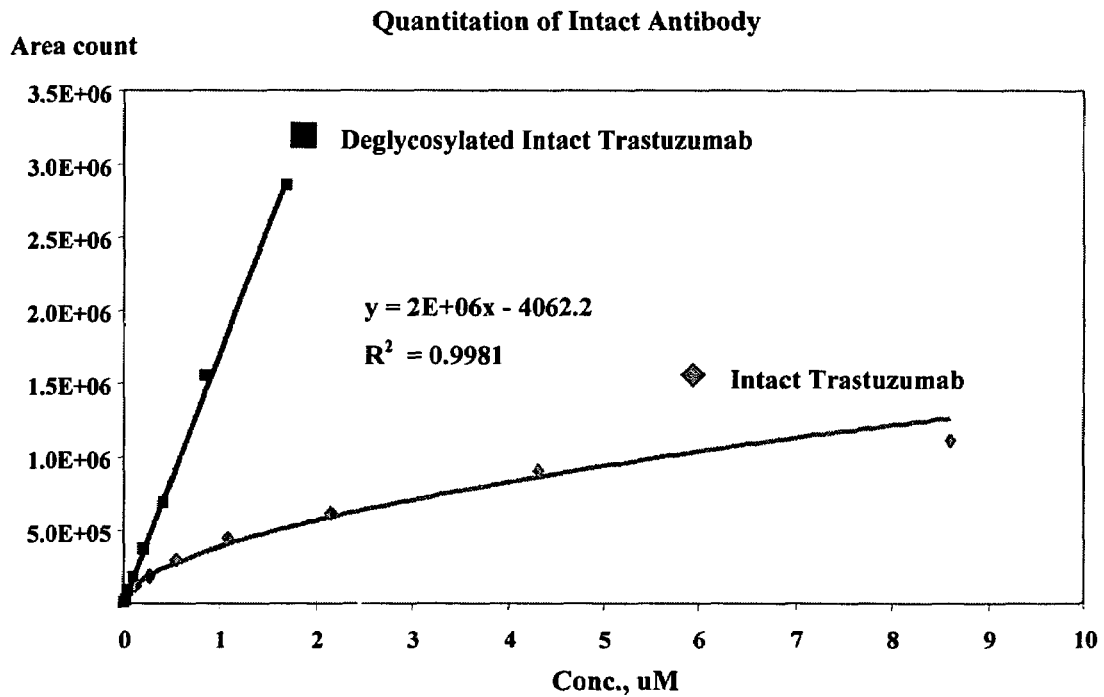
FIG. 4 shows calibration for quantitation by ESI-MS, at different concentrations of: intact trastuzumab (aHer2) and deglycosylated intact trastuzumab.

Tumor-Associated Antigens (1)-(35):

(1) BMPR1B (bone morphogenetic protein receptor-type IB, Genbank accession no. NM_001203)

ten Dijke, P., et al Science 264 (5155):101-104 (1994), Oncogene 14 (11):1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377(Page 349-350); WO200230268 (Claim 27; Page 376); WO200148204 (Example; FIG. 4) NP_001194 bone morphogenetic protein receptor, type IB/pid=NP_001194.1

Cross-references: MIM:603248; NP_001194.1; NM_001203_1

(2) E16 (LAT1, SLC7A5, Genbank accession no. NM_003486)

Figure 3:
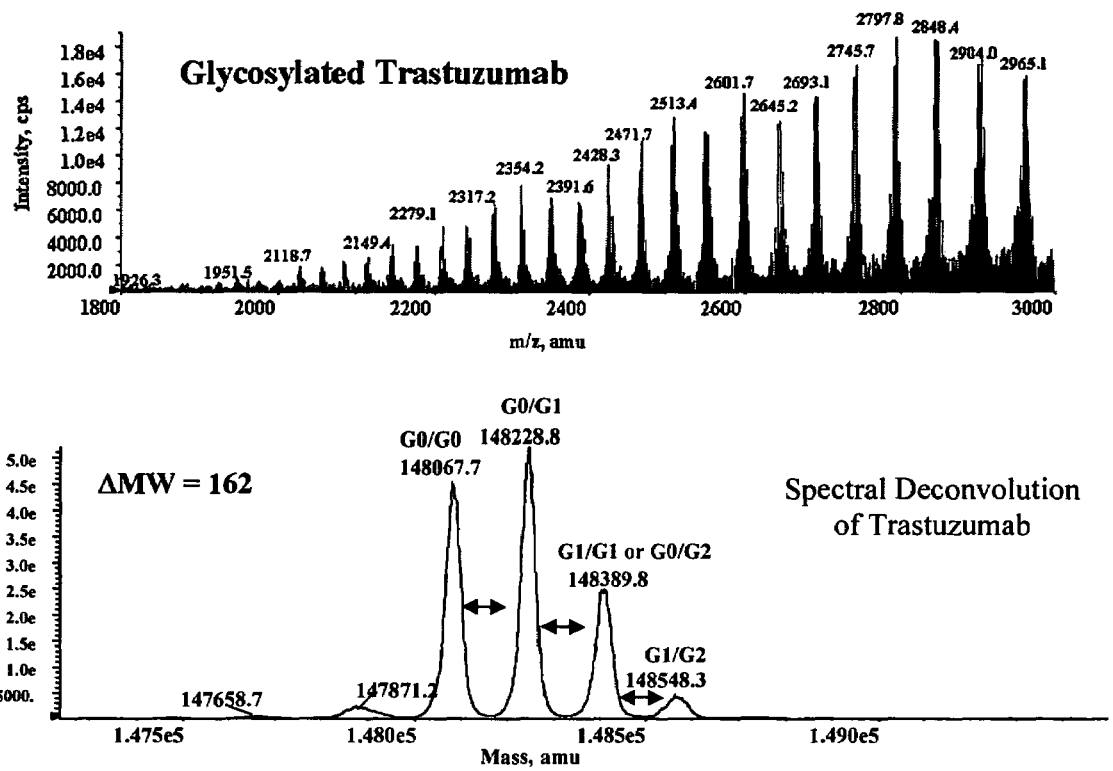
FIG. 3 shows ESI-MS of glycosylated trastuzumab and spectral deconvolution.

Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+system), member 5/pid=NP_003477.3—*Homo sapiens*

Cross-references: MIM:600182; NP_003477.3; NM_015923; NM_003486_1

(3) STEAP1 (six transmembrane epithelial antigen of prostate, Genbank accession no. NM_012449)

Cancer Res. 61 (15), 5857-5860 (2001), Hubert, R. S., et al (1999) Proc. Natl. Acad. Sci. U.S.A. 96 (25): 14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 12); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1

(4) 0772P (CA 125, MUC16, Genbank accession no. AF361486)

J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); US2003091580 (Claim 6); WO200206317 (Claim 6; Page 400-408);

Cross-references: GI:34501467; AAK74120.3; AF361486_1

(5) MPF (MPF, MSLN, SMR, megakaryocyte potentiating factor, mesothelin, Genbank accession no. NM_005823)

Yamaguchi, N., et al Biol. Chem. 269 (2), 805-808 (1994), Proc. Natl. Acad. Sci. U.S.A. 96 (20): 11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57);

Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A. et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140);

Cross-references: MIM:604217; NP_006415.1; NM_006424_1

(7) Sema 5b (FLJ10372, KIAA1445, Mm. 42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878)

Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 4143, 48-58); WO2003054152 (Claim 20); WO2003101400 (Claim 11);

Accession: Q9P283; EMBL; AB040878; BAA95969.1. Genew; HGNC:10737;

(8) PSCA hlg (2700050C12Rik, C530008O16Rik, RIKEN cDNA 2700050C12, RIKEN cDNA 2700050C12 gene, Genbank accession no. AY358628);
US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20);
Cross-references: GI:37182378; AAQ88991.1; AY358628_1

Figure 2:
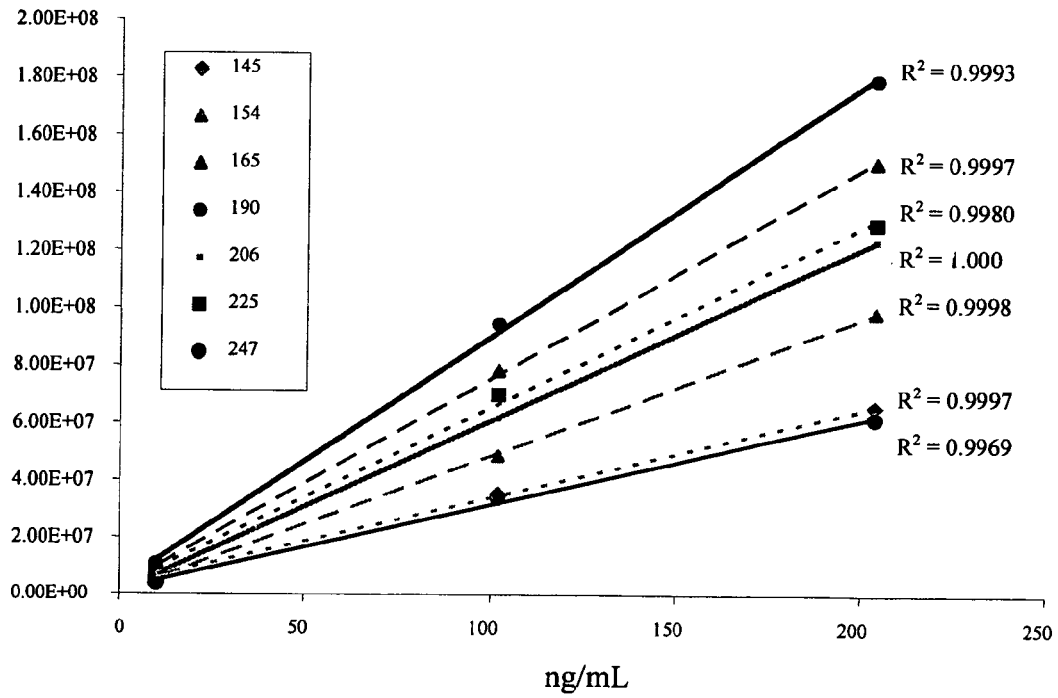
FIG. 2 shows the linearity of Q1 ions extracted from a standard curve over a wide range of charged states of the light chain of trastuzumab-MC-vc-PAB-MMAE from a Q1 scan.
Figure 6:
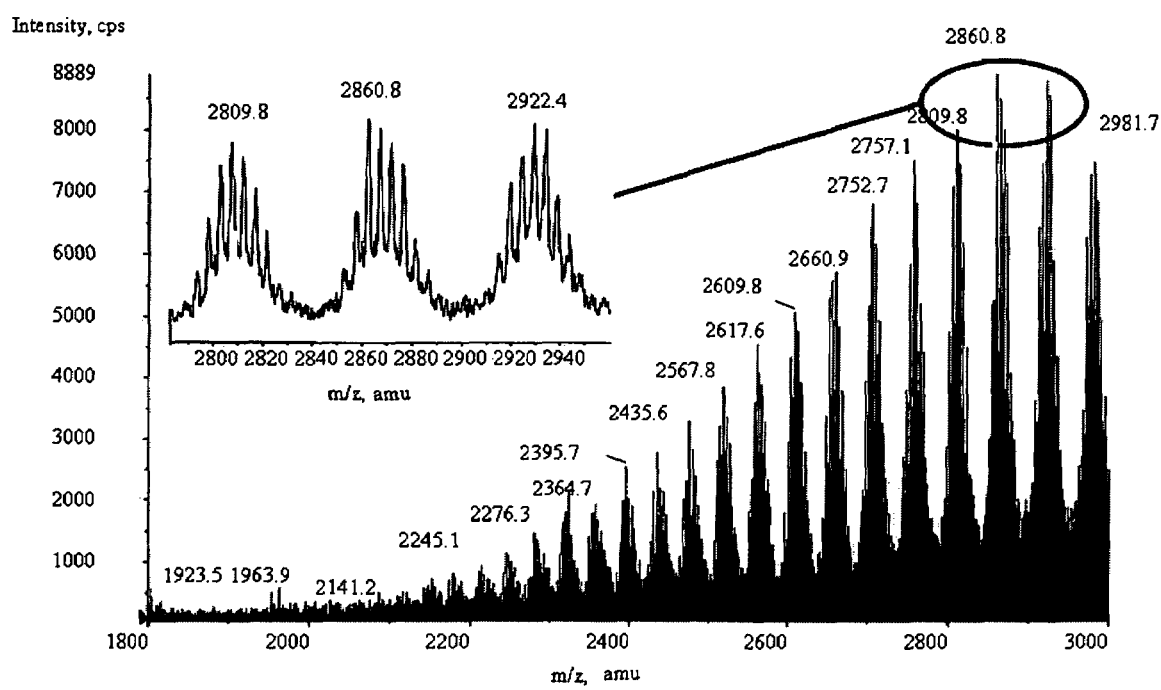
FIG. 6 shows ESI-MS of an antibody-linker conjugate, trastuzumab-SPP, after deglycosylation.

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004 (040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; US6518404 (FIG. 3); US5773223 (Claim 1a; Col 31-34); WO2004001004;

(10) MSG783 (RNF124, hypothetical protein FLJ20315, Genbank accession no. NM_017763);
WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6);
Cross-references: LocusID:54894; NP_060233.2; NM_017763_1

Figure 10:
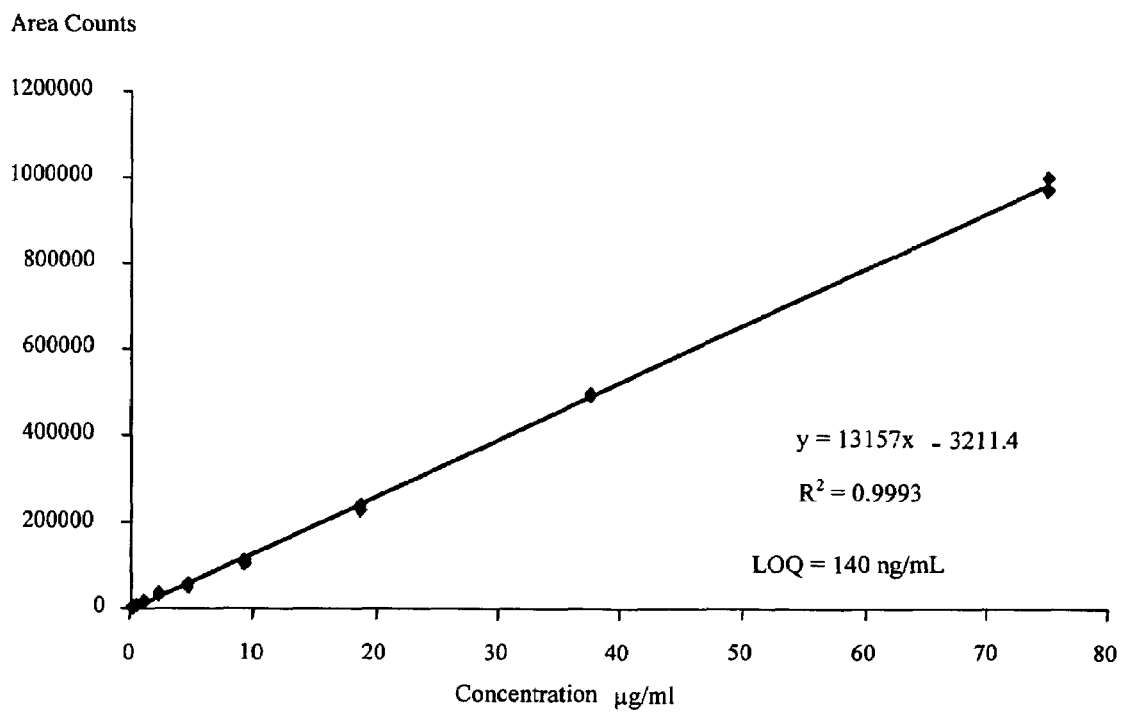
FIG. 10 shows a plasma calibration curve for the light chain of a monoclonal antibody-drug conjugate. LOQ=lower limit of quantitation

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10);
Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636)
Xu, X. Z., et al Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D);
Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); US5854399 (Example 2; Col 17-18); U.S. Pat. No. 5,792,616 (FIG. 2);
Cross-references: MIM:187395; NP_003203.1; NM_003212_1

Figure 9:
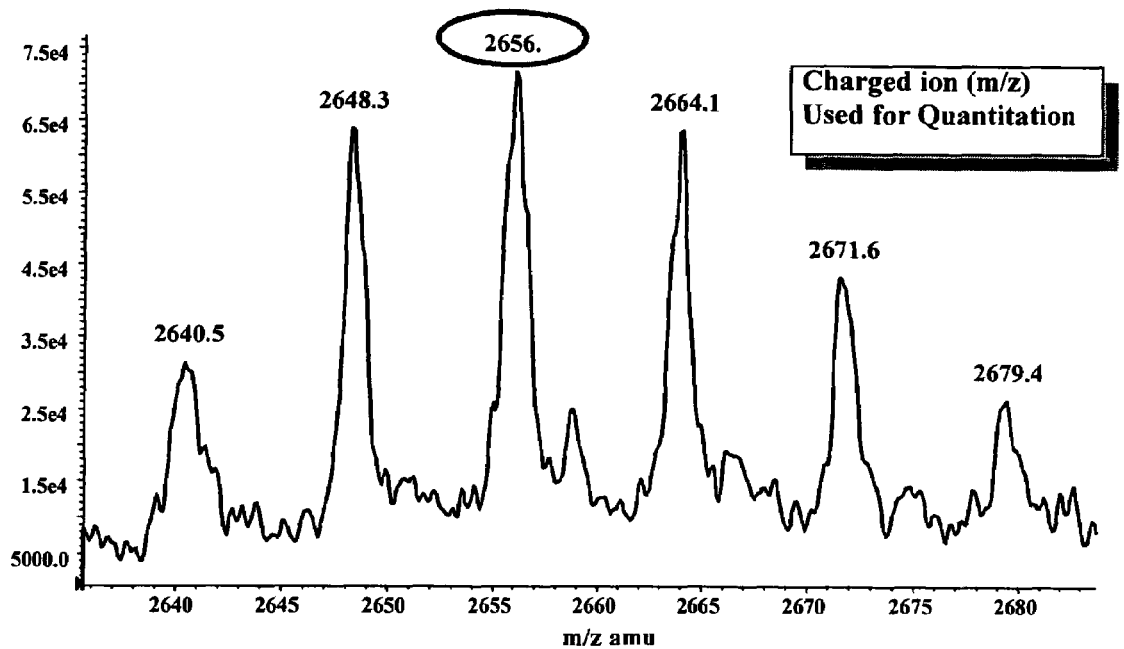
FIG. 9 shows the charged ions (m/z) prior to deconvolution of the spectra of trastuzumab-rhodamine conjugate after deglycosylation of FIG. 8, which are used for quantitation.

(14) CD21 (CR2 (Complement receptor 2) or C3DR (C3d/Epstein Barr virus receptor) or Hs. 73792 Genbank accession no. M26004)
Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIG. 9.1-9.9); WO2004020595 (Claim 1);
Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674)
Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (Claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);
Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764)
Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25);

Cross-references: MIM:606509; NP_110391.2; NM_030764_1

Figure 7:
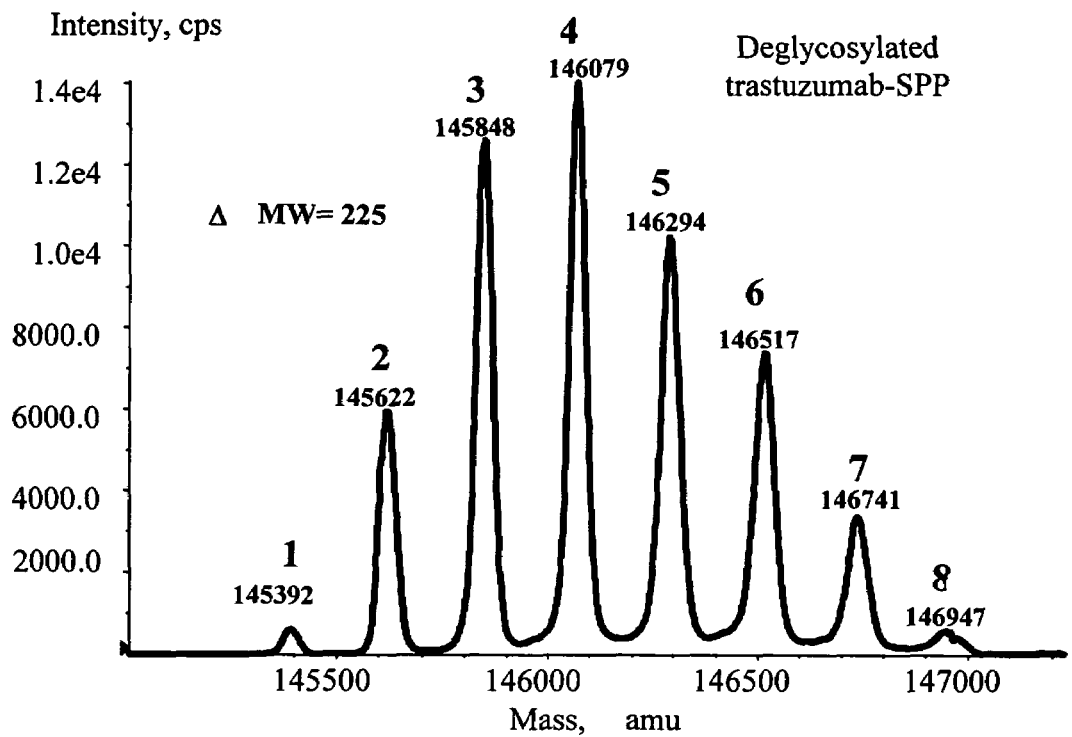
FIG. 7 shows a deconvoluted spectrum of the raw data of FIG. 6.

(17) HER2 (ErbB2, Genbank accession no. M11730)
Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 11); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4);
Accession: P04626; EMBL; M11767; AAA35808.1. EMBL; M11761; AAA35808.1.

Figure 8:
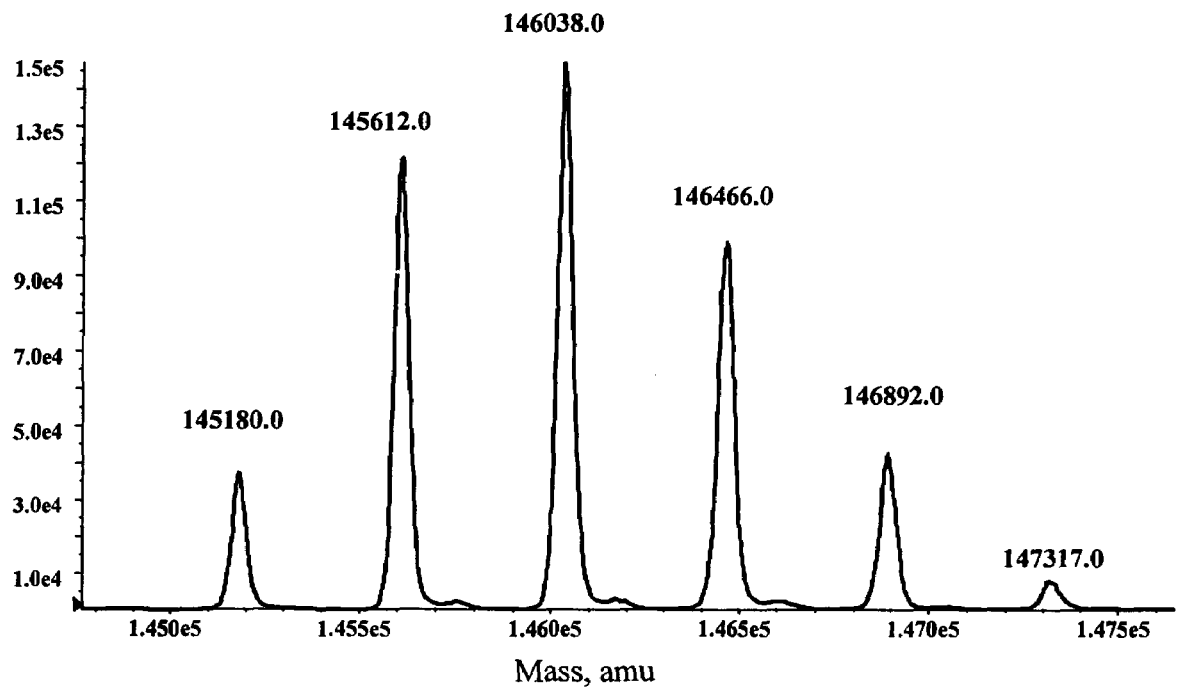
FIG. 8 shows a deconvolution spectra of trastuzumab-rhodamine conjugate after deglycosylation.

(18) NCA (CEACAM6, Genbank accession no. M18728);
Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2);
Accession: P40199; Q14920; EMBL; M29541; AAA59915.1. EMBL; M18728;

(19) MDP (DPEP1, Genbank accession no. BC017023)
Proc. Natl. Acad. Sci. U.S.A. 99 (26): 16899-16903 (2002)); WO2003016475 (Claim 1); WO200264798 (Claim 33; Page 85-87); JP05003790 (FIG. 6-8); WO9946284 (FIG. 9);
Cross-references: MIM: 179780; AAH17023.1; BC017023_1

(20) IL20Rα (IL20Ra, ZCYTOR7, Genbank accession no. AF184971);
Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59);
Accession: Q9UHF4; Q6UWA9; Q96SH8; EMBL; AF184971; AAF01320.1.

(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903,2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442)
Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42);
Cross-references: MIM:600997; NP_004433.2; NM_004442_1

Figure 17:
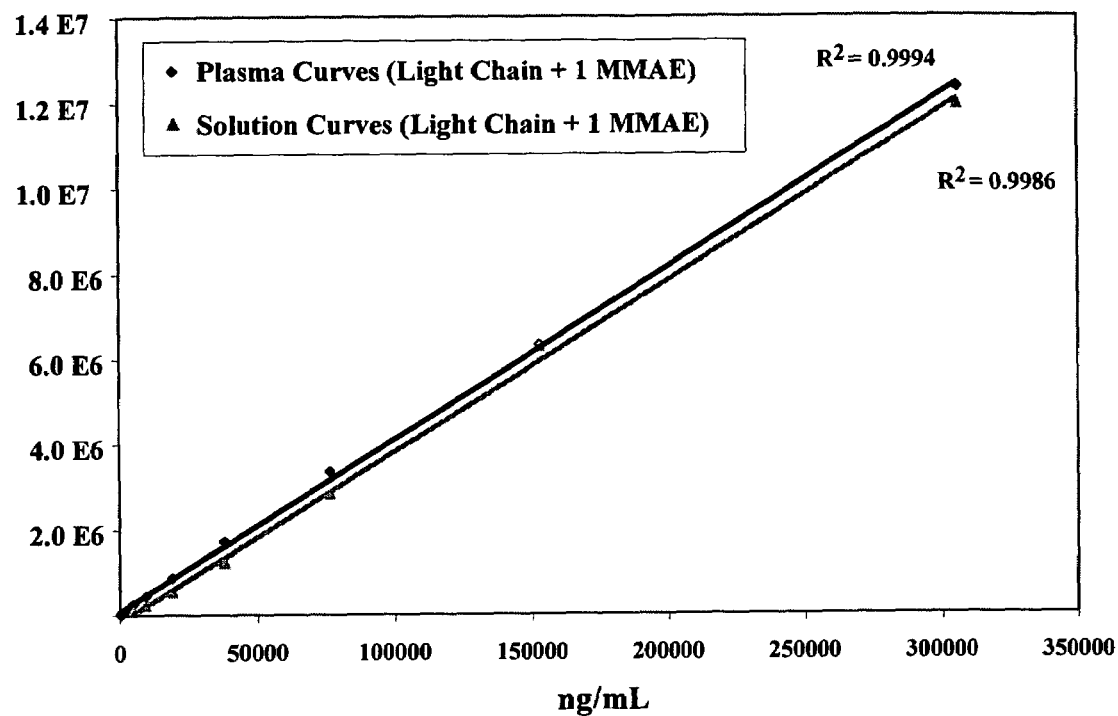
FIG. 17 shows LC/LC/MS calibration curves for plasma and solution samples of reduced trastuzumab light chain bearing one MMAE (LC+1 MMAE).

(23) ASLG659 (B7h, Genbank accession no. AX092328)
US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436)
Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B);
Accession: O43653; EMBL; AF043498; AAC39607.1.

(25) GEDA (Genbank accession No. AY260763);
AAP14954 lipoma HMGIC fusion-partner-like protein/pid=AAP14954.1—*Homo sapiens*
Species: *Homo sapiens* (human)
WO2003054152 (Claim 20); WO2003000842 (Claim 1); WO2003023013 (Example 3, Claim 20); US2003194704 (Claim 45);
Cross-references: GI:30102449; AAP14954.1; AY260763_1

(26) BAFF-R (B cell-activating factor receptor, BLyS receptor 3, BR3, Genbank accession No. NP_443177.1);
NP_443177 BAFF receptor/pid=NP_443177.1—*Homo sapiens* Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3);

Cross-references: MIM:606269; NP_443177.1; NM_052945_1

(27) CD22 (B-cell receptor CD22-B isoform, Genbank accession No. NP-001762.1);

Stamenkovic, I. and Seed, B., Nature 345 (6270), 74-77 (1990); US2003157113; US2003118592; WO2003062401 (Claim 9); WO2003072036 (Claim 1; FIG. 1); WO200278524 (Example 2);

Cross-references: MIM:107266; NP_001762. 1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation) PROTEIN SEQUENCE Full mpggpgv . . . dvqlekp (1 . . . 226; 226 aa), pI: 4.84, MW: 25028 TM: 2 [P] Gene Chromosome: 19q13.2, Genbank accession No. NP_001774.10)

WO2003088808, US20030228319; WO2003062401 (Claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) PROTEIN SEQUENCE Full mnypltl . . . atslttf (1 . . . 372; 372 aa), pI: 8.54 MW: 41959 TM: 7 [P] Gene Chromosome: 11q23.3, Genbank accession No. NP_001707.1)

WO2004040000; WO2004015426; US2003 105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+T lymphocytes) PROTEIN SEQUENCE Full mgsgwvp . . . vllpqsc (1 . . . 273; 273 aa, pI: 6.56 MW: 30820 TM: 1 [P] Gene Chromosome: 6p21.3, Genbank accession No. NP_002111.1)

Tonnelle et al (1985) EMBO J. 4(11):2839-2847; Jonsson et al (1989) Immunogenetics 29(6):411-413, Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) PROTEIN SEQUENCE Full mgqagck . . . lephrst (1 . . . 422; 422 aa), pI: 7.63, MW: 47206 TM: 1 [P] Gene Chromosome: 17p13.3, Genbank accession No. NP_002552.2)

Le et al (1997) FEBS Lett. 418(1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1)

WO2004042346 (Claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) PROTEIN SEQUENCE Full mafdvsc . . . rwkyqhi (1 . . . 661; 661 aa), pI: 6.20, MW: 74147 TM: 1 [P] Gene Chromosome: 5q12, Genbank accession No. NP_005573.1)

US2002193567; WO9707198 (claim 11, pages 39-42); Miura et al (1996) Genomics 38(3):299-304; Moira et al (1998) Blood 92:2815-2822; WO2003083047; WO9744452 (claim 8, pages 57-61); WO200012130 (pages 24-26);

(34) FCRH1 (Fc receptor-like protein 1, a putative receptor for the immunoglobulin Fc domain that contains C2 type Ig-like and ITAM domains, may have a role in B-lymphocyte differentiation) PROTEIN SEQUENCE Full mlprlll . . . vdyedam (1 . . . 429; 429 aa), pI: 5.28, MW: 46925 TM: 1 [P] Gene Chromosome: 1q21-1q22, Genbank accession No. NP_443170.1)

WO2003077836; WO200138490 (claim 6, FIG. 18E-1-18-E-2); Davis et al (2001) Proc. Natl. Acad. Sci USA 98(17): 9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies) PROTEIN SEQUENCE Full mllwvil . . . assaphr (1 . . . 977; 977 aa), pI: 6.88 MW: 106468 TM: 1 [P] Gene Chromosome: 1q21, Genbank accession No. NP_112571.1)

WO2003024392 (claim 2, FIG. 97); Nakayama et al (2000) Biochem. Biophys. Res. Commun. 277(1):124-127; WO2003077836; WO200138490 (claim 3, FIG. 18B-1-18B-2);

For other disclosure concerning tumor-associated antigens and specific antibodies thereto, see also: WO04/045516 (3 Jun. 2004); WO03/000113 (3 Jan. 2003); WO02/016429 (28 Feb. 2002); WO02/16581 (28 Feb. 2002); WO03/024392 (27 Mar. 2003); WO04/016225 (26 Feb. 2004); WO01/40309 (7 Jun. 2001), and U.S. Provisional patent application Ser. No. 60/520842 "COMPOSITIONS AND METHODS FOR THE TREATMENT OF TUMOR OF HEMATOPOIETIC ORIGIN", filed 17 Nov. 2003; all of which are incorporated herein by reference in their entirety.

Other exemplary antibodies and their abbreviations include: Herceptin® (trastuzumab)=full length, humanized antiHER2 (MW 145167), Herceptin F(ab')2=derived from antiHER2 enzymatically (MW 100000), 4D5=full-length, murine antiHER2, from hybridoma, rhu4D5=transiently expressed, full-length humanized antibody, rhuFab4D5=recombinant humanized Fab (MW 47738), 4D5Fc8=full-length, murine antiHER2, with mutated FcRn binding domain.

The antibody of the antibody-drug conjugates (ADC) of the invention may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. HERCEPTIN® (trastuzumab) selectively binds to the extracellular domain (ECD) of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens et al (1985) Science 230:1132-9; Slamon, et al (1989) Science 244:707-12). Trastuzumab is an IgG1 kappa antibody that contains human framework regions with the complementarity-determining regions (cdr) of a murine antibody (4D5) that binds to HER2. Trastuzumab binds to the HER2 antigen and thus inhibits the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831).

The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab). The antibody may be an antibody fragment, e.g. a Fab fragment.

Known antibodies for the treatment or prevention of cancer can be conjugated as ADC. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody for the treatment of patients with metastatic breast cancer; RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart M195 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 MAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Labelled Antibodies

The antibodies of the invention may be conjugated with any label moiety which can be covalently attached to the antibody through a reactive functional group, such as a cysteine thiol or lysine amino (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

The polypeptide variant may also be useful in diagnostic assays, e.g., for detecting expression of an antigen of interest in specific cells, tissues, or serum.

For diagnostic applications, the antibody will typically be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with reagents that include a radioisotope or which may complex a radioisotope where the reagent is reactive with the engineered cysteine thiol of the antibody, using the techniques described in *Current Protocols in Immunology*, Volumes 1 and 2, Coligen et al, Ed. Wiley-Interscience, New York, N.Y., Pubs. (1991).

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in *Current Protocols in Immunology*, supra, for example, and fluorescent label reagents from Molecular Probes (Eugene, Oreg.).

(c) Chelating reagents, such as DOTA or crown ethers which may complex metal ions (US 2002/0006379).

(d) Various enzyme-substrate labels are available or disclosed (U.S. Pat. No. 4,275,149). The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al, Methods for the Preparation of Enzyme-Antibody Conjugates for use in Enzyme Immunoassay, in *Methods in Enzym*. (ed J. Langone & H. Van Vunakis), Academic press, New York, 73:147-166 (1981).

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride(TMB));

(ii) alkaline phosphatase (AP) with para-nitrophenyl phosphate as chromogenic substrate; and (iii) β-D-galactosidase (β-D-Gal) with a chromogenic substrate (eg., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the polypeptide variant. The skilled artisan will be aware of various techniques for achieving this. For example, the polypeptide variant can be conjugated with biotin and any of the categories of labels mentioned above can be conjugated with avidin, or vice versa. Biotin binds selectively to avidin and thus, the label can be conjugated with the polypeptide variant in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in Bioconjugate Techniques Academic Press, San Diego).

The polypeptide variant of the present invention may be employed in any known assay method, such as competitive binding assays, direct and indirect sandwich assays, and immunoprecipitation assays (Zola, (1987) *Monoclonal Antibodies: A Manual of Techniques*, pp. 147-158, CRC Press, Inc.).

The polypeptide variant may also be used for in vivo diagnostic assays. Generally, the polypeptide variant is labeled with a radionuclide (such as $^{111}$In, $^{99}$Tc, $^{14}$C, $^{131}$I, $^{125}$I, $^{3}$H, $^{32}$P or $^{35}$S) so that the antigen or cells expressing it can be localized using immunoscintiography.

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels that are generally applicable for staining or labelling antibodies may have the following properties: (i) the labelled antibody should produce a high signal with low background so that small quantities of biopolymers can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death. Label moieties which provide a detectable signal include fluorescent dyes, chemiluminescent dyes (Briggs et al, "Synthesis of Functionalised Fluorescent Dyes and Their Coupling to Amines and Amino Acids," J. Chem. Soc., Perkin-Trans. 1:1051-1058 (1997).

Peptide labelling methods are well known. See Haugland, 2003, Molecular Probes Handbook of Fluorescent Probes and Research Chemicals, Molecular Probes, Inc.; Brinkley, 1992, Bioconjugate Chem. 3:2; Garman, 1997, "Non-Radioactive Labelling: A Practical Approach", Academic Press, London; Means (1990) Bioconjugate Chem. 1:2; Glazer etal (1975) "Chemical Modification of Proteins. Laboratory Techniques in Biochemistry and Molecular Biology" (T. S. Work and E. Work, Eds.) American Elsevier Publishing Co., New York; Lundblad, R. L. and Noyes, C. M. (1984) "Chemical Reagents for Protein Modification", Vols. I and II, CRC Press, New York; Pfleiderer, G. (1985) "Chemical Modification of Proteins, In Modern Methods in Protein Chemistry", H. Tschesche, Ed., Walter DeGryter, Berlin and New York; and Wong (1991) "Chemistry of Protein Conjugation and Crosslinking", CRC Press, Boca Raton, Fla.).

Peptides labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248: 18-34).

Labelling reagents typically bear reactive functionality which may react (i) directly with a reactive functional group, e.g. cysteine thiol, of an antibody to form the labelled antibody, (ii) with a linker reagent to form a linker label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH (N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT(1-(mesitylene-2-sulfonyl)-3-nitro-1H-1,2,4-triazole, and aryl sulfonyl halides, e.g. triisopropylbenzenesulfonyl chloride.

An exemplary antibody and tetramethylrhodamine (TAMRA) fluorescent dye conjugation is shown as:

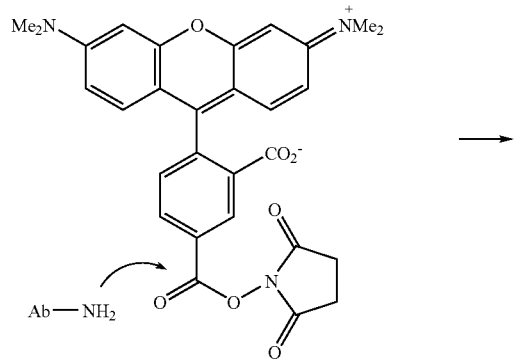

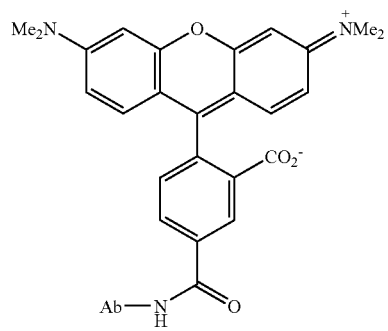

Figure 39:
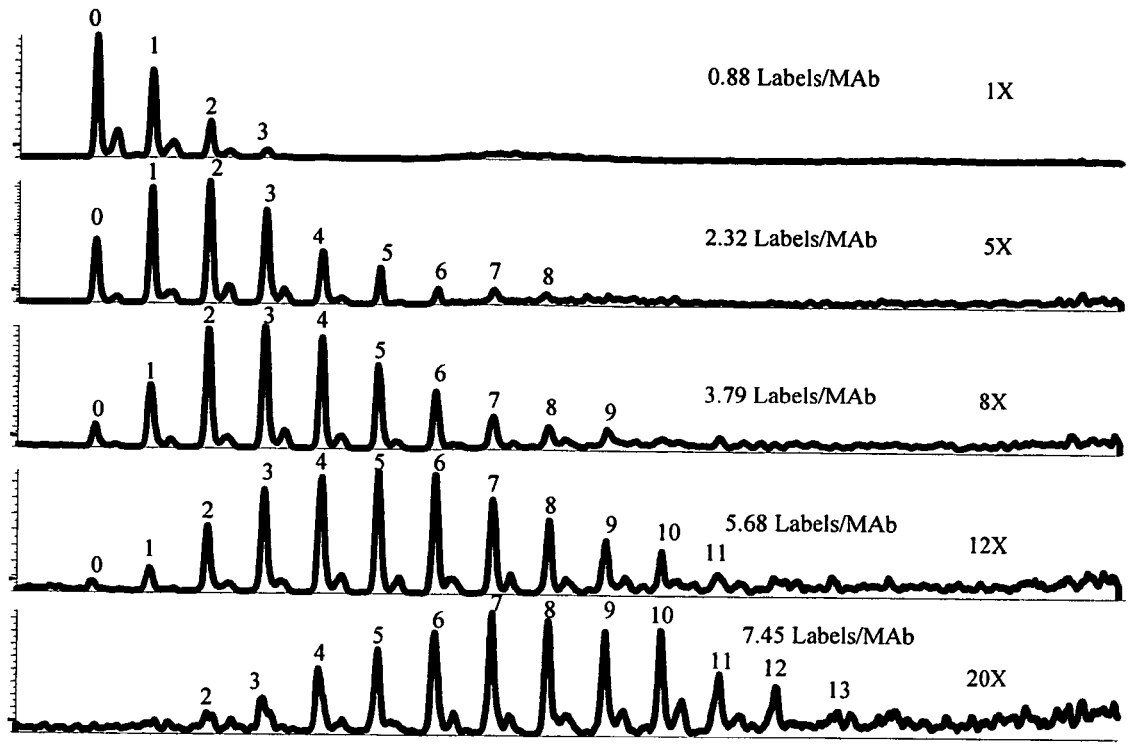
FIG. 39 shows LC analyses of five conjugation reactions of NHS ester of tetramethylrhodamine (TAMRA) to the antibody, 2H7, at molar excess of 1, 5, 8, 12, and 20 equivalents of TAMRA-NHS to antibody.

As shown, one or more reactive amino groups, e.g. lysine, of an antibody displaces the hydroxysuccinimide group of a NHS active ester of a fluorescent dye, such as TAMRA, resulting in the conjugation of one or more TAMRA dye moieties to the antibody. Certain fluorescent dyes in proximity to other fluorescent dyes may undergo self quenching. Self quenching effects are noted where the brightness (molecular extinction coefficient) as measured by fluorescence or UV absorbance is not linearly correlated to the number of dye moieties in the molecule. FIG. 8 shows a deconvolution spectra of a trastuzumab-rhodamine conjugate after deglycosylation. FIG. 9 shows the charged ions (m/z) prior to deconvolution of the spectra of trastuzumab-rhodamine conjugate after deglycosylation of FIG. 8, which are used for quantitation. The separation, detection, and quantitation methods of the invention can characterize dye loading and product distributions (FIG. 39) whereas fluorescence or UV spectroscopy cannot.

Drug Moieties

The drug moiety (D) of the Formula I antibody-drug conjugates (ADC) includes any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators. The drug moieties in the Formula I antibody-drug conjugates may have other mechanisms of action, and are not limited to any such mechanisms.

Exemplary drug moieties D in Formula I antibody-drug conjugate compounds are cytotoxic drugs, particularly those which are used for cancer therapy. Such drugs include, in general, DNA damaging agents, anti-metabolites, natural products and their analogs. Exemplary classes of cytotoxic agents include the enzyme inhibitors such as dihydrofolate reductase inhibitors, and thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, dolastatins, maytansinoids, differentiation inducers, and taxols.Exemplary drug moieties include, but are not limited to: methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, carminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, $N^8$-acetyl spermridine, camptothecin, calicheamicin, esperamicin, ene-diynes, and their derivatives and analogues.

The drug moiety (D) of the antibody drug conjugates (ADC) of Formula I include maytansinoids having the structure:

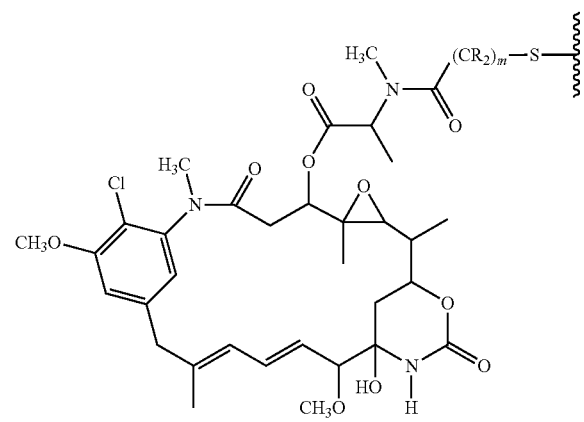

where the wavy line indicates the covalent attachment of the sulfur atom of D to a linker (L) of an antibody drug conjugate (ADC). R may independently be H or a $C_1$-$C_6$ alkyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005; U.S. Pat. No. 5,208,020). Maytansine was isolated from the east African shrub *Maytenus serrata* and shown to be 100-to 1000-fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al, (1978) J. Med. Chem. 21:31-37;Higashide et al. (1977) Nature 270:721-722; Kawai et al, (1984) Chem. Pharm. Bull. 32:3441-3451). Analogs of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4, 5. The naturally occurring and synthetic C-3 esters can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230 and 4,260,608; and Kawai et al, (1984) Chem. Pharm. Bull. 32:3441-3451). Esters of group (b) were found to be much more cytotoxic than esters of group (a).

Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al, (1978) Can. Treatment. Rev. 5:199-207).

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

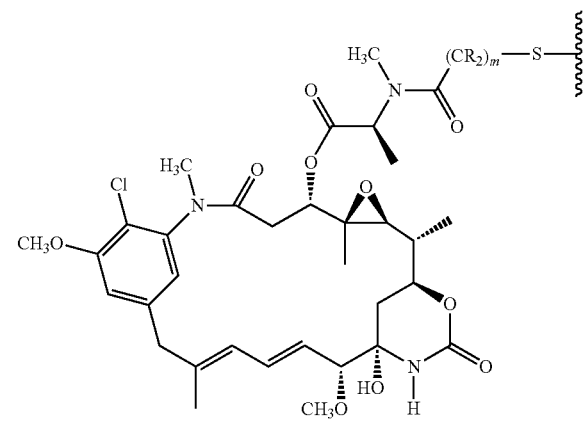

Exemplary embodiments of maytansinoid drug moieties include: DM1, $(CR_2)_m$=$CH_2CH_2$; DM3, $(CR_2)_m$=$CH_2CH_2CH(CH_3)$; and DM4, $(CR_2)_m$=$CH_2CH_2C(CH_3)_2$, having the structures:

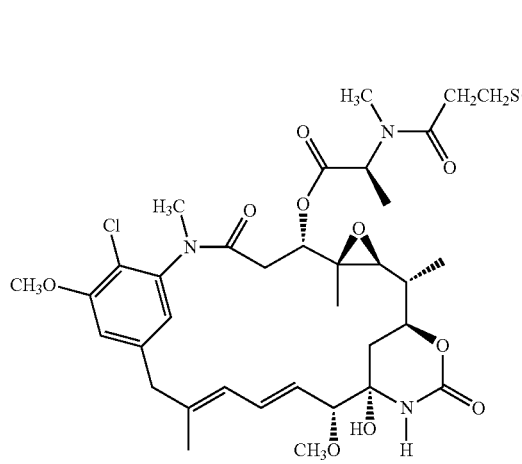

DM1

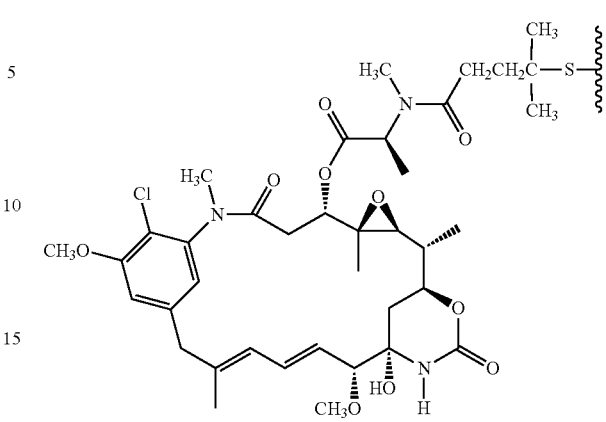

DM4

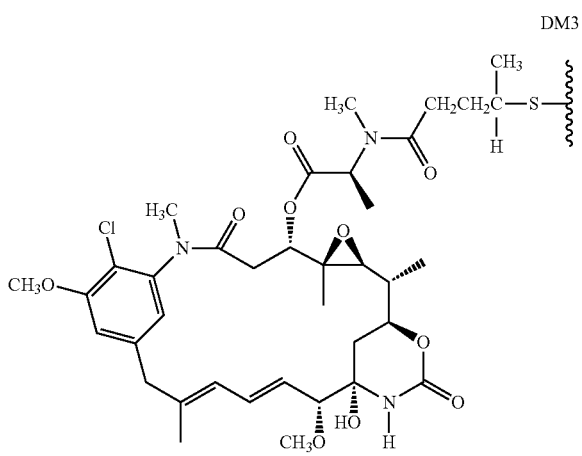

DM3

The drug moiety (D) of the-antibody drug conjugates (ADC) of Formula I also include dolastatins and their peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172). Variants of auristatin E are disclosed in U.S. Pat. No. 5,767,237; U.S. Pat. No. 6,124,431.

Embodiments of drug moiety (D) of the antibody-drug conjugates (ADC) of Formula I include the N-terminus linked monomethylauristatin drug moieties $D_E$ and $D_F$, disclosed in "Monomethylvaline Compounds Capable of Conjugation to Ligands", U.S. Ser. No. 10/983,340, filed Nov. 5, 2004, and having the structures:

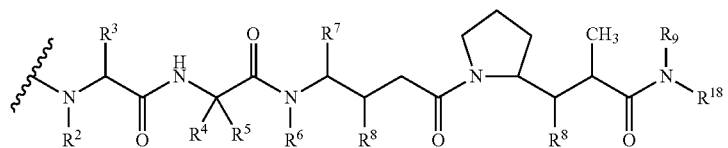

$D_E$

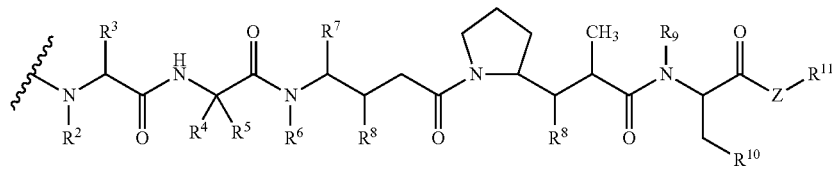

$D_F$ wherein the wavy line of $D_E$ and $D_F$ indicates the covalent attachment site to A, W, or Y of the Linker, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, $C_6$-$C_{20}$ aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, $C_6$-$C_{20}$ aryl, $C_1$-$C_8$ alkyl-($C_6$-$C_{20}$ aryl), $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from $C_6$-$C_{20}$ aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$—($C_6$-$C_{20}$ aryl), —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

An exemplary embodiment of drug moiety $D_E$ is MMAE:

MMAE and MMAF immunoconjugates are disclosed in Senter et al, Proceedings of the American Association for Cancer Research, Volume 45, Abstract Number 623, presented Mar. 28, 2004.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. *Synthesis*, 1996, 719-725; and Pettit et al (1996) J. Chem. Soc. Perkin Trans. 15:859-863.

Another useful class of drug moiety for Formula I compounds is the ene-diyne family of calicheamicins (U.S. Pat. No. 5,053,394; U.S. Pat. No. 4,970,198; U.S. Pat. No. 5,079,233; U.S. Pat. No. 5,773,001; U.S. Pat. No. 5,606,040; U.S. Pat. No. 5,739,116; U.S. Pat. No. 5,264,586; U.S. Pat. No. 5,384,412) and esperamicins (U.S. Pat. No. 5,877,296).

Linkers

A "Linker" (L) is a bifunctional or multifunctional moiety which can be used to link one or more Drug moieties (D) and an antibody unit (Ab) to form antibody drug conjugates (ADC) of Formula I. Antibody drug conjugates (ADC) can be conveniently prepared using a Linker having reactive functionality for binding to the Drug and to the Antibody. Various functional groups of an antibody (Ab), including a cysteine thiol, a lysine amino, an aspartic acid carboxylic acid, or a sugar hydroxyl group, can form a bond with a functional group of a drug moiety or drug-linker reagent.

In one aspect, a Linker has an electrophilic group that is reactive with a nucleophilic group, such as cysteine, present on an antibody. For example, a cysteine thiol of the antibody is reactive with an electrophilic group on a Linker and forms a covalent bond to a Linker. Useful electrophilic groups include, but are not limited to, maleimide and haloacetamide

MMAE

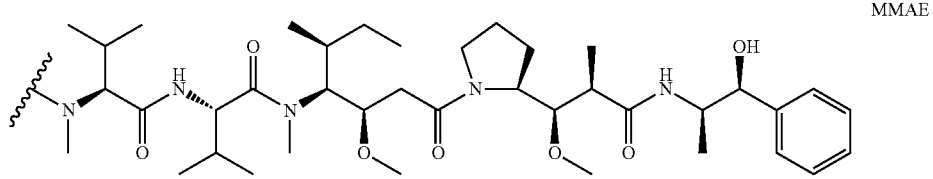

An exemplary embodiment of drug moiety $D_F$ is MMAF:

MMAF

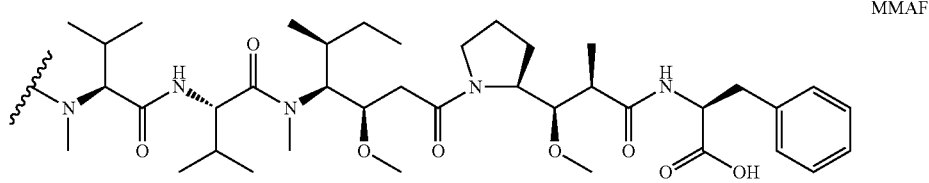

groups. Cysteine thiols of antibodies may react with electrophilic functional groups such as maleimide or α-halo carbonyl, of drug moiety-linkers, or linker reagents, according to the conjugation method at page 766 of Klussman, et al (2004), Bioconjugate Chemistry 15(4):765-773, and according to the protocol of Example 4.

In one embodiment, linker L of an ADC has the formula:

-A$_a$-W$_w$—Y$_y$— wherein:

A is a Stretcher unit covalently attached to a cysteine thiol of the antibody (Ab);

a is 0 or 1;

each W is independently an Amino Acid unit;

w is independently an integer ranging from 0 to 12;

Y is a Spacer unit covalently attached to the drug moiety; and y is 0, 1 or 2.

Exemplary embodiments include where D is a Drug unit (moiety) having a nitrogen atom that can form a bond with the Spacer unit when y is 1 or 2, with the C-terminal carboxyl group of an Amino Acid unit when y is 0, with the carboxyl group of a Stretcher unit when w and y are each 0, and with the carboxyl group of a Drug unit when a, w, and y are each 0. It is to be understood that the terms "drug unit" and "drug moiety" are synonymous and used interchangeably herein.

Stretcher Unit

The Stretcher unit (A), when present, is capable of linking an antibody unit to an amino acid unit (W). In this regard an antibody (Ab) has a free cysteine thiol group that can form a bond with an electrophilic functional group of a Stretcher Unit. Representative Stretcher units of this embodiment are depicted within the square brackets of Formulas IIIa and IIIb, wherein Ab, W, Y, D, w and y are as defined above, and R$^{17}$ is a divalent radical selected from (CH$_2$)$_r$, C$_3$-C$_8$ carbocyclyl, O—(CH$_2$)$_r$, aryl, (CH$_2$)$_r$-aryl, -aryl-(CH$_2$)$_r$—, (CH$_2$)$_r$—(C$_3$-C$_8$ carbocyclyl), (C$_3$-C$_8$ carbocyclyl)-(CH$_2$)$_r$, C$_3$-C$_8$ heterocyclyl, (CH$_2$)$_r$—(C$_3$-C$_8$ heterocyclyl), —(C$_3$-C$_8$ heterocyclyl)-(CH$_2$)$_r$—, —(CH$_2$)$_r$C(O)NR$^b$(CH$_2$)$_r$—, —(CH$_2$CH$_2$O)$_r$—, —(CH$_2$CH$_2$O)$_r$—CH$_2$—, —(CH$_2$)$_r$C(O)NR$^b$(CH$_2$CH$_2$O)$_r$—, —(CH$_2$)$_r$C(O)NR$^b$(CH$_2$CH$_2$O)$_r$—CH$_2$—, —(CH$_2$CH$_2$O)$_r$C(O)NR$^b$(CH$_2$CH$_2$O)$_r$—, —(CH$_2$CH$_2$O)$_r$C(O)NR$^b$(CH$_2$CH$_2$O)$_r$—CH$_2$—, and —(CH$_2$CH$_2$O)$_r$C(O)NR$^b$(CH$_2$)$_r$—; where r is independently an integer ranging from 1-10.

It is to be understood from all the exemplary embodiments of Formula I ADC such as III-VI, that even where not denoted expressly, from 1 to 4 drug moieties are linked to an antibody (p=1-4).

IIIa

Ab—S—[structure with N—R$^{17}$—C(O)—W$_w$—Y$_y$—D]$_p$

IIIb

Ab—S—(CH$_2$—CONH—R$^{17}$—C(O)—W$_w$—Y$_y$—D)$_p$

An illustrative Stretcher unit is that of Formula IIIa, and is derived from maleimido-caproyl (MC) wherein R$^{17}$ is —(CH$_2$)$_5$—:

MC

An illustrative Stretcher unit is that of Formula IIIa, and is derived from maleimido-propanoyl (MP) wherein R$^{17}$ is —(CH$_2$)$_2$—:

MP

Another illustrative Stretcher unit is that of Formula IIIa wherein R$^{17}$ is —(CH$_2$CH$_2$O)$_r$—CH$_2$— and r is Another illustrative Stretcher unit is that of Formula IIIa wherein R$^{17}$ is —(CH$_2$)$_r$C(O)NR$^b$(CH$_2$CH$_2$O)$_r$—CH$_2$— where R$^b$ is H and each r is 2:

MPEG

Another illustrative Stretcher unit is that of Formula IIIb wherein R$^{17}$ is —(CH$_2$)$_5$—:

In another embodiment, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, Ab-, —W—, —Y—, -D, w and y are as defined above.

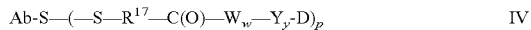

Ab-S—(—S—$R^{17}$—C(O)—$W_w$—$Y_y$-D$)_p$   IV

In yet another embodiment, the reactive group of the Stretcher contains a thiol-reactive functional group that can form a bond with a free cysteine thiol of an antibody. Examples of thiol-reactive functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, Ab-, —W—, —Y—, -D, w and y are as defined above;

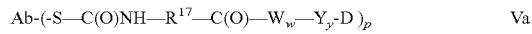

Ab-(-S—C(O)NH—$R^{17}$—C(O)—$W_w$—$Y_y$-D$)_p$   Va

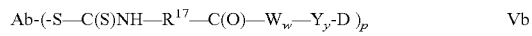

Ab-(-S—C(S)NH—$R^{17}$—C(O)—$W_w$—$Y_y$-D$)_p$   Vb

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

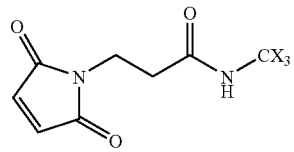 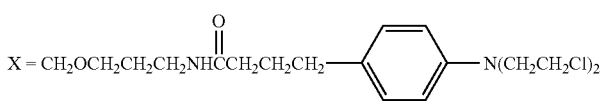

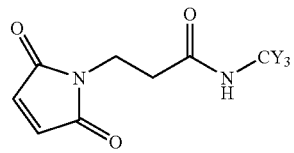 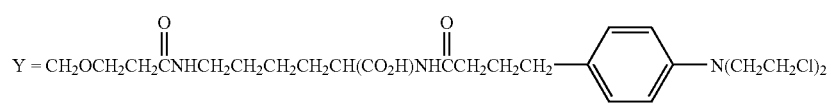

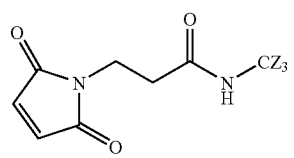 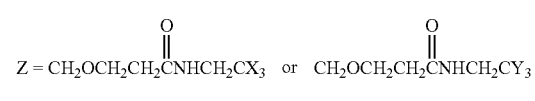

Amino Acid Unit

The linker may comprise amino acid residues. The Amino Acid unit (—$W_w$—), when present, links the antibody (Ab) to the drug moiety (D) in an antibody-drug conjugate (ADC) of the invention.

Amino acid unit —$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

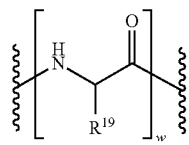

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC$ (=NH)$NH_2$, —$(CH_2)_3NH_2$, —$(CH_2)_3NHCOCH_3$, —$(CH_2)_3$ NHCHO, —$(CH_2)_4NHC$(=NH)$NH_2$, —$(CH_2)_4$ $NH_2$, —$(CH_2)_4NHCOCH_3$, —$(CH_2)_4NHCHO$, —$(CH_2)_3$ $NHCONH_2$, —$(CH_2)_4NHCONH_2$, —$CH_2CH_2CH(OH)$ $CH_2NH_2$, 2-pyridylmethyl-, 3-pyridylmethyl-, 4-pyridylmethyl-, phenyl, cyclohexyl,

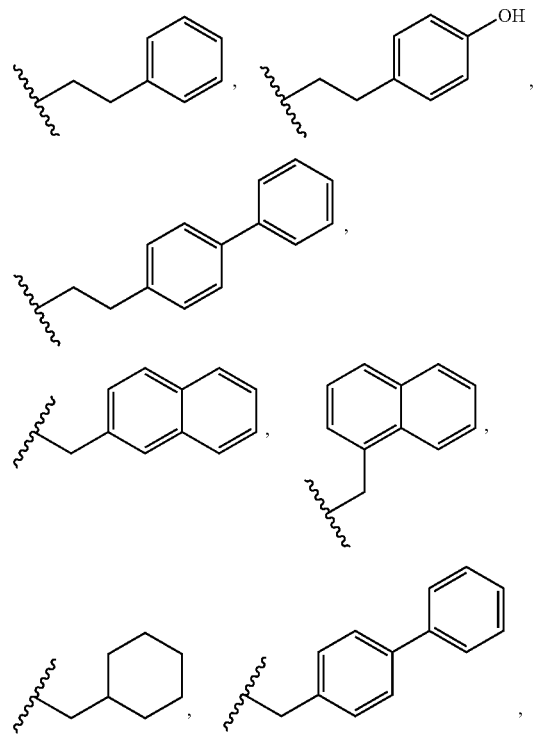

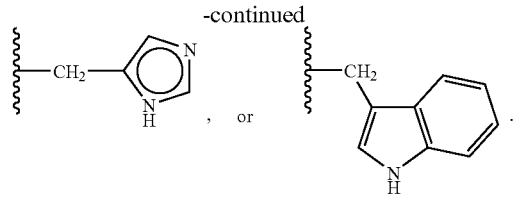

When $R^{19}$ is other than hydrogen, the carbon atom to which $R^{19}$ is attached is chiral. Each carbon atom to which $R^{19}$ is attached independently in the (S) or (R) configuration, or a racemic mixture. Amino acid units may thus be enantiomerically pure, racemic, or diastereomeric.

In exemplary embodiments, w may be 1, 2 or 3, to form single amino acid, dipeptide, and tripeptide amino acid units, respectively. Amino acid units W are selected from natural and non-natural amino acids. The side chain-bearing carbon may be in either D or L (R or S) configuration. Amino acid unit Z may be alanine, 2-amino-2-cyclohexylacetic acid, 2-amino-2-phenylacetic acid, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, γ-aminobutyric acid, α,α-dimethyl γ-aminobutyric acid, β,β-dimethyl γ-aminobutyric acid, ornithine, and citrulline (Cit). Amino acid unit Z optionally includes protected forms of amino acids where reactive functionality of the side chains are protected. Protected amino acid reagents and intermediates are well known, including lysine-protected with acetyl, formyl, triphenylmethyl (trityl), and monomethoxytrityl (MMT). Other protected amino acid units include arginine-protected tosyl or nitro group, ornithine-protected with acetyl or formyl groups.

The Amino Acid unit can be enzymatically cleaved by one or more enzymes, including a tumor-associated protease, to liberate the Drug moiety (-D), which in one embodiment is protonated in vivo upon release to provide a Drug (D). Useful —$W_w$— units can be designed and optimized in their selectivity for enzymatic cleavage by a particular enzymes, such as cathepsin B, C and D, or a plasmin protease.

Exemplary —$W_w$—Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly).

Spacer Unit

The Spacer unit (—$Y_y$—), when present (y=1 or 2), links an Amino Acid unit (—$W_v$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-

Ww-. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit (see Schemes 2 and 3) whose phenylene portion is substituted with $Q_m$ wherein Q is —$C_1$-$C_8$ alkyl, —O—($C_1$-$C_8$ alkyl), -halogen,-nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB (para-aminobenzyloxycarbonyl) group that is linked to —$W_w$— via the amino nitrogen atom of the PAB group, and connected directly to -D via a carbonate, carbamate or ether group, where the ADC has exemplary formula X:

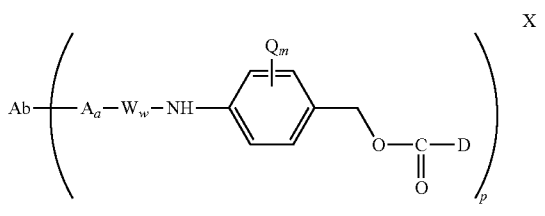

wherein Q is —$C_1$-$C_8$ alkyl, —O—($C_1$-$C_8$ alkyl), -halogen, -nitro or -cyano; m is an integer ranging from 0-4; and p ranges from 1 to 4.

Self-immolative spacers include, but are not limited to, PAB (Carl et al (1981) J. Med. Chem. 24:479-480; Chakravarty et al (1983) J. Med. Chem. 26:638-644; U.S. Pat. No. 6,214,345), aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al, (1995) Chemistry Biology, 2:223), appropriately substituted bicyclo[2.2.1] and bicyclo[2.2.2] ring systems (Storm, et al, (1972) J. Amer. Chem. Soc., 94:5815) and 2-aminophenylpropionic acid amides (Amsberry, et al, (1990) J. Org. Chem., 55:5867). Elimination of amine-containing drugs that are substituted at glycine (Kingsbury, et al, (1984) J. Med. Chem., 27:1447) are also examples of self-immolative spacer useful in ADCs.

Spacer units (—$Y_y$—) also include represented by Formulas XI and XII:

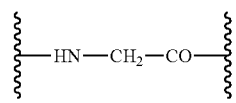

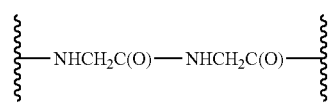

Embodiments of the Formula I antibody-drug conjugate compounds include XIIIa (val-cit), XIIIb (MC-val-cit), XIIIc (MC-val-cit-PAB):

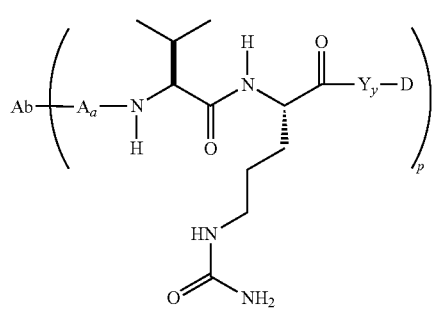

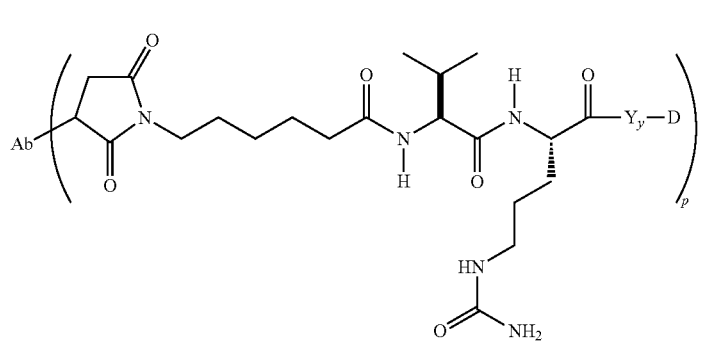

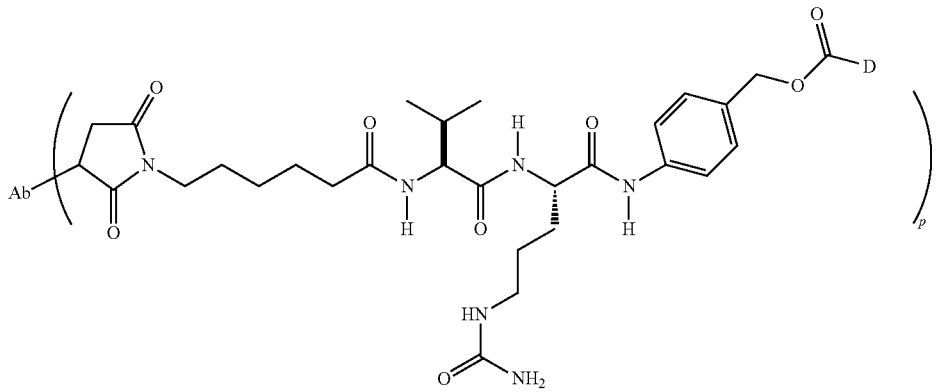
XIIIc

Other exemplary embodiments of the Formula Ia antibody-drug conjugate compounds include XIVa-e:

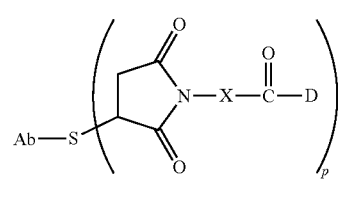
XIVa

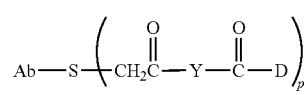
XIVb

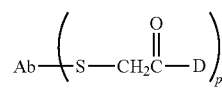
XIVc

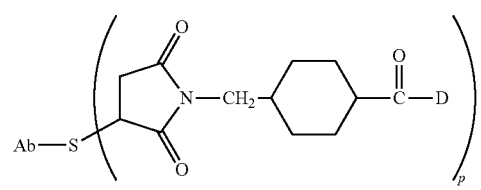
XIVd

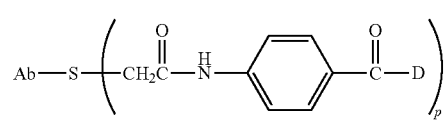
XIVe where X is:

—CH$_2$—⌬—  , —(CH$_2$)$_n$—  ,

—(CH$_2$CH$_2$O)$_n$—  ,

—CH$_2$—⌬—C(O)—N(R)—(CH$_2$)$_n$—  ,

⌬  , ⌬—(CH$_2$)$_n$—  , or

—(CH$_2$)$_n$—C(O)—N(R)—(CH$_2$)$_n$—  ;

Y is: —N(R)—⌬—  or  —N(R)—(CH$_2$)$_n$—  ;

and R is independently H or $C_1$-$C_6$ alkyl; and n is 1 to 12.

Antibody Drug Conjugates

Exemplary embodiments of Formula I ADC have the following structures and abbreviations:

Ab-MC-vc-PAB-MMAF

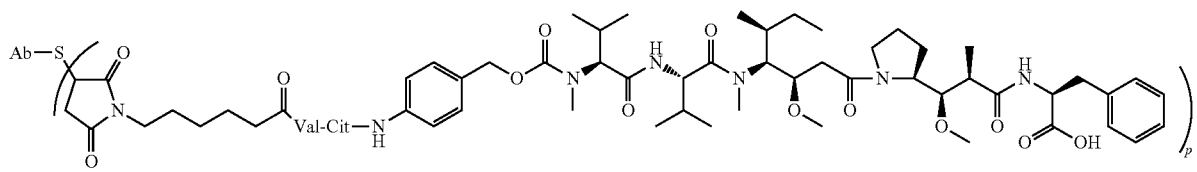

Ab-MC-vc-PAB-MMAE
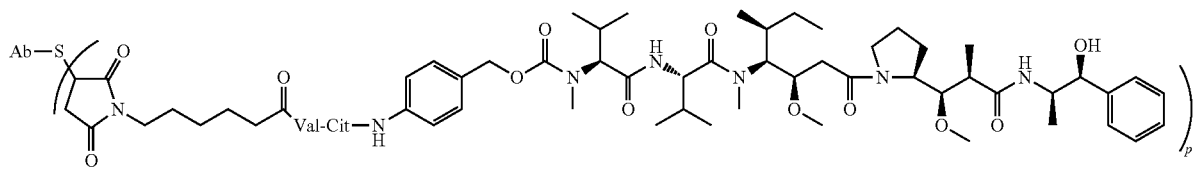
Ab-MC-MMAE
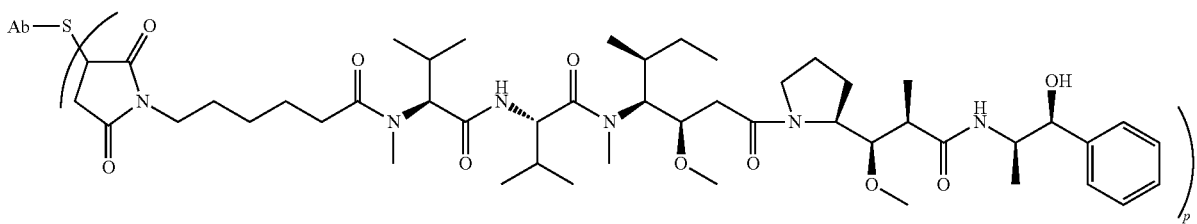
Ab-MC-MMAF
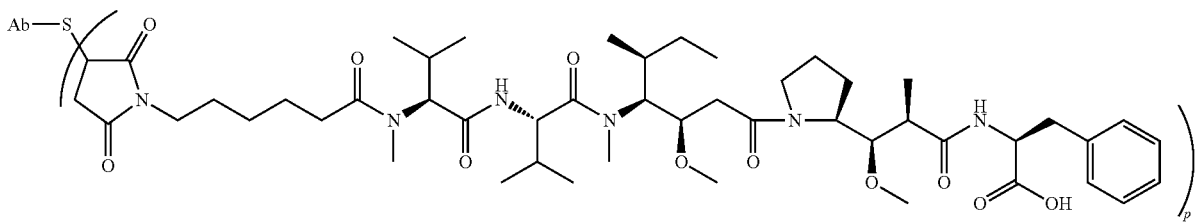
Other exemplary antibody-drug conjugates have structures, where an antibody, e.g. trastrzumab (Tr), is linked through an amino group to a linker, and p is 1 to about 8:
trastuzumab-SPP-DM1
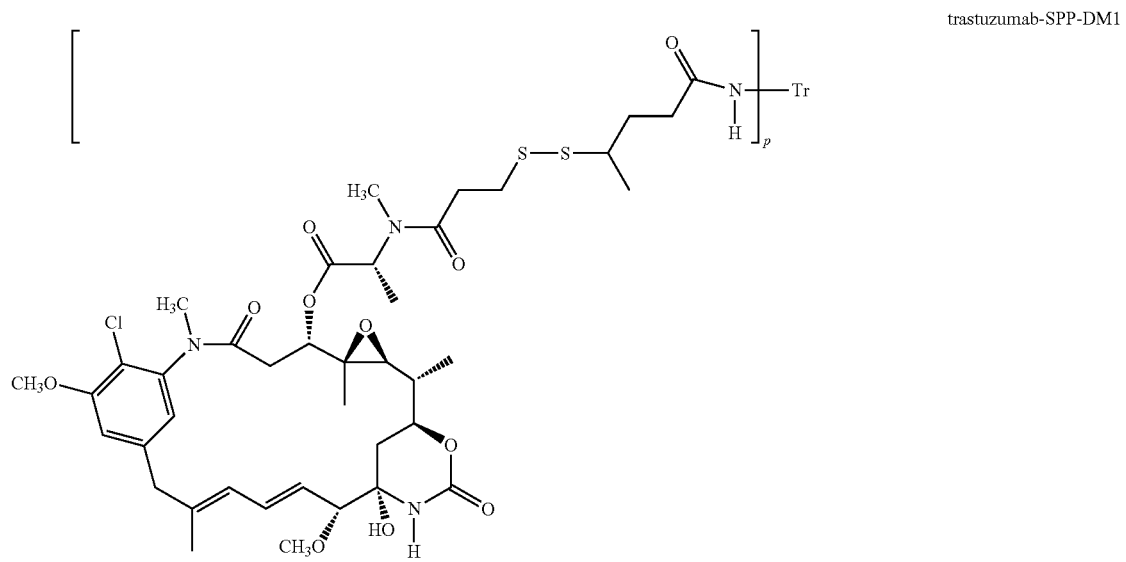

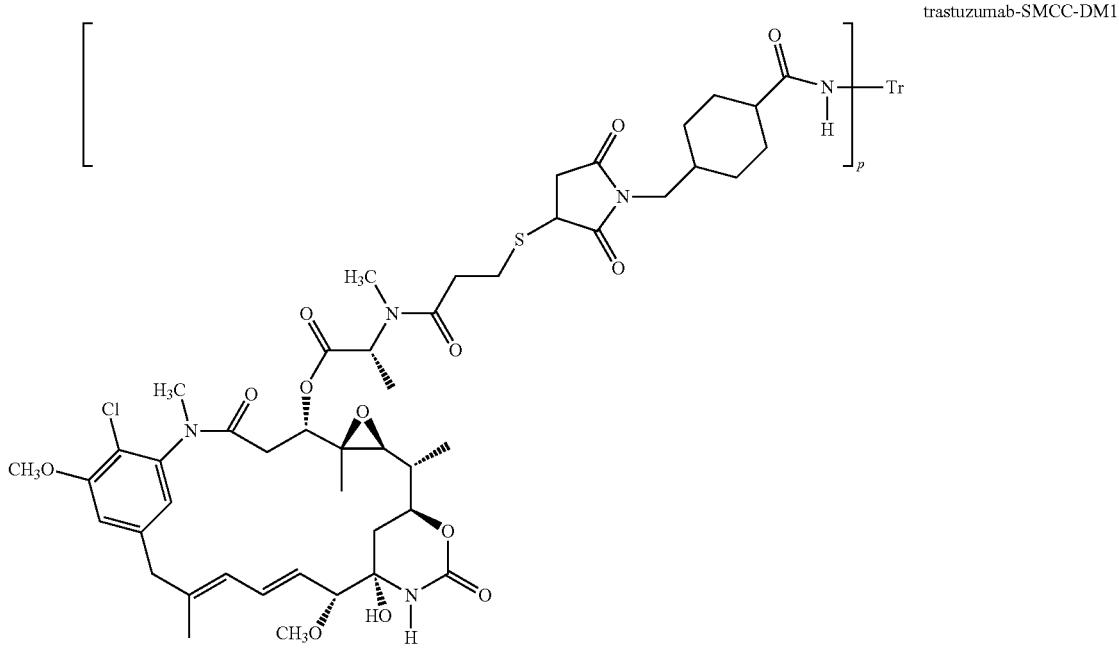

Exemplary antibody drug conjugates where DM1 is linked through a BMPEO linker to a thiol group of trastuzumab have the structure:

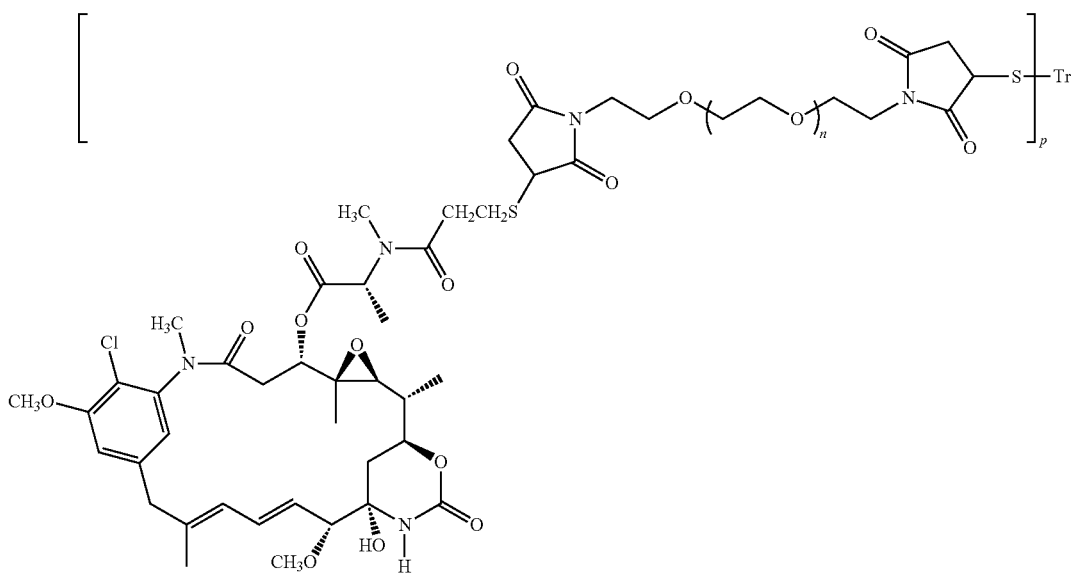

where Tr is trastuzumab; n is 0, 1, or 2; and p is 1, 2, 3, 4, 5, 6, 7 or 8.

The Antibody Drug Conjugates (ADC) of Formula I can be made using the synthetic procedures outlined below. ADC can be conveniently prepared using a linker reagent or drug-linker reagent having reactive functionality for binding to the Drug and to the Antibody. In one aspect, a linker reagent has an electrophilic group that is reactive with a nucleophilic group present on an antibody. Useful nucleophilic groups on an antibody include but are not limited to, sullhydryl, hydroxyl and amino groups. The heteroatom of the nucleophilic group of an antibody is reactive to an electrophilic group on a linker reagent and forms a covalent bond to a linker. Useful electrophilic groups include, but are not limited to, maleimide and haloacetamide groups. The electrophilic group provides a convenient site for Antibody attachment.

In another embodiment, a linker reagent or drug-linker reagent has a reactive nucleophilic functional group which is reactive with an electrophile present on an antibody to form a covalent bond. Useful electrophilic groups on an antibody include, but are not limited to, aldehyde and ketone carbonyl groups. Useful nucleophilic groups on a linker include, but are not limited to, hydrazide, oxime, amino, hydrazine, thiosemicarbazone, hydrazine carboxylate, and arylhydrazide. The electrophilic group on an antibody provides a convenient site for attachment to a linker.

Carboxylic acid functional groups and chloroformate functional groups are also useful reactive sites for a linker because they can react with secondary amino groups of a Drug to form an amide linkage. Also useful as a reactive site is a carbonate functional group on a linker, such as but not limited to p-nitrophenyl carbonate, which can react with an amino group of a Drug, such as but not limited to N-methyl valine, to form a carbamate linkage. Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, (1965) "The Peptides", volume 1, pp 76-136, Academic Press) that is well known in the field of peptide chemistry.

An antibody unit can form a bond to either a linker, a Stretcher unit, an Amino Acid unit, a Spacer Unit, or a Drug moiety directly. An antibody unit can form a bond to a linker unit via a heteroatom of the antibody. Heteroatoms that may be present on an antibody unit include sulfur (in one embodiment, from a sulfhydryl group of an antibody), oxygen (in one embodiment, from a carbonyl, carboxyl or hydroxyl group of an antibody) and nitrogen (in one embodiment, from a primary or secondary amino group of an antibody). These heteroatoms can be present on the antibody in the antibody's natural state, for example a naturally occurring antibody, or can be introduced into the antibody via chemical modification.

In one embodiment, the antibody has one or more lysine residues that can be chemically modified to introduce one or more sulfhydryl groups. The antibody unit bonds to the Linker unit via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the antibody can have one or more carbohydrate groups that can be chemically modified to have one or more sulfhydryl groups. The antibody unit bonds to the linker, such as the Stretcher Unit, via the sulfhydryl group's sulfur atom.

In yet another embodiment, the antibody can have one or more carbohydrate groups that can be oxidized to provide an aldehyde (—CHO) group (see for example, Laguzza, et al (1989) J. Med. Chem. 32(3):548-55). The corresponding aldehyde can form a bond with a Reactive Site on a Stretcher. Reactive sites on a Stretcher that can react with a carbonyl group on an antibody include, but are not limited to, hydrazine and hydroxylamine. Other protocols for the modification of proteins for the attachment or association of Drug Units are described in Coligan et al, "Current Protocols in Protein Science", vol. 2, John Wiley & Sons (2002), incorporated herein by reference.

Typically, peptide-type linkers can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, (1965), Academic Press) that is well known in the field of peptide chemistry.

In another embodiment, the linker may be substituted with groups which modulated solubility or reactivity. For example, a charged substituent such as sulfonate (—$SO_3^-$) or ammonium, may increase water solubility of the reagent and facilitate the coupling reaction of the linker reagent with the antibody or the drug moiety, or facilitate the coupling reaction of Ab-L (antibody-linker) with D, or D-L (drug linker reagent) with Ab, depending on the synthetic route employed to prepare the ADC.

The compounds of the invention expressly contemplate, but are not limited to, ADC prepared with cross-linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 USA, 1-800-874-3723, International +815-968-0747. See pages 467-498, 2003-2004 of the Applications Handbook and Catalog. Bis-maleimide reagents allow the attachment of the thiol group of a cysteine residue of an antibody to a thiol-containing drug moiety, label, or linker intermediate, in a sequential or concurrent fashion. Other functional groups besides maleimide, which are reactive with a thiol group of an antibody, drug moiety, label, or linker intermediate include iodoacetamide, bromoacetamide, vinyl pyridine, disulfide, pyridyl disulfide, isocyanate, and isothiocyanate.

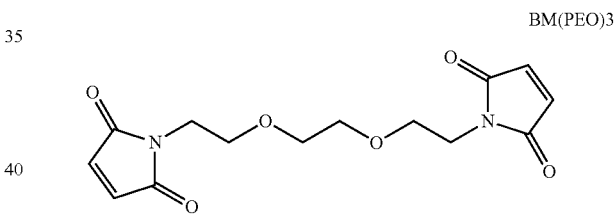

BM(PEO)3

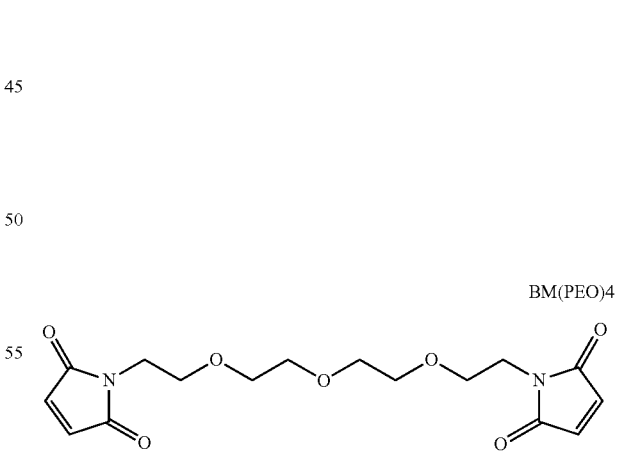

BM(PEO)4

Useful linker reagents can also be obtained via other commercial sources, such as Molecular Biosciences Inc.(Boulder, Colo.), or synthesized in accordance with procedures described in Toki et al (2002) J. Org. Chem. 67:1866-1872; U.S. Pat. No. 6,214,345 to Firestone et al; WO 02/088172; US 2003130189; US2003096743; WO 03/026577; WO 03/043583; and WO 04/032828.

An exemplary valine-citrulline (val-cit or vc) dipeptide linker reagent having a maleimide Stretcher Unit and a para-aminobenzyloxycarbonyl (PAB) self-immolative Spacer Unit has the structure:

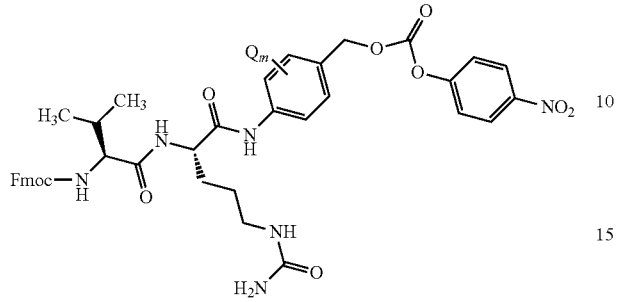

where Q is —$C_1$-$C_8$ alkyl, —O—($C_1$-$C_8$ alkyl), -halogen, -nitro or -cyano; and m is an integer ranging from 0-4.

An exemplary phe-lys(Mtr) dipeptide linker reagent having a maleimide Stretcher unit and a PAB Spacer unit can be prepared according to Dubowchik, et al. (1997) Tetrahedron Letters, 38:5257-60, and has the structure:

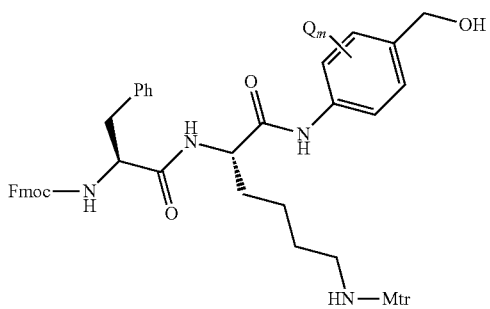

where Mtr is mono-4-methoxytrityl, Q is —$C_1$-$C_8$ alkyl, —O—($C_1$-$C_8$ alkyl), -halogen, -nitro or -cyano; and m is an integer ranging from 0-4.

Exemplary drug-linker reagents include: Maleimidocaproyl-valine-citrulline-p-hydroxymethylaminobenzyloxycarbonyl-MMAF (MC-val-cit-PAB-MMAF):

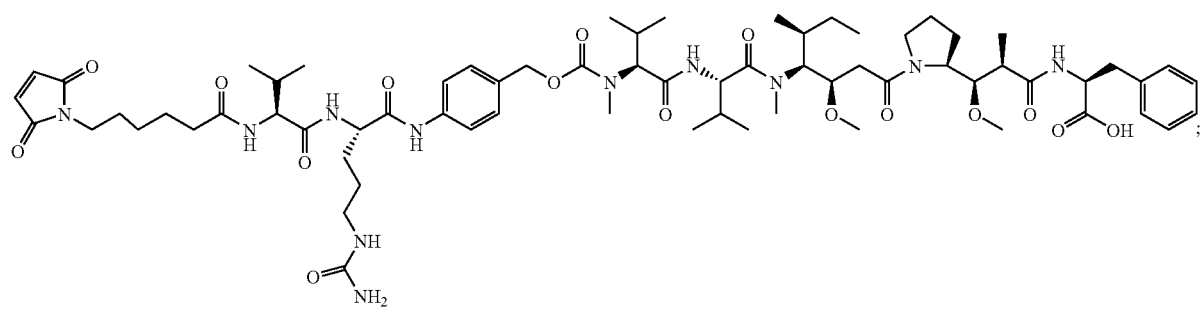

Maleimidocaproyl-valine-citrulline-p-hydroxymethylaminobenzyloxycarbonyl-MMAE (MC-val-cit-PAB-MMAE):

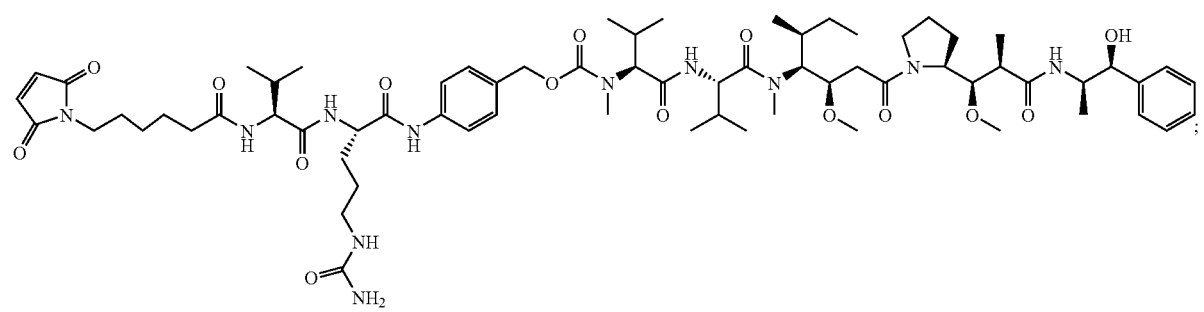

Maleimidocaproyl-MMAF (MC-MMAF):

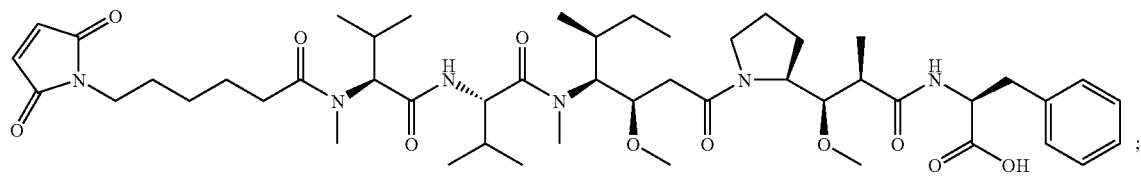

Maleimidocaproyl-MMAE (MC-MMAE):

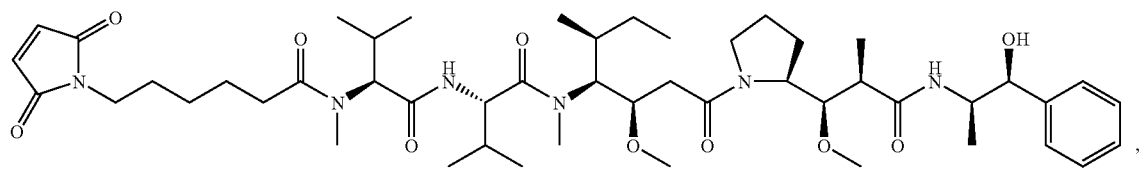

and can be prepared according to: Doronina et al (2003) Nature Biotechnology 21(7):778-784; Francisco et al (2003) Blood 102:1458-1465; and "Monomethylvaline Compounds Capable of Conjugation to Ligands", U.S. Ser. No. 10/983,340, filed Nov. 5, 2004.

Antibody-drug conjugate compounds may be synthesized by reducing the interchain disulfide bonds of the antibody followed by conjugation of the maleimide drugs to cysteine thiol groups of the reduced antibody via thioether linkages. As a result, these antibody conjugates are held together by non-covalent van der Waal's interactions and will separate into light and heavy chains after disulfide bond reduction, and under denaturing conditions (reverse phase chromatography). Antibodies which are conjugated through amino groups, such as lysine residues, do not necessitate reduction and cleavage of interchain disulfide bonds.

Figure 15:
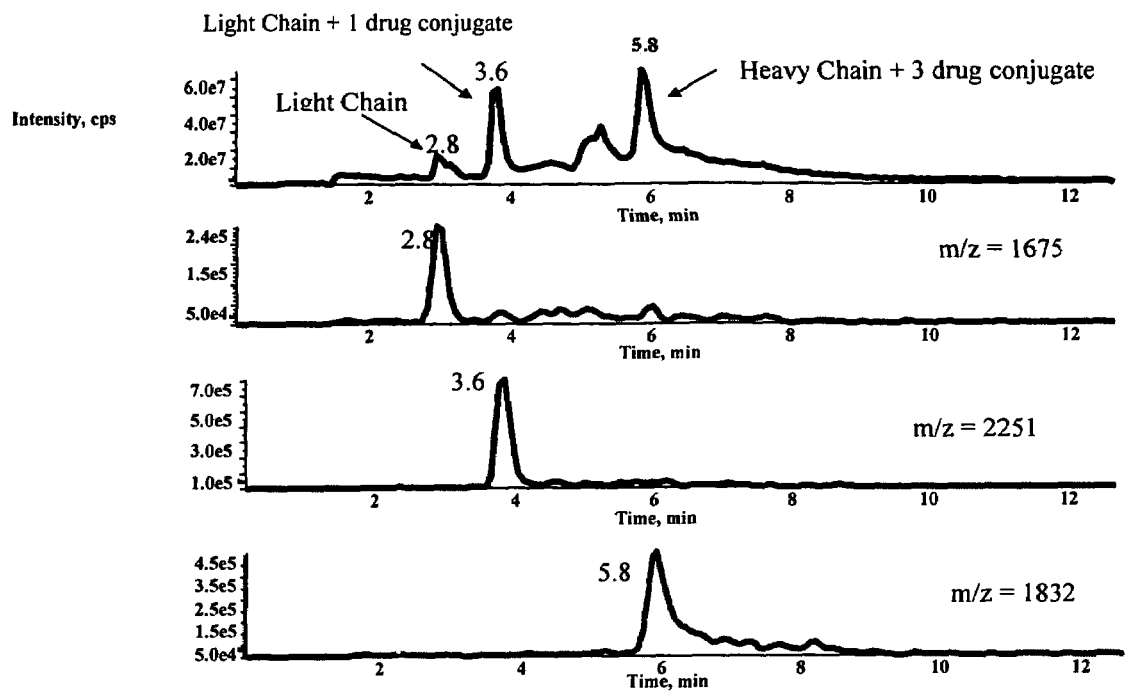
FIG. 15 shows chromatograms of: (top) trastuzumab-MC-vc-PAB-MMAE; and individual ions extracted from the total ion chromatogram: light chain, m/z=1675 (second from top); light chain with one MMAE, m/z=2251 (third from top); and heavy chain with three MMAE, m/z=1832 (bottom).

The antibody conjugates were initially characterized by coupling a reverse phase HPLC method to (PLRP-S 2.0×50 mm, 8 μm, 1000 Å column) an API 3000 mass spectrometer. FIG. 15 shows chromatograms of: (top) trastuzumab-MC-vc-PAB-MMAE; and chromatographically isolated fragments after reduction and denaturation: light chain, m/z=1675 (second from top); light chain with one MMAE, m/z=2251 (third from top); and heavy chain with three MMAE, m/z=1832 (bottom)(Kadkhodayan, M. and Mann, E. "New Strategies in Characterization and Quantitation of Antibody-targeted Drug Conjugates in Plasma using LC/LC/MS", 51st Conference on Mass Spectrometry and Allied Topics, American Society for Mass Spectrometry, Montréal, Québec, Jun. 8-12, 2003).

Drug Loading

The drug loading value is represented by p, the average number of drug moieties per antibody in a molecule of Formula I. Compositions of ADC of Formula I include collections, i.e. mixtures, of antibodies conjugated with a range of drugs, from 1 to about 8. Each preparation of an ADC by conjugation of an antibody to a drug moiety results in a potential distribution of product molecules, bearing one or more drugs bound to antibody, or where the antibody has not been linked to a drug moiety, where p=0. The average number of drugs per antibody in preparations of ADC from conjugation reactions may be characterized by the methods of the present invention, i.e. LC/MS. The average number of drug per antibody in preparation of ADC from conjugation reaction may be characterized by the methods of this invention, i.e. LC/MS, and indirectly by cathepsin B cleavage followed by ELISA assay to measure the levels of free drug as indicated in Sanderson et al (2005) Clinical Cancer Res. 11:843-852). Even though both methods would provide an average number of drug per antibody, the LC/MS method provides additional information about the distribution of p (drug) per intact antibody, as well as on light and heavy chain fragments. This important distribution parameter may be determined by methods of the present invention with the separation of the individual molecules of an ADC composition and their characterization and quantitation. Separation of the constituents of the sample occurs both at the separation media step of the method and during the mass spectrometry step. The high resolution of the separation media step of the methods of the invention provides separation, purification, and quantitation of separated sample constituents from complex, heterogeneous ADC samples. The high resolution and accuracy of the mass spectrometric step of the methods of the invention provides detection and quantitation of the separated sample constituents.

The methods of the invention can determine the amount of bound drug per antibody (loading) of ADC and the distribution of drug moieties on fragments such as heavy chain and light chain, and even to locate covalently attached drug moieties in sub-fragment loci of the antibody, or at particular amino acid residues.

For some ADC, p may be limited by the number of attachment sites on the antibody. For example, where the attachment is to an antibody cysteine thiol, as in the exemplary embodiments above, an antibody may have only one or several cysteine thiol groups, or may have only one or several sufficiently reactive thiol groups through which a linker may be attached. Less reactive amino acid residues such as lysine may be more numerous in the antibody to be conjugated, but may be unreactive and unavailable for reaction with the drug moiety or drug-linker reagent. Higher drug loading, e.g. p>5, may cause aggregation, insolubility, toxicity, lack of efficacy, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with an amine-reactive drug-linker intermediate or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges and must be reduced with a reducing agent such as dithiothreitol (DTT) or tris(2-carboxyethyl) phosphine hydrochloride (TCEP), under partial or total reducing conditions. Additionally, the antibody may be subjected to denaturing, or partially denaturing, conditions to reveal reactive nucleophilic groups such as lysine or cysteine. The loading (drug/antibody ratio) of an ADC may be controlled by several parameters, including: (i) limiting the molar excess of drug-linker intermediate or linker reagent relative to antibody, (ii) limiting the conjugation reaction time or temperature, and (iii) partial or limiting reductive conditions for cysteine thiol modification.

Where more than one nucleophilic group of the antibody reacts with a drug-linker intermediate, or linker reagent followed by drug moiety reagent, then the resulting product is a mixture of ADC compounds with a distribution of drug moieties attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). However, these single loading value ADCs may still be heterogeneous mixtures because the drug moieties may be attached, via the linker, at different sites on the antibody.

Administration of Antibody Drug Conjugates

The antibody drug conjugates (ADC) of the invention may be contacted with, or administered to, biological sources by any route appropriate to the condition to be treated. The ADC will typically be administered to a mammal parenterally, i.e. infusion, subcutaneous, intramuscular, intravenous, intradermal, intrathecal and epidural. The biological sources that may be contacted, i.e. administered, with Formula I ADC, include: (i) mammals such as a mouse, a rat, a rabbit, a dog, a monkey, or a human; (ii) mammalian tissue; and (iii) cultured cells. Biological samples are collected from the biological source once, or at timed, periodic, or random intervals. Biological samples include: (i) blood, bile, urine, or feces; (ii) tissue extracts; and (iii) cell culture media, cell lysates, or cell extracts.

Pharmaceutical Formulations

Pharmaceutical formulations of therapeutic antibody drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to biological source recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including guar gum and dextrins; sugars such as glucose, mannose, sucrose, mannitol, trehalose or sorbitol; chelating agents such as EDTA; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

Metabolites of the Antibody Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof. The methods of the invention also include detection and characterization of metabolites of antibodies and antibody-drug conjugates which are separated sample constituents.

Metabolite products typically may be identified by administering the antibody-drug conjugate mixture in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its metabolized products from processing the urine, blood or other biological samples. The metabolite structures are determined by the mass spectrometric methods of the invention.

Figure 41:
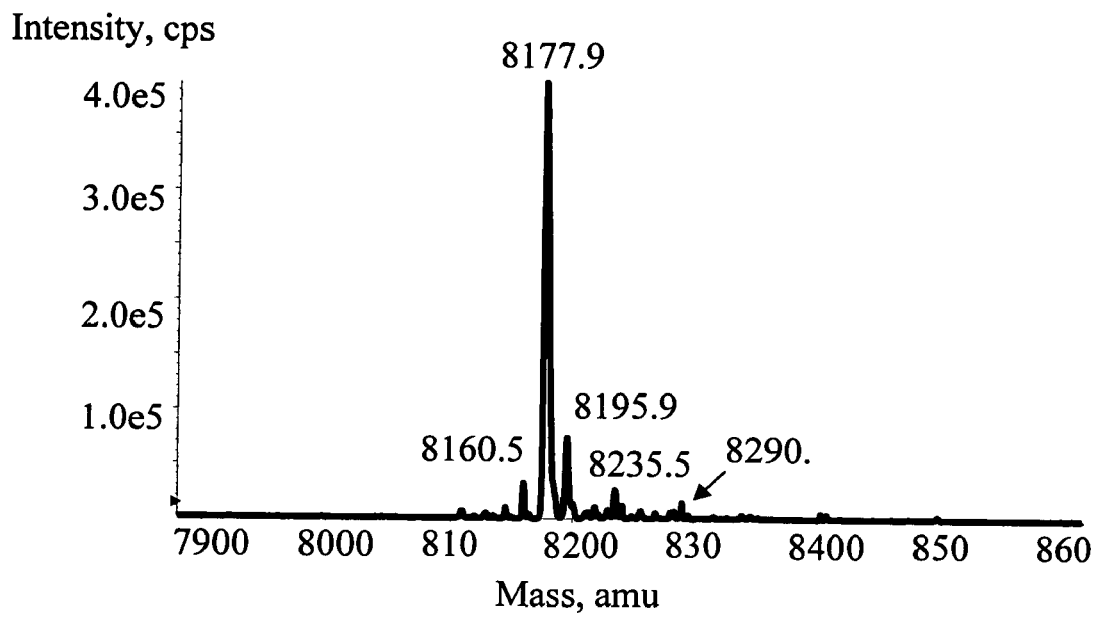
FIG. 41 shows mass spectrometry analysis plotting intensity in counts per second (cps) versus atomic mass units (amu) of a metabolite of trastuzumab-MC-MMAF with a mass of 8177.9 amu, captured on an anti-auristatin antibody affinity membrane from an in vivo plasma sample from cynomolgus monkey.

An example of such a metabolite was observed during analysis of a plasma sample from in-vivo αHer2(trastuzumab)-MC-MMAF cynomolgus monkey (*Macaca fascicularis*) TK studies. FIG. 41 represents a small protein (8178 MW) captured and isolated by an anti-auristatin affinity membrane. As the pharmacokinetic profile shows in FIG. 42, the concentration of this protein increases over time until it reaches a plateau after 10 hours and maintains its concentration for the duration of the study (5 days).

Pharmacokinetics

Monitoring circulating levels of a therapeutic for pharmacokinetic (PK) determinations in a mammal, including half-life, clearance, area under the curve (AUC), and volume of distribution, is necessary to establish safety/toxicity limits and appropriate dosing regimen (Welling, P. (1997) Pharmacokinetics Processes, Mathematics, and Applications, 2nd Ed., American Chemical Society, Washington, D.C.). Bioavailability is the extent to which the administered compound reaches general circulation from the administered dose form, usually expressed as a percentage of the administered dose. The half-life of a compound is the time required for 50% of the peak plasma concentration of the compound to be removed by excretion or biotransformation (metabolism). The therapeutic index expresses the selectivity of the compound between the desired therapeutic activity and the undesired toxic side effects. The pharmacokinetic measurements from the methods of the invention elucidate the absorption, distribution, metabolism, and excretion (ADME) of antibodies and antibody-drug conjugates (ADC).

Processing Biological Samples

After administration of the antibody-drug conjugate mixture to the biological source, a biological sample comprising the antibody-drug conjugate compound having the Formula I, or fragment or metabolite thereof is collected. The biological sample may be collected by any means, including withdrawing a fluid by syringe or cannula. The biological sample may be blood or blood products such as serum, plasma or the like, cerebrospinal fluid or other body fluid, e.g. saliva, urine, lymph, bile, feces, sweat, or breath vapor.

Preparation of antibody-drug conjugate samples for mass spectrometric analysis can be conducted generally according to known techniques. See: "Modern Protein Chemistry: Practical Aspects", Howard, G. C. and Brown, W. E., Eds. (2002) CRC Press, Boca Raton, Fla.

Processing biological samples serves to remove impurities and reduce sample heterogeneity which may hinder separation of the sample constituents, or obscure data collection or analysis. Alternatively, or in addition to, processing simplifies sample handling, preserves from degradation, minimizes sample volume, or selects for the sample constituents (analytes) of interest in the mass spectrometric analysis. Alternatively, or in addition to, processing converts biological samples into metabolites, fragments, or derivatives which are of interest in determining drug metabolism or pharmacokinetic effects.

Processing biological samples to form analysis samples may also be conducted by: formulating, immobilizing, centrifugation, isolating, digesting, inducing or preventing blood cell clotting, hydrolyzing, or purifying.

Immunoaffinity membrane (IAM) selection chromatography (using immobilized antigen) selectively isolated antibody-drug conjugates from plasma (Examples 1, 2, 3). Immunoaffinity techniques offer high specificity due to the strong non-covalent antigen-antibody interaction. The antigen is immobilized onto a solid phase support, the sample from the biological source containing the protein is added, the non-specific proteins, e.g. albumin, are washed away, and the protein of interest is eluted. Exemplary immunoaffinity membrane selection media include: POROS® AL-50 resin, Monolith CIM (Convection Interactive Media®, BIA Separations, Slovenia) epoxy disks and EMPORE® affinity membranes (3M, St. Paul, Minn.). A PROSPEKT-2® instrument (Chromatographic Specialties, Inc., Brockville, Ontario) was used for automated column washing and switching prior to introduction into the mass spectrometer (Example 1).

Figure 27:
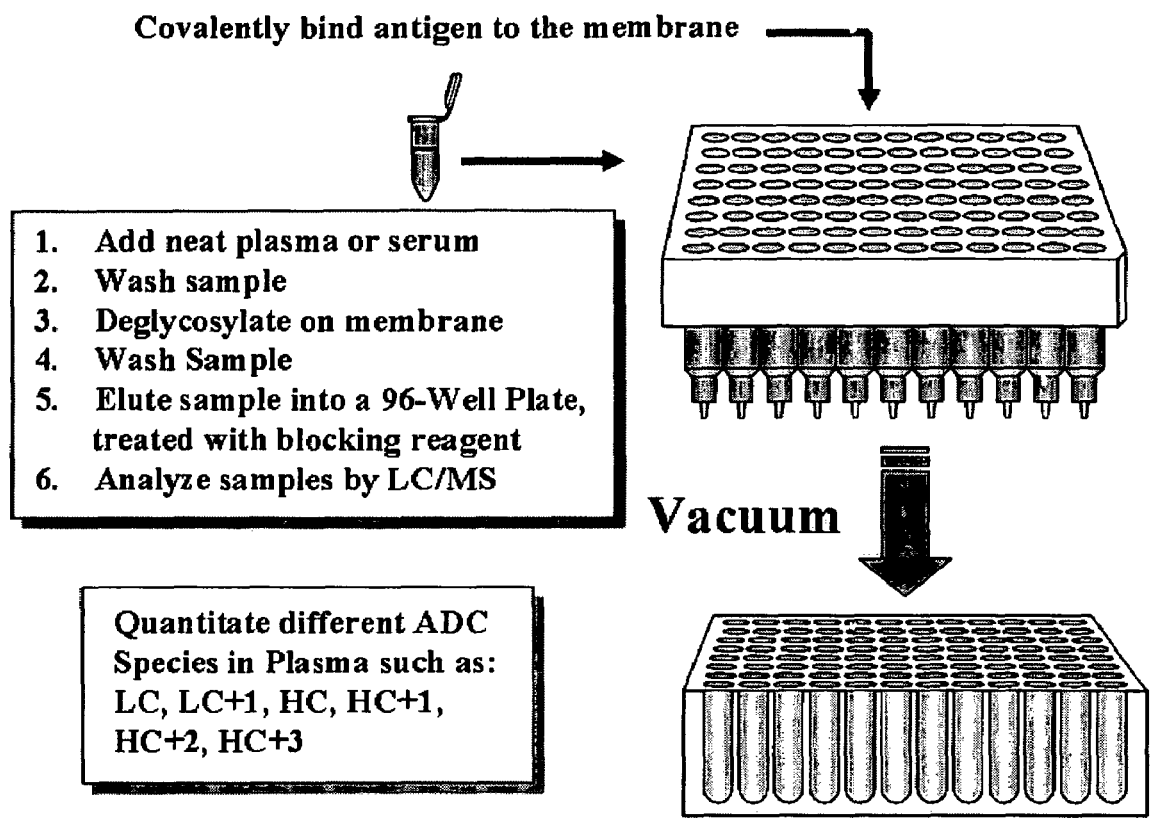
FIG. 27 shows the sample preparation steps for using the 96-well, vacuum manifold, immunoaffinity membrane (IAM) selection for antibody isolation prior to LC/MS analysis.

FIG. 27 shows the multiwell, vacuum manifold method of immunoaffinity membrane (IAM) selection binding for analysis sample formation for LC/MS analysis (Example 2). An antigen specific for the antibody of the administered antibody-drug conjugate is covalently attached to a membrane in each of the vessels that compose the multiwell plate. Plasma or serum samples from the mammal (biological source) that received the antibody-drug conjugate composition are applied by manual pipetting or automated robotic dispensing. Sample constituents specific for the membrane bound antigen are allowed to bind. The membrane is washed to elute non-specific proteins and other non-specific sample constituents. Bound antibodies may be deglycosylated on the membrane, e.g. with PNGaseF. The bound sample constituents may be eluted into a sample plate, with segregated receiving vessels or wells. The eluted samples may then be addressed by manual pipetting or by robotic transfer and separated by reverse phase chromatography and the separated sample constituents are analyzed by mass spectrometry.

In an exemplary embodiment, the biological sample may be digested with trypsin digestion. For trypsin digestion, samples may be reduced with DTT, S-carboxymethylated with sodium iodoacetate, and then digested with trypsin. Digested samples may be processed by methods including: (i) reverse phase HPLC, e.g. Nucleosil C18 column; (ii) size-exclusion chromatography (SEC), e.g. TSK 3000SWxL column; or (iii) boronate affinity chromatography using a TSK Boronate column.

Separation Methods and Media

To form the analysis sample, the biological sample may be applied to a separation media to effect separation of more than one sample constituent. Separation methods include affinity, chromatography, and electrophoresis methods. Affinity methods include affinity chromatography, antibody/antigen immunoaffinity, immunoaffinity chromatography, adsorption, immunoadsorption, and immobilized affinity matrices. Chromatography methods include HPLC, hydrophobic interaction (HIC), anion exchange, cation exchange, reverse-phase, normal phase, ion-pair reverse-phase, thin-layer, and size-exclusion. Electrophoretic methods include single dimensional, slab gel, capillary, polyacrylamide, denaturing, native, free solution, paper, 2-dimensional, isoelectric focusing, and gradient voltage. Other separation methods include: dialysis, centrifugation, magnetic, magnetic beads, immunomagnetic (WO 2003087772), sedimentation, floatation, precipitation, immunoprecipitation, and gel filtration.

Separation methods may effect separation of the constituents of the biological sample by one or more physico-chemical properties including, but not limited to, elution time, hydrophobicity, hydrophilicity, migration time, rate, velocity, chromatographic retention time, solubility, molecular volume or size, net charge, charge state, ionic charge, isoelectric point, dissociation constant (pKa), antibody affinity, electrophoretic mobility, ionization potential, dipole moment, hydrogen-bonding capability, and ion mobility in gas phase.

Figure 13:
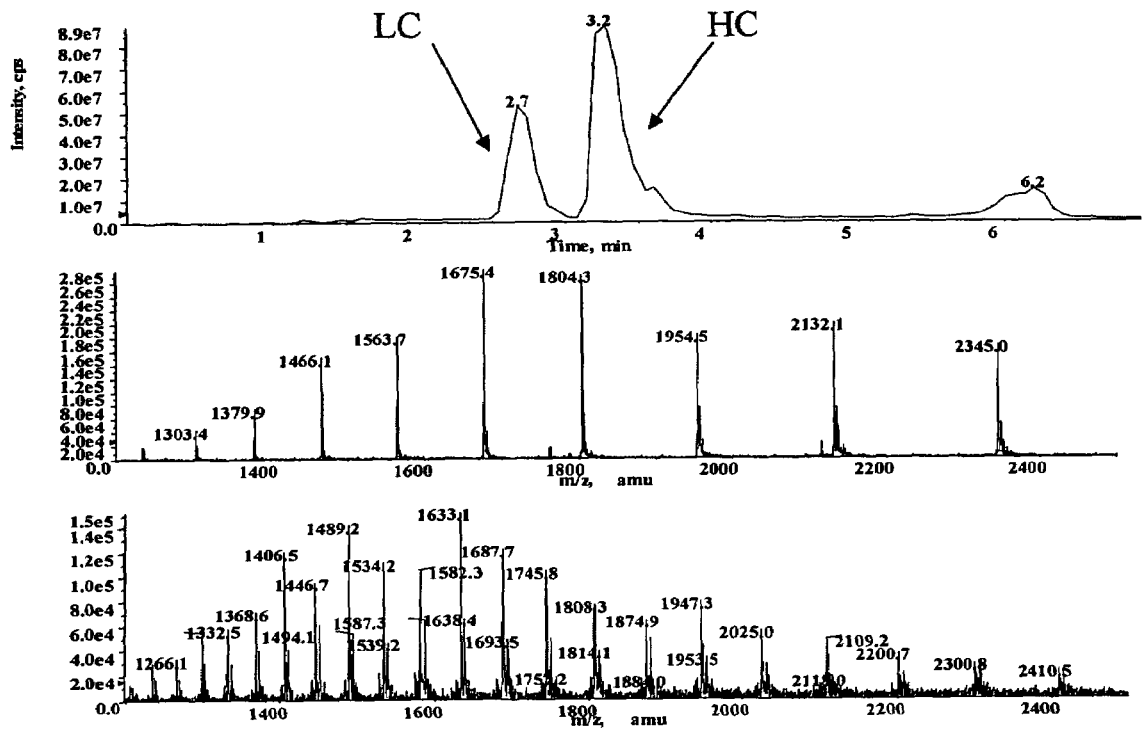
FIG. 13 shows a chromatogram (top) and mass spectra (middle and bottom) of reduced trastuzumab-SPP-DM1.
Figure 14:
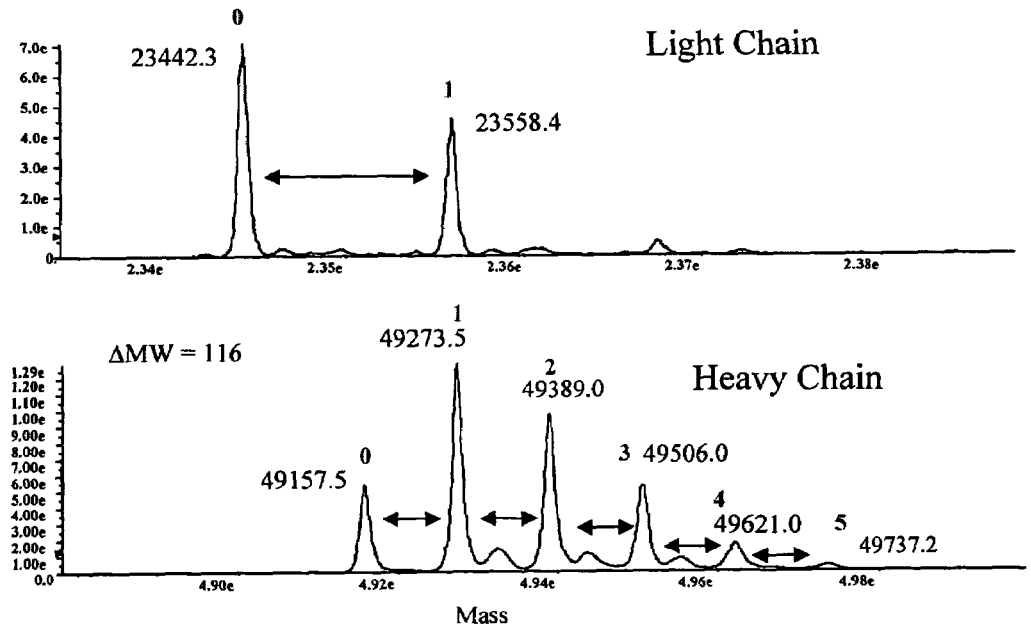
FIG. 14 shows deconvoluted mass spectra of the light and heavy chains of reduced trastuzumab-SPP-DM1.

Antibody-drug conjugates may be enzymatically deglycosylated with PNGaseF prior to analysis. For analysis of both intact and reduced conjugates, a reversed phase column (PLRP-S 2.0×50 mm, 8 µm, 4000 Å) coupled to an API 3000 mass spectrometer was employed (Mann et al "A Novel Approach to Characterization of Trastuzumab-DM1 Conjugates using LC-MS for Confirmation of Statistically Calculated Distributions", 51st Conference on Mass Spectrometry and Allied Topics, American Society for Mass Spectrometry, Montréal, Québec, Jun. 8-12, 2003). Trastuzumab-DM1 samples were analyzed (FIGS. 6 and 7). The reduction procedure involved reacting the conjugated antibody with 1,4- dithiothreitol (DTT) at 37° C. for 30 minutes (FIGS. 13 and 14). Although the DM1 is also cleaved during the reduction, a 116 dalton linker fragment remains attached at the conjugation site. Trastuzumab-DM1 conjugate lots and their corresponding precursors (Trastuzumab-SPP linker conjugates) were evaluated by analyzing intact and reduced samples with LC/MS. The number of DM1 or linker moieties on each light (0, 1, or 2) and heavy (0, 1, 2, 3, 4, or 5) chain can differ and each antibody has a pair of light and heavy chains allowing for many possible combinations.

An exemplary reverse phase chromatography adsorbent is a highly cross-linked polystyrene particle such as PLRP-S (Polymer Laboratories, Amherst, Mass.).

In an exemplary embodiment, the biological sample may be purified by cation-exchange chromatography (IEC) on a Dionex Pro Pac WCX-10 column. Fractions were collected, concentrated with Centricon-30.

Mass Spectrometry

The methods of the invention are appropriate for the analysis of antibody mixtures derived from biological samples where different chemical constituents of the mixture are first isolated, separated, or partially separated by one or more processes including affinity or chromatography which cause the constituents to elute sequentially or in a batch wise manner, or to be directly detected by mass spectrometry. Various structural features and properties of antibodies can be elucidated from mass spectrometry analysis including: fragmentation, deamidation, glycation, oxidation, partial sequence information, e.g. N-terminal and C-terminal, dimer and aggregation states. One or more chemical constituents in the biological sample can be characterized in a highly specific manner by measurement of its accurate mass since the administered antibody-drug conjugate is of known sequence, structure, and molecular weight.

A variety of mass spectrometry systems capable of high mass accuracy, high sensitivity, and high resolution are known in the art and can be employed in the methods of the invention. The mass analyzers of such mass spectrometers include, but are not limited to, quadrupole (Q), time of flight (TOF), ion trap, magnetic sector or FT-ICR or combinations thereof. The ion source of the mass spectrometer should yield mainly sample molecular ions, or pseudo-molecular ions, and certain characterizable fragment ions. Examples of such ion sources include atmospheric pressure ionization sources, e.g. electrospray ionization (ESI) and Matrix Assisted Laser Desorption Ionization (MALDI). ESI and MALDI are the two most commonly employed methods to ionize proteins for mass spectrometric analysis. ESI and APCI are the most commonly used ion source techniques for LC/MS (Lee, M. "LC/MS Applications in Drug Development" (2002) J. Wiley & Sons, New York).

Surface Enhanced Laser Desorption Ionization (SELDI) is an example of a surface-based ionization technique that allows for high-throughput mass spectrometry (U.S. Pat. No. 6,020,208). Typically, SELDI is used to analyze complex mixtures of proteins and other biomolecules. SELDI employs a chemically reactive surface such as a "protein chip" to interact with analytes, e.g., proteins, in solution. Such surfaces selectively interact with analytes and immobilize them thereon. Thus, the analytes of the invention can be partially purified on the chip and then quickly analyzed in the mass spectrometer. By providing different reactive moieties at different sites on a substrate surface, throughput may be increased.

Commercially available mass spectrometers can sample and record the whole mass spectrum simultaneously and with a frequency that allows enough spectra to be acquired for a plurality of constituents in the mixture to ensure that the mass spectrometric signal intensity or peak area is quantitatively representative. This will also ensure that the elution times observed for all the masses would not be modified or distorted by the mass analyzer and it would help ensure that quantitative measurements are not compromised by the need to measure abundances of transient signals.

A method was developed for simultaneous quantitation of small molecule and antibody drug conjugate by LC/LC/MS. To accomplish this, each part was developed independently and later combined. An LC/MS/MS method was also developed for quantitating the drug moiety and metabolites using the PROSPEKT-2® instrument (Spark Holland) for online solid-phase extraction (SPE), SYNERGI™ C12 (Phenomenex, Torrance, Calif.) reverse phase chromatography for chromatographic separation, and an API 3000 mass spectrometer for detection (Kadkhodayan, M. and Mann, E. "New Strategies in Characterization and Quantitation of Antibody-targeted Drug Conjugates in Plasma using LC/LC/MS", 51st Conference on Mass Spectrometry and Allied Topics, American Society for Mass Spectrometry, Montréal, Québec, Jun. 8-12, 2003; Beaudry et al (1998) Rapid Commun. Mass Spectrom. 12:1216-1222; Simpson et al (1998) Rapid Commun. Mass Spectrom. 12:75-82), and as detailed in Example. 1. This small molecule portion of the method had a range of 0.3 to 750 ng/ml for auristatin and maytansinoid drugs. Linear curves in plasma were obtained ($R^2$=0.999).

Figure 16:
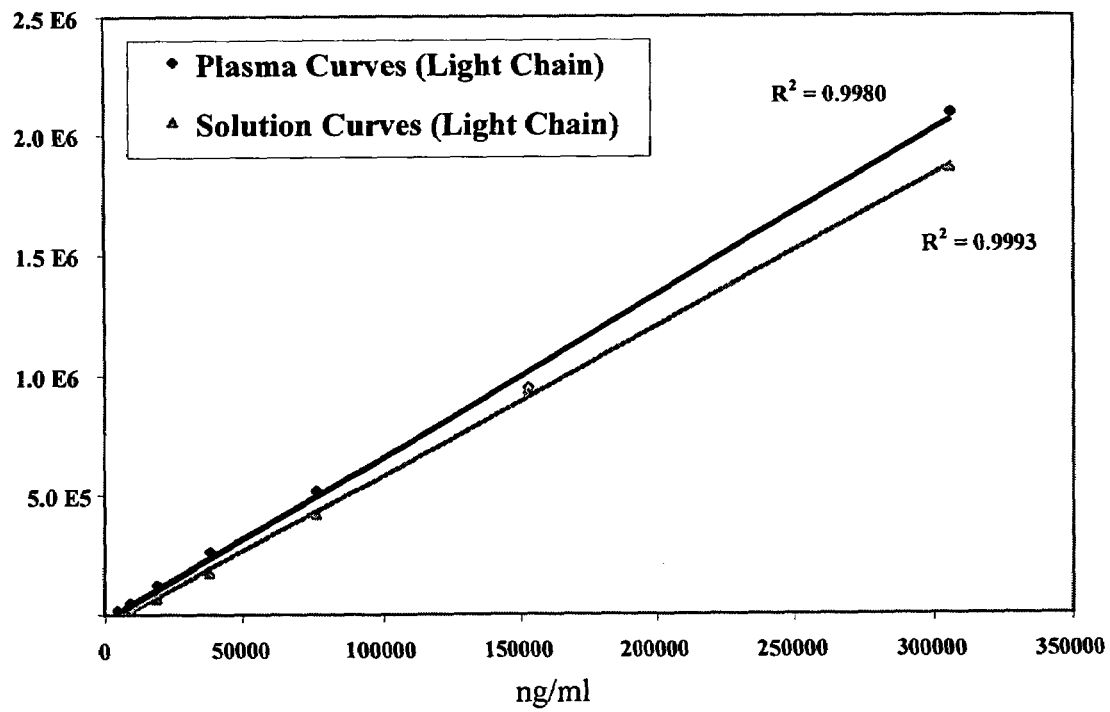
FIG. 16 shows LC/LC/MS calibration curves for plasma and solution samples of reduced trastuzumab light chain.

Quantitation of the antibody species was accomplished by single ion monitoring (SIM) using an ion from each species of interest (LC and LC+1D). This enabled comparison of relative amounts of each conjugate species in plasma. Linear curves in solution and plasma are shown in FIGS. 16 and 17 for both the unmodified (LC) and conjugated (LC+D) light chain of the antibody, respectively.

Figure 18:
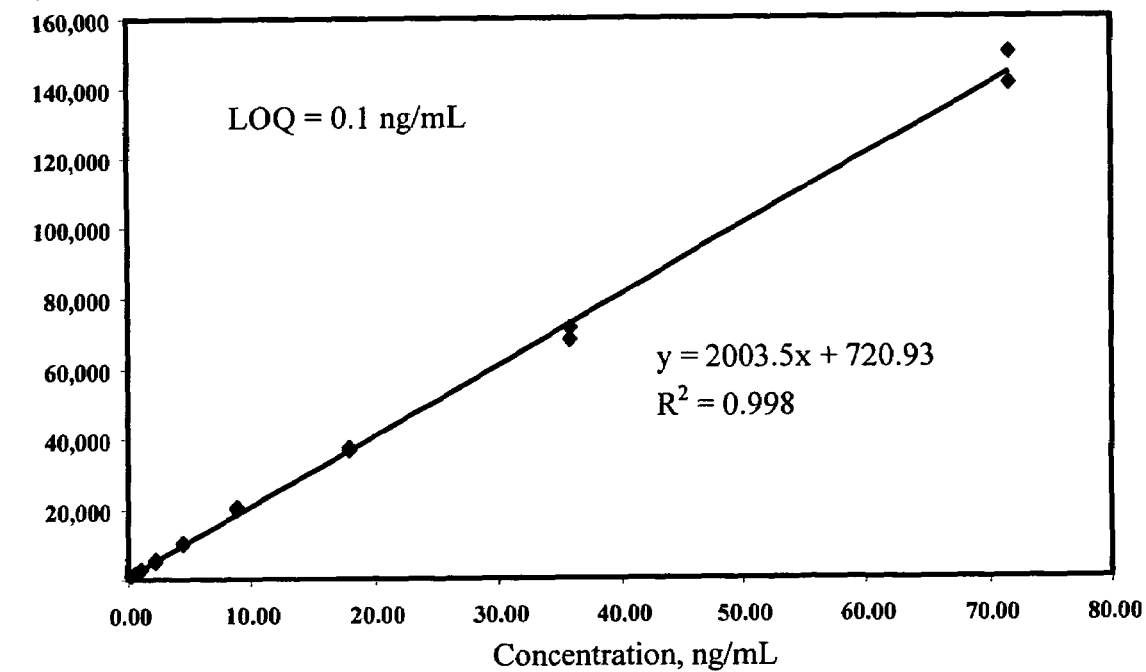
FIG. 18 shows a calibration curve for free drug MMAE in rat plasma, with an LOQ of 0.1 ng/ml.

FIG. 18 shows a calibration curve for free drug MMAE in rat plasma, with an LOQ of 0.1 ng/ml. The LC/LC/MS antibody method was combined with the small molecule SPE method on the PROSPEKT-2 instrument. The combined method performs affinity isolation of the antibody conjugate, online SPE extraction of the free drug, reverse phase separation of the small molecule, followed by reversed phase separation of the conjugated antibody. The waste stream from the immunoaffinity column (which contains the free drug) is directed through the C18 SPE cartridge before it is discarded. The SPE cartridge is eluted while the plasma is washed from the affinity column and finally the affinity column is eluted. Two data files are thus generated from one plasma injection and provide valuable quantitation data for the conjugated antibody species in vivo.

Electrospray Ionization Mass Spectrometry (ESI)

Masses of relatively high molecular weight compounds such as antibodies can be detected at mass-to-charge ratios (m/z) that are easily determined by most mass spectrometers (typical m/z ranges of up to 2000 to 3000). Electrospray ionization mass spectrometry ESI-MS, in particular, is suited for charged, polar or basic compounds and for analyzing multiply charged compounds with excellent detection limits. ESI thus allows detection and characterization of large biomolecules, such as antibodies and antibody-drug conjugates with molecular weight (MW) of 150,000 or higher. With high-mass ions, a series of multiply charged molecular ions are typically observed. The molecular weight for positive ions is determined by multiplying the measured m/z ratio minus the mass of the cation (C+) times the number of charges (n) on that ion.

$$MW=n(m/z-nC+)$$

Electrospray ionization (ESI) is compatible with liquid separation methods (front end), as well as MS/MS methods (back end)("Electrospray Ionization Mass Spectrometry: Fundamentals, Instrumentation, and Applications", Cole, R. B., Ed. (1997) Wiley, N.Y.). A dilute solution of a peptide, protein, or other biomolecule may be introduced to the mass spectrometer system by syringe pump, flow injection or LC/MS. ESI-MS data may be acquired by averaging a number of scans together and smoothing the data to provide good peak intensity and shape. For low-mass compounds, the most abundant peaks observed are often the [M+H]+ ions in the positive-ion mode and [M−H]− in the negative ion mode. Doubly and triply charged ions as well as dimers may also be observed. Doubly charged positive ions will be observed at a mass (MW +2C+)÷2 where MW is the molecular weight and C+ is the ionizing cation, such as $H^+$, $Na^+$, or $NH4^+$. Except for the very low mass compounds, the detected ions will be multiply charged. Due to the soft ionization conditions of ESI, often multiply charged ions are observed. Therefore, many m/z peaks are observed in the ESI spectra for macromolecules which represent a single molecular weight. The calculation of the molecular weight can be accomplished either by solving two equations with two unknowns or by purchasing deconvolution software from a vendor which can automatically calculate the mass of the macromolecule.

ESI of proteins produce multiply charged ions with the number of charges tending to increase as the molecular weight increases. The number of charges on a given ionic species may be determined by methods such as: (i) comparing two charge states that differ by one charge and solving simultaneous equations; (ii) looking for species that have the same charge but different adduct masses; and (iii) examining the mass-to-charge ratios for resolved isotopic clusters. The methods of ESI and ESI-MS and parameters needed to conduct these methods are well known in the art. The gentleness of the electrospray ionization process allows intact antibody conjugates to be directly detected by mass spectrometry.

In one embodiment, a Q1 mass spectrum of the protein, antibody, antibody fragment or antibody-conjugates (large molecules) is run as part of the method. A suitable quality Q1 mass spectrum of a large molecule can be obtained as follows:

Since there is potential for the protein envelope to shift, all the solvents used for chromatography are made fresh and acid is added to the elution solvent to position the spectrum envelop in the observed range. For proteins of ≧100,000 mass units, an acid such as formic acid can be used at about 0.1% (volume) in the elution solvents, for example, both solvent A (water) and B (acetonitrile). A stronger acid can be used, such as trifluoroacetic acid (TFA), at 0.05% (volume) TFA for both A and B solvents for proteins with ≦100,000 mass units. The parameters of acid, solvent and DP affect ionization of intact and reduced antibody. The ionization effect of reducing the acid from 0.2% to 0.05% is shown in FIG. 1. As the amount of formic acid is decreased, the intact glycosylated antibody, trastuzumab, picks up more charge, shifting the envelope further to the left and into the observed range of m/z (1800-3000 m/z). Mass spectra C and D in FIG. 1 show that as the declustering potential (DP) voltage is increased from 30-120V to 70-190V that the charge on the antibody increases even further. Thus voltage applied, solvent composition, and ion pairing agents are factors to consider and adjust.

To prove that the protein envelope does not shift, ions were selected from a wide range of m/z and plotted concentration versus peak intensity (FIG. 2). Linearity may be obtained over a wide range of m/z. FIG. 2 shows the charged states of an anti-HER2 antibody, trastuzumab (HERCEPTIN®), obtained from a Q1 scan of a light chain of the antibody. For the quantitation of the amounts of intact antibody or heavy chain, fragments or ADCs, deglycosylation of the antibody is suggested. Glycosylation contributes to lower ionization efficiency and thus reduced sensitivity. It also generally produces non-linear (quadratic) calibration curves. FIG. 3 shows ESI-MS of glycosylated trastuzumab and spectral deconvolution.

Figure 5:
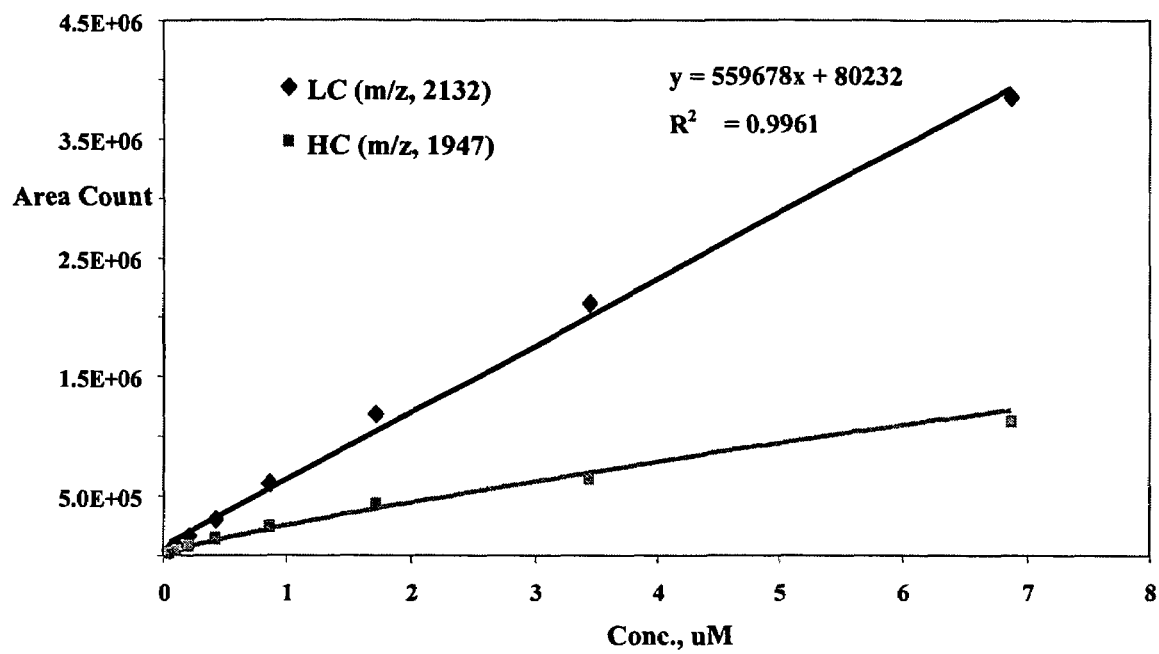
FIG. 5 shows calibration for quantitation by ESI-MS, at different concentrations of the light chain (LC) and heavy chain (HC) of reduced trastuzumab.

FIG. 4 shows calibration curves for quantitation by ESI-MS of: intact trastuzumab (αHer2) and deglycosylated intact trastuzumab. FIG. 5 shows calibration curves for quantitation by ESI-MS of the light chain (LC) and heavy chain (HC) of reduced trastuzumab.

When quantitating antibody or antibody fragment conjugates, deglycosylation of the antibody may reduce the heterogeneity of the mass spectrum, increase sensitivity and thus simplifying the analysis. FIG. 6 shows ESI-MS of an antibody-conjugate, trastuzumab-SPP-DM1, after deglycosylation with PNGaseF and hydrolytic cleavage of DM1. FIG. 7 shows the deconvolution spectrum of the raw data of FIG. 6.

Figure 21:
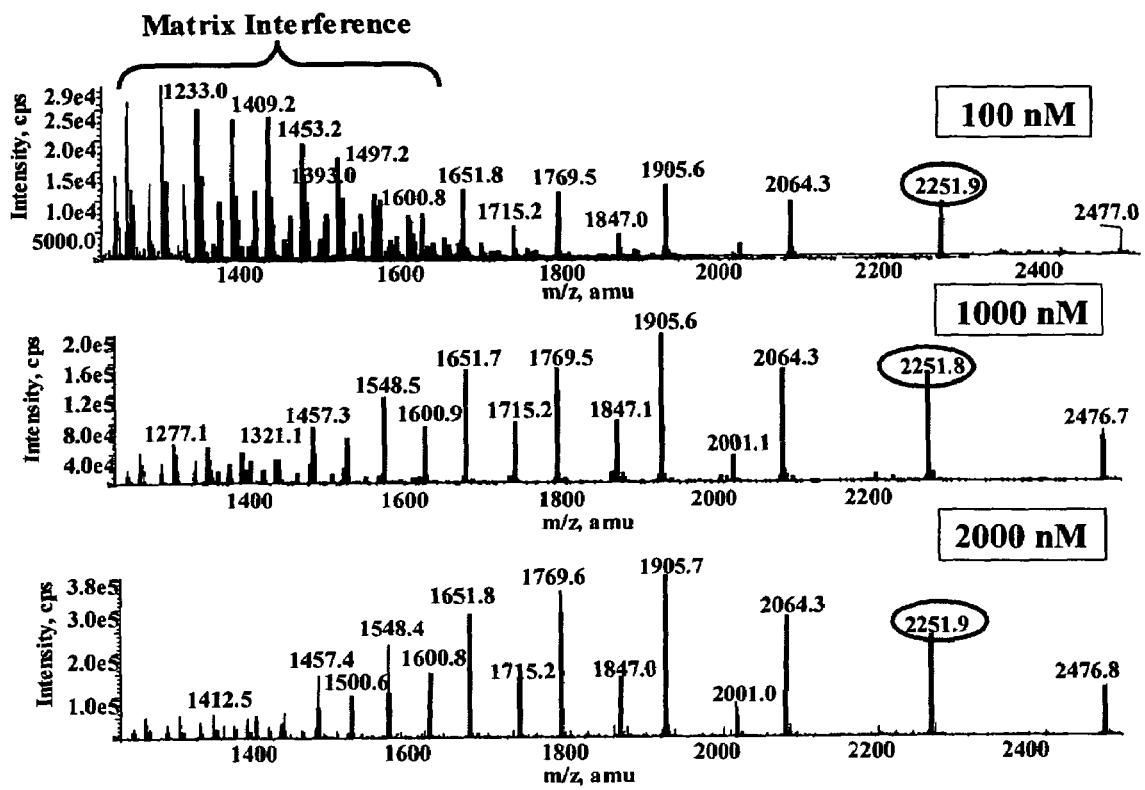
FIG. 21 shows mass spectra Q1 scans at 3 different concentrations of trastuzumab in plasma solution at 100 nM (top); 1000 nM (middle); and 2000 nM (bottom).

In one embodiment, the charged ion range for quantitation is determined. When selecting the charged ion range for quantitation, a region of the spectrum is selected that does not have matrix interference. This is determined experimentally for each protein and by running a Q1 spectrum (FIG. 21), and selecting a charged ion such as 2251.9 where the region of spectrum is free of matrix interference.

In another embodiment, deconvolution tables are used to determine the exact mass to charge ratio (m/z) for each species to quantitated. Deconvolution software applications such as Analyst™ (Applied Biosystems, Foster City, Calif.) are commercially available and/or provided with mass spectrometers. Deconvolution software generally provides the user with a table of deconvoluted masses as well as a sub-table of m/z ions used to calculate these masses, from which the ions selected for SIM method can be extracted.

Using the exact m/z, a SIM method is generated for all species to quantitated. Several m/z charged ions for each species may be selected since the charged state with greatest signal to noise may not necessarily be the best charged state for quantitation due to matrix interference. Often the best charged state is in the higher m/z range (~1800 to 2700) because of lack of matrix interference and resolution. In one exemplary embodiment, the dwell time for 1-10 ions is between 150 to 200 micro-seconds each. If more than ten ions are being monitored then the dwell time should be adjusted to 75 to 100.

Figure 22:
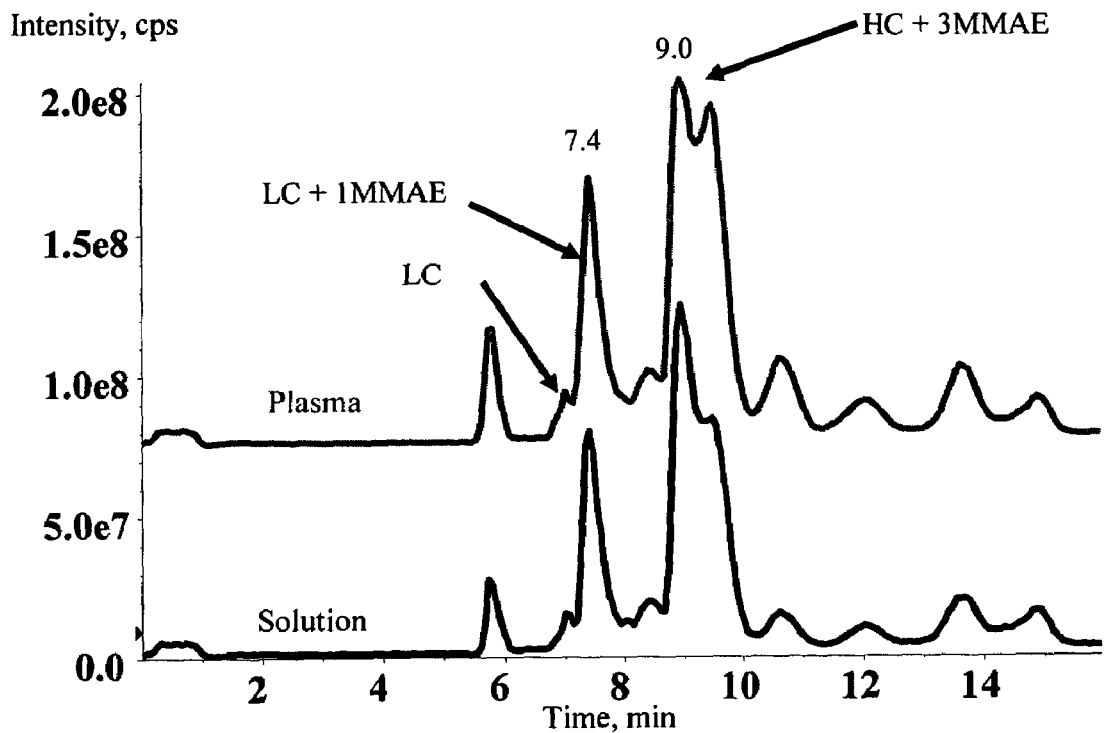
FIG. 22 shows chromatograms of rat plasma and solution samples isolated by immunoaffinity membrane (IAM) selection, reduction and denaturation of trastuzumab-MC-vc-PAB-MMAE.
Figure 23:
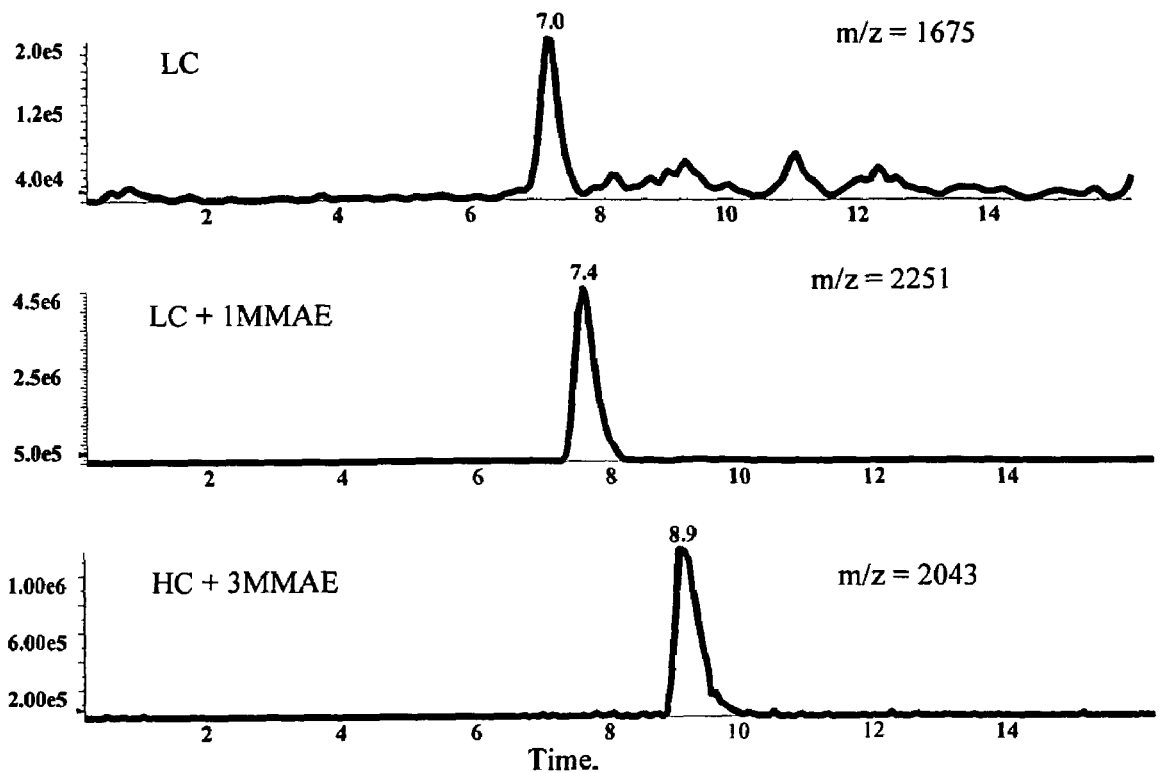
FIG. 23 shows single ion monitoring (SIM) of deglycosylated, reduced fragments of trastuzumab-MC-vc-PAB-MMAE in rat plasma: (top) light chain; (middle) light chain with one MMAE; (bottom) heavy chain with three MMAE.
Figure 24:
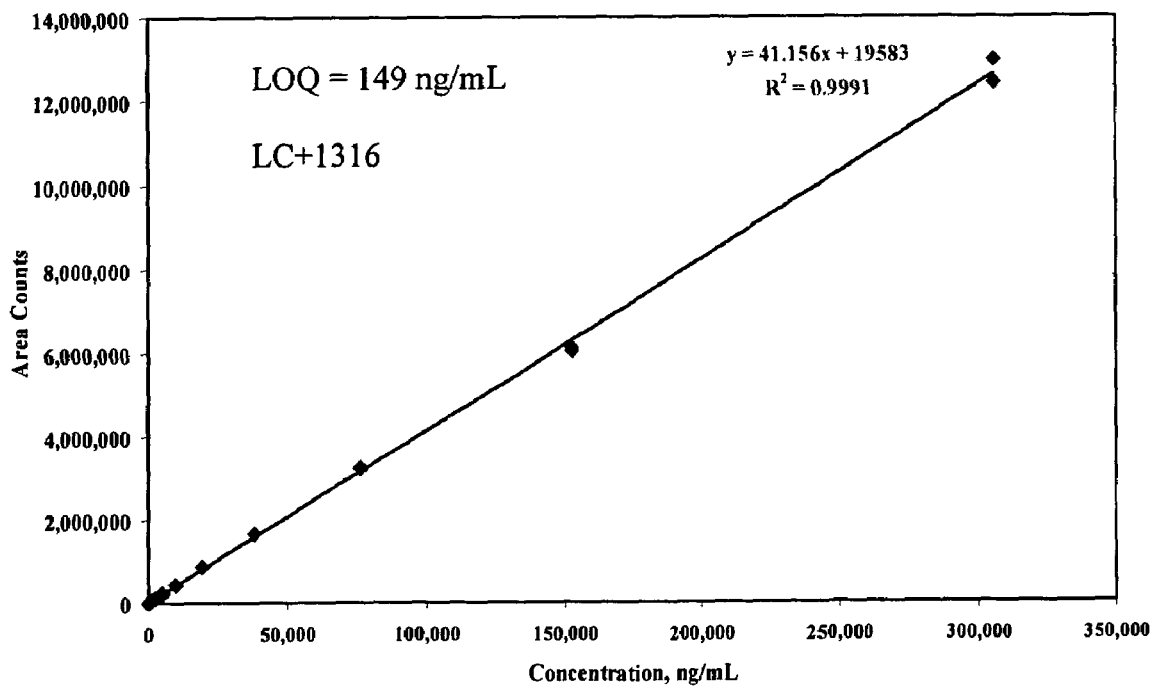
FIG. 24 shows a calibration curve for the 2251 m/z ion of the light chain with one MMAE drug moiety (LC+1 MMAE) of trastuzumab-MC-vc-PAB-MMAE in rat plasma, with an LOQ of 149 ng/ml.

FIG. 22 shows chromatograms of rat plasma and solution samples isolated by immunoaffinity membrane (IAM) selection, reduction and denaturation of trastuzumab-MC-vc-PAB-MMAE. FIG. 23 shows single ion monitoring (SIM) of deglycosylated, reduced fragments of trastuzumab-MC-vc-PAB-MMAE in rat plasma: (top) light chain; (middle) light chain with one MMAE; (bottom) heavy chain with three MMAE. FIG. 24 shows a calibration curve for the 2251 m/z ion of the light chain with one MMAE drug moiety (LC+1 MMAE) of trastuzumab-MC-vc-PAB-MMAE in rat plasma, with an LOQ of 149 ng/ml.

The SIM method may be used to prepare a calibration curve in the sample matrix to quantitate the desired species. The DP may be adjusted for each ion and test samples may be run to experimentally determine this variable for each species, such as shown in FIG. 1. A good DP starting point is 50 to 150 volts in increments of 10 voltage units. The lower limit of quantitation (LOQ) of LC+1 MMAE of the trastuzumab conjugate in FIG. 10 is 140 ng/ml. Once the method is optimized, a calibration curve is generated in the sample matrix, and the data acquired is processed using commercially available software. A dual affinity column method (Example 1) tested for linearity and whole plate variability. The antibody calibration curve from antibodies recovered from this membrane demonstrated great linearity ($R^2$=0.9993) for a range of 0.14 μg/ml to 75 μg/ml (FIG. 10), and whole plate precision (FIG. 11).

Figure 19:
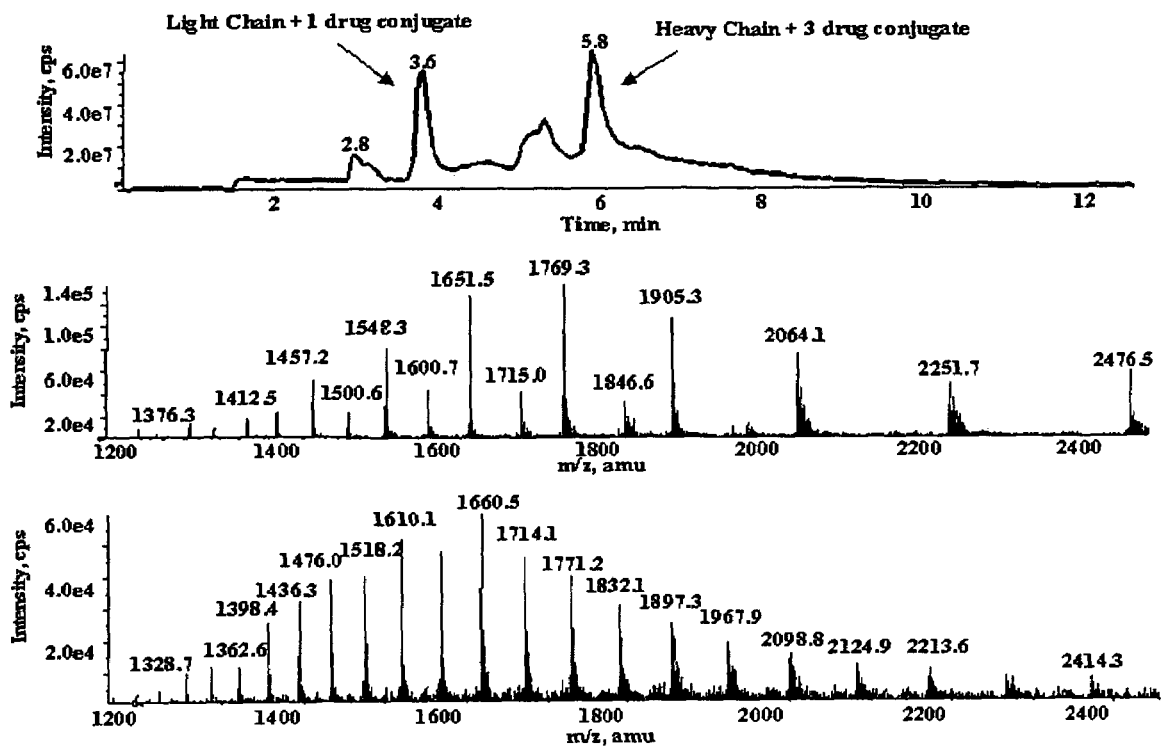
FIG. 19 shows: (top) a total ion chromatogram of reduced and denatured trastuzumab-MC-vc-PAB-MMAE; (middle) mass spectra of light chain with one MMAE; and (bottom) mass spectra of heavy chain with three MMAE.
Figure 20:
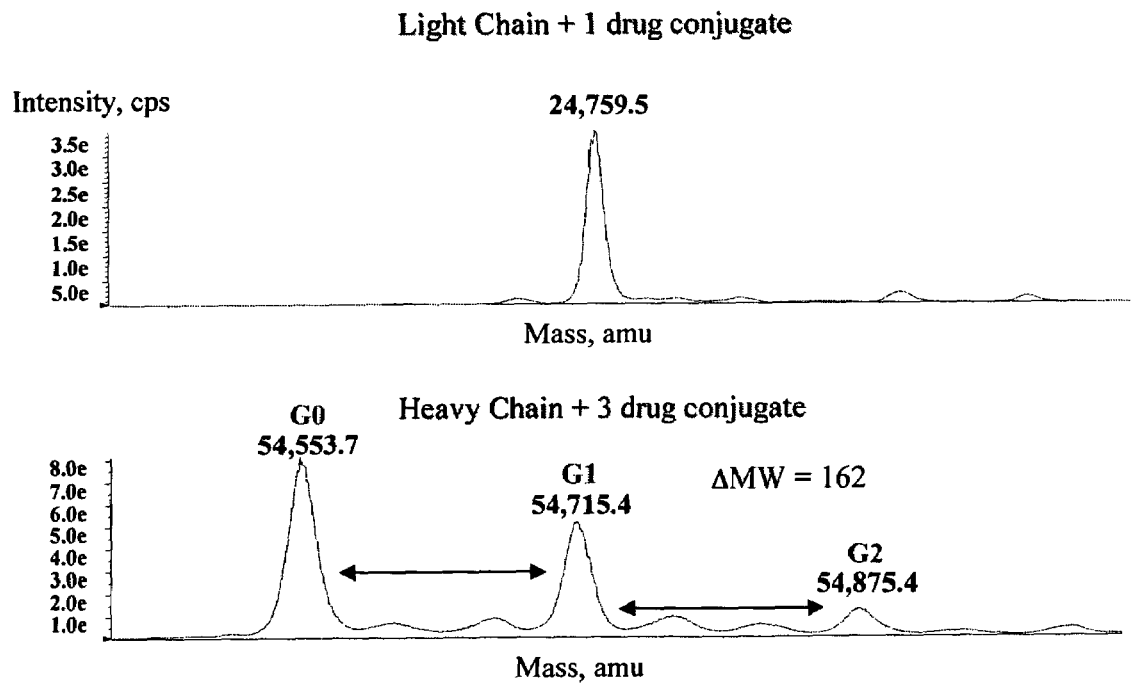
FIG. 20 shows the deconvoluted mass spectra of fragments of reduced trastuzumab-MC-vc-PAB-MMAE: (top) LC+1 MMAE and (bottom) HC+3 MMAE.

Quantitation was accomplished by single ion monitoring (SIM) using an ion from each species of interest (LC and LC+1). This enabled comparison of relative amounts of each conjugate species in plasma. Linear curves in solution ($R^2$=0.9993 and 0.9986) and plasma ($R^2$=0.9980 and 0.9994) were obtained unmodified trastuzumab (FIG. 16) and the antibody-drug conjugate, trastuzumab-MC-vc-PAB-MMAE, (FIG. 17), respectively (Kadkhodayan, M. and Mann, E. "New Strategies in Characterization and Quantitation of Antibody-targeted Drug Conjugates in Plasma using LC/LC/MS", 51st Conference on Mass Spectrometry and Allied Topics, American Society for Mass Spectrometry, Montréal, Québec, Jun. 8-12, 2003). FIG. 19 shows: (top) a total ion chromatogram of reduced and denatured trastuzumab-MC-vc-PAB-MMAE; (middle) mass spectra of light chain with one MMAE; and (bottom) mass spectra of heavy chain with three MMAE. FIG. 20 shows the deconvoluted mass spectra of fragments of reduced trastuzumab-MC-vc-PAB-MMAE: (top) LC+1 MMAE and (bottom) HC+3 MMAE.

Figure 25:
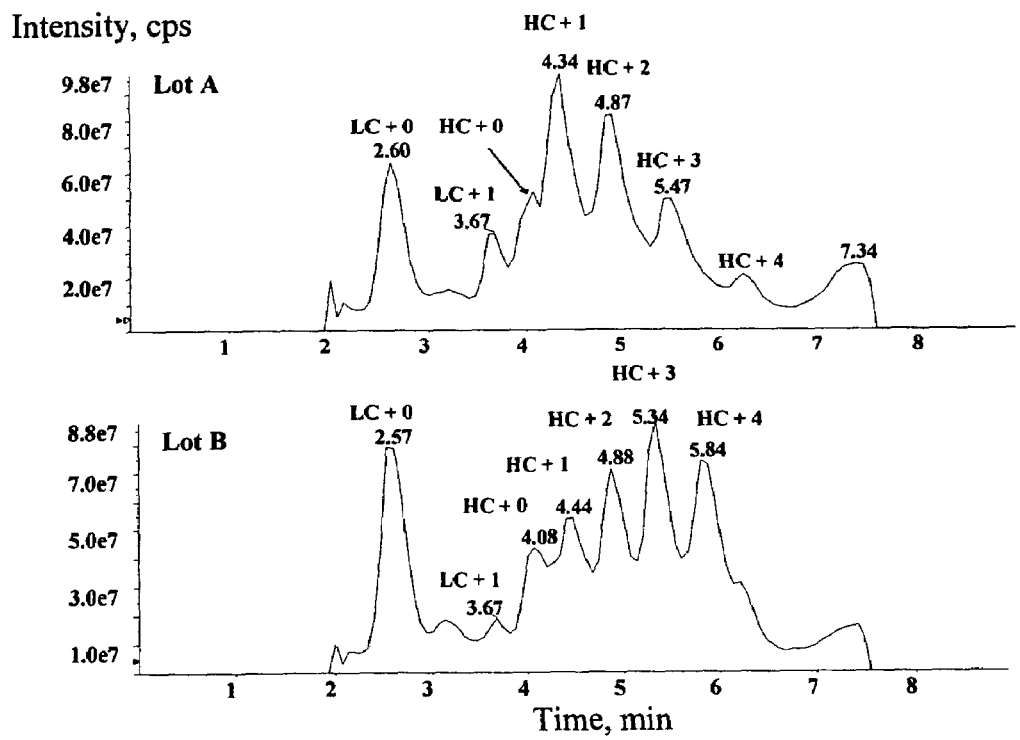
FIG. 25 shows LC analysis of two preparations of the anti-EphB2R antibody drug conjugate, 2H9-MC-vc-PAB-MMAE, with assignments of fragments; LC+0, LC+1, HC+0, HC+1, HC+2, HC+3, HC+4. The top chromatogram is 3.5 MMAE/2H9. The bottom chromatogram is 5.1 MMAE/2H9.
Figure 26:
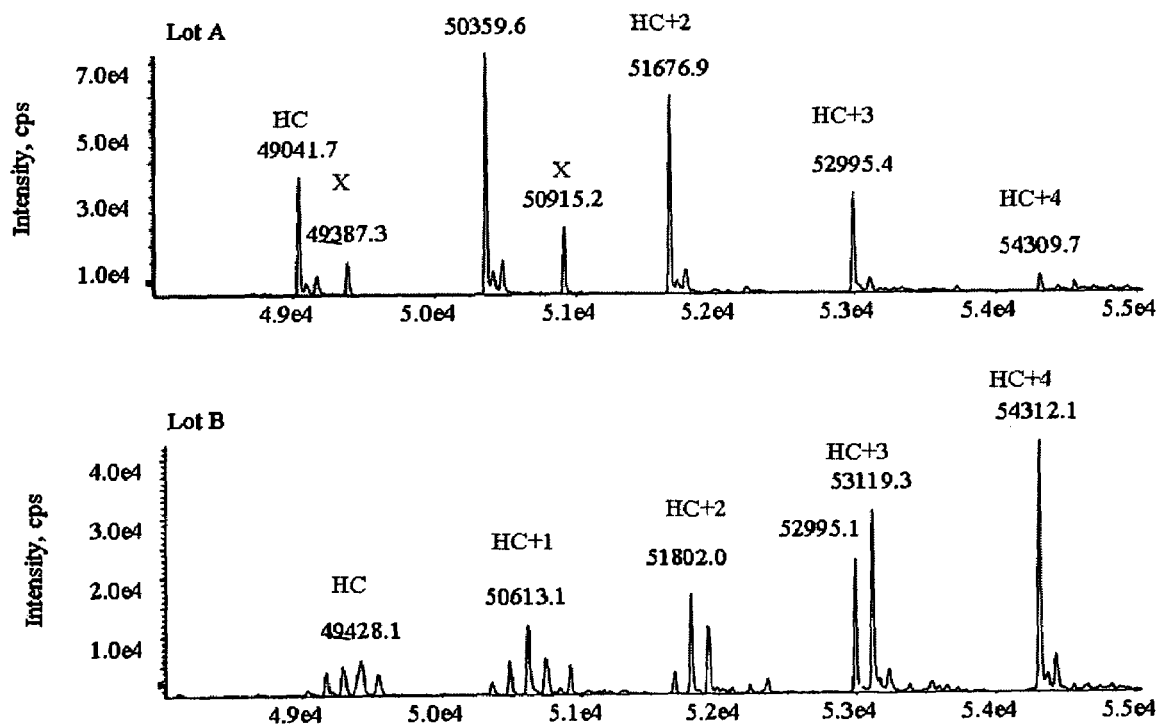
FIG. 26 shows Q1 LC/MS characterization of two preparations of 2H9-MC-vc-PAB-MMAE, which can determine the MMAE distribution of the antibody. The top mass spectra, Lot A, is 3.5 MMAE/2H9. The bottom mass spectra, Lot B, is 5.1 MMAE/2H9. Note that multiple peaks of each species are due to N-ethylmaleimide (NEM) addition.

FIG. 25 shows LC analysis of two preparations of the anti-EphB2R antibody drug conjugate, 2H9-MC-vc-PAB-MMAE, with assignments of fragments; LC+0, LC+1, HC+0, HC+1, HC+2, HC+3, HC+4. 2H9 is an IgG1 antibody with strong affinity for the ephrin B receptor. 2H9 also has 5 disulfide groups, with a potential for up to 10 reactive cysteine thiol groups after reduction. FIG. 26 shows LC/MS analysis of two preparations of 2H9-MC-vc-PAB-MMAE, with Q1 data collection for characterization. Table 1 compiles the integrated areas of the fragments of the two preparations of ADC, 2H9-MC-vc-PAB-MMAE, and establishes the drug loading on the light chains and heavy chains, and therefore total drug loading per antibody. Total average drug loading per 2H9 was calculated from the sum of the two HC and two LC fragments. Total average drug loading per 2H9 for the ADC preparation at the top of FIGS. 25 and 26 was 3.5 MMAE/2H9. Total average drug loading per 2H9 for the ADC preparation at the bottom of FIGS. 25 and 26 was 5.1 MMAE/2H9.

TABLE 1

LC/MS characterization of fragments of two preparations of 2H9-MC-vc-PAB-MMAE, from solution: MMAE/2H9 = 3.5 and 5.1

| fragment | MMAE per fragment | area | % ratio |
| --- | --- | --- | --- |
| MMAE/2H9 = 3.5 | | | |
| heavy chain | 0 | 151.1 | 16.7 |
| heavy chain | 1 | 336.2 | 37.1 |
| heavy chain | 2 | 266.7 | 29.5 |
| heavy chain | 3 | 125.8 | 13.9 |
| heavy chain | 4 | 25.2 | 2.8 |
| | | | MMAE/HC = 1.49 |
| light chain | 0 | 304.9 | 75.4 |
| light chain | 1 | 99.4 | 24.6 |
| | | | MMAE/LC = 0.25 |
| MMAE/2H9 = 5.1 | | | |
| heavy chain | 0 | 126.3 | 12.6 |
| heavy chain | 1 | 135.1 | 13.5 |
| heavy chain | 2 | 182.2 | 18.1 |
| heavy chain | 3 | 250.8 | 25.0 |
| heavy chain | 4 | 310 | 30.9 |
| | | | MMAE/HC = 2.48 |
| light chain | 0 | 384.4 | 91.2 |
| light chain | 1 | 37.3 | 8.8 |
| | | | MMAE/LC = 0.088 |

A similar LC/MS identification and characterization of the antibody-drug conjugate, trastuzumab-MC-vc-PAB-MMAE was conducted. One preparation gave a light chain loading of 1.0 (MMAE/LC) and a heavy chain loading of 2.9 (MMAE/HC), therefore a total drug loading of 7.8 (MMAE/trastuzumab). Another preparation gave a light chain loading of 1.0 (MMAE/LC) and a heavy chain loading of 1.6 (MMAE/HC), therefore a total drug loading of 5.1 (MMAE/trastuzumab).

Figure 28:
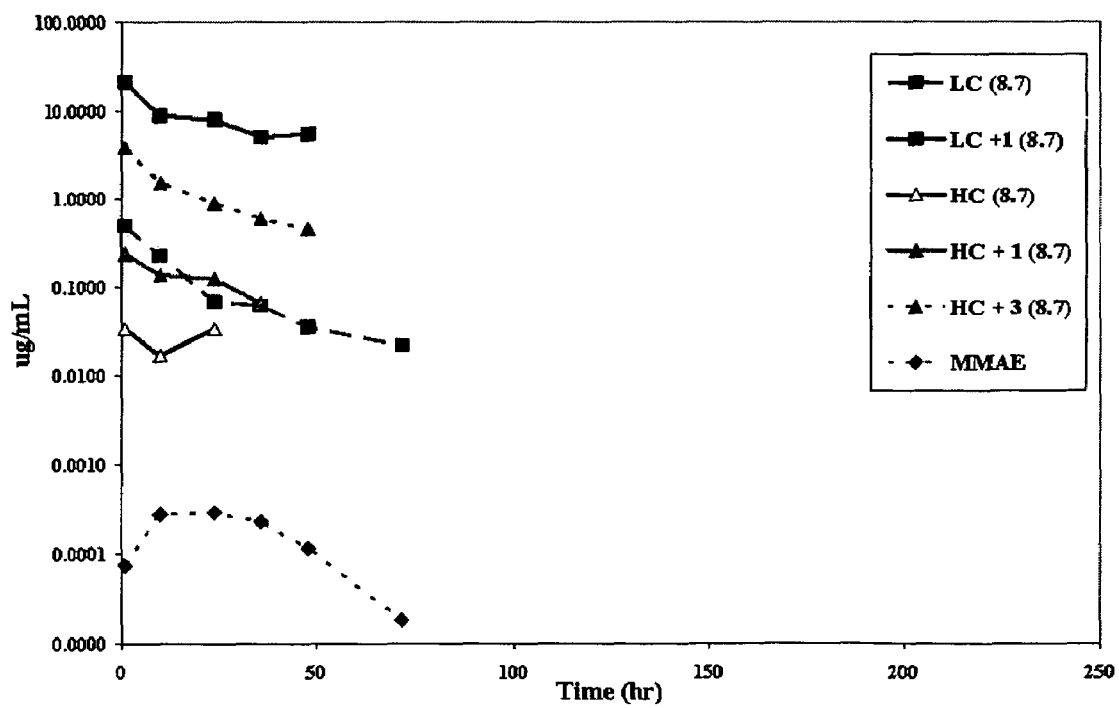
FIG. 28 shows the PK analysis of LC/MS samples from plasma from Sprague-Dawley rats dosed with trastuzumab-MC-vc-PAB-MMAE (8.7 MMAE/trastuzumab), 2 mg MMAE/kg
Figure 29:
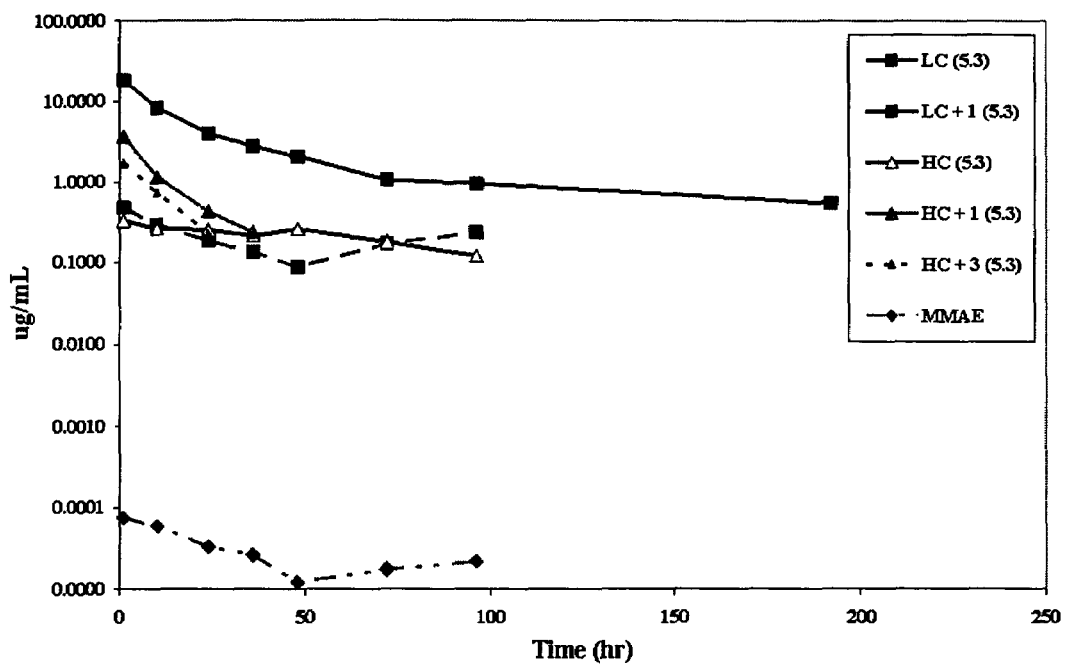
FIG. 29 shows the PK analysis of LC/MS samples from plasma from Sprague-Dawley rats dosed with trastuzumab-MC-vc-PAB-MMAE (5.3 MMAE/trastuzumab), 2 mg MMAE/kg
Figure 30:
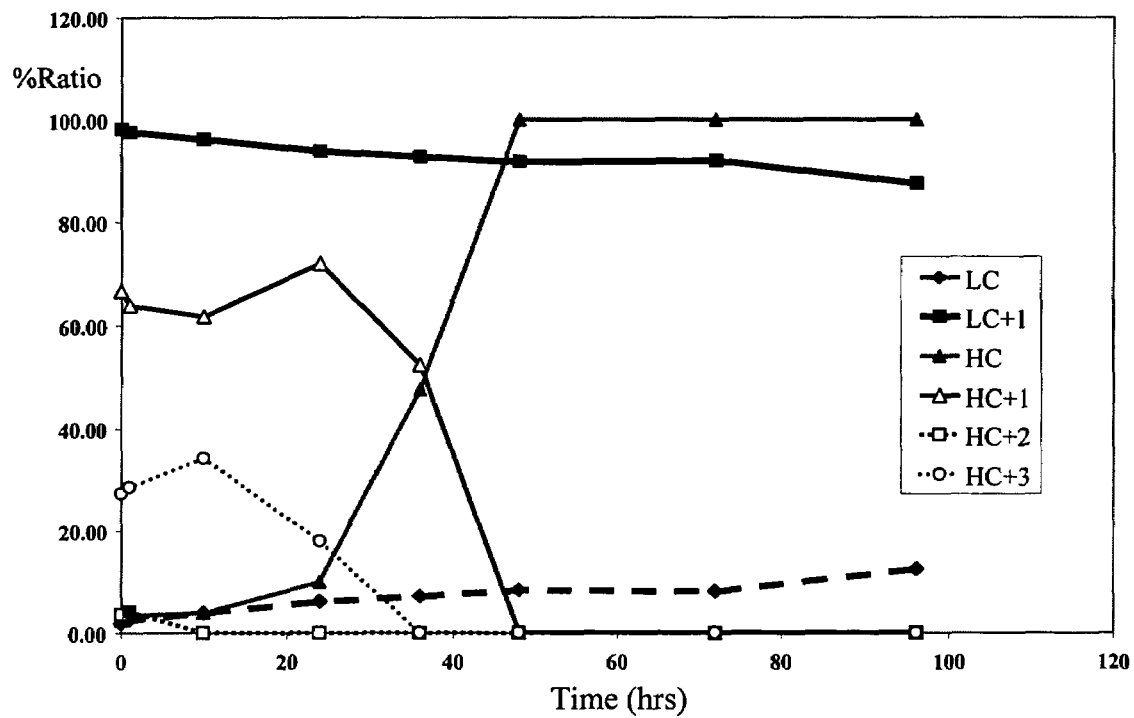
FIG. 30 shows the percent ratio plot of the level of MMAE conjugation of LC (light chain) and HC (heavy chain) fragments of trastuzumab-MC-vc-PAB-MMAE (5.3 MMAE/trastuzumab) from rat plasma.
Figure 31:
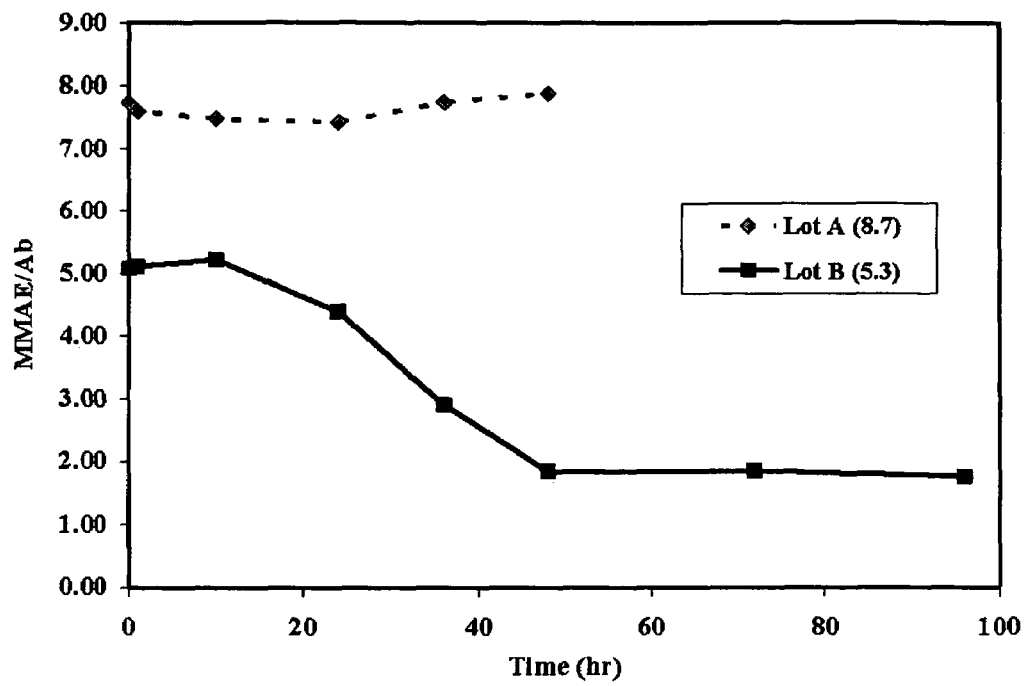
FIG. 31 shows a comparison of drug (MMAE) to antibody (trastuzumab) ratio changes over time for two preparations of trastuzumab-MC-vc-PAB-MMAE: 8.7 and 5.3 MMAE/trastuzumab) from rat plasma.

FIGS. 28-31 show the results from pharmacokinetic (PK) analysis of plasma samples by LC/MS. Sprague-Dawley rats were dosed with either of two preparations of trastuzumab-MC-vc-PAB-MMAE loaded with an average of 8.7 or 5.3 MMAE drug moieties per antibody, trastuzumab. FIGS. 28 and 29 show PK analysis of LC/MS samples from plasma from Sprague-Dawley rats dosed with: trastuzumab-MC-vc-PAB-MMAE (8.7 MMAE/trastuzumab), 2 mg MMAE/kg (FIG. 28); and trastuzumab-MC-vc-PAB-MMAE (5.3 MMAE/trastuzumab), 2 mg MMAE/kg (FIG. 29). The concentrations of the various heavy and light chains, with and without conjugated drug moieties were calculated. FIG. 30 shows the % ratio plot of the level of MMAE conjugation of LC (light chain) and HC (heavy chain) fragments of trastuzumab-MC-vc-PAB-MMAE (5.3 MMAE/trastuzumab). FIG. 31 shows a comparison of drug (MMAE) to antibody (trastuzumab) ratio changes over time for two preparations of trastuzumab-MC-vc-PAB-MMAE. One preparation had a drug to antibody ratio of 8.7 MMAE/trastuzumab, and the other was the preparation shown in FIG. 31 which had a ratio of 5.3.

Figure 32:
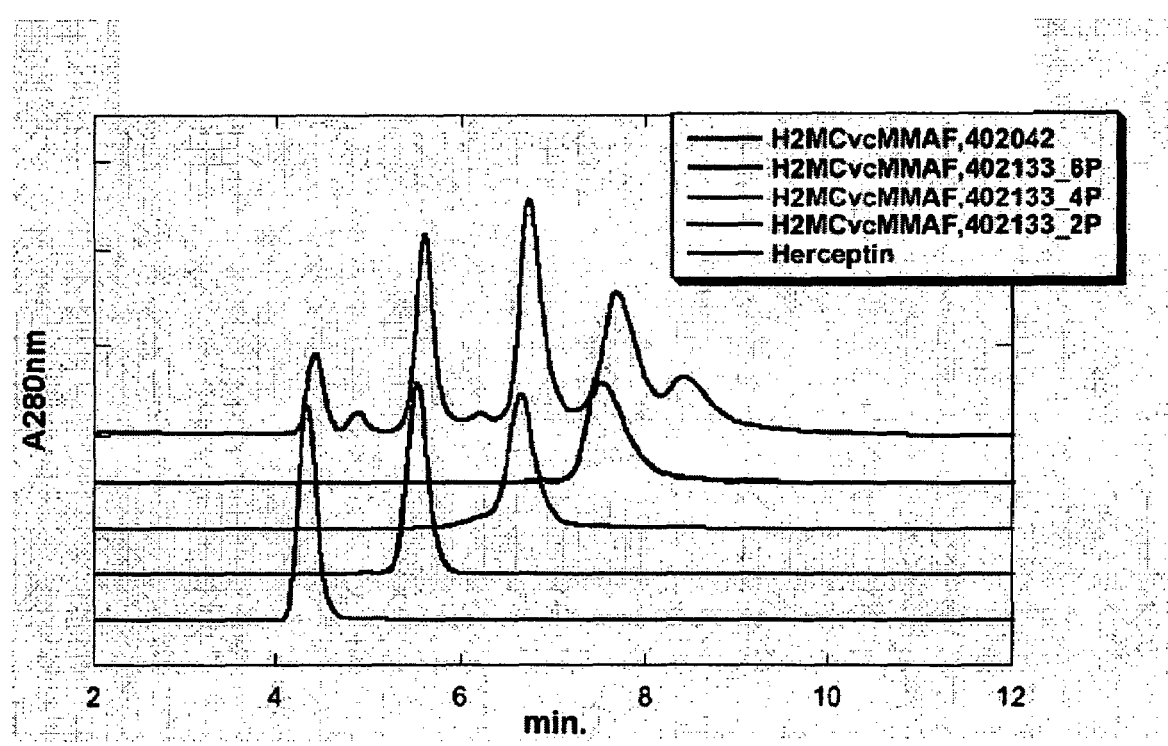
FIG. 32 shows the hydrophobic interaction chromatograms (HIC HPLC) of: (top) crude mixture of trastuzumab-MC-vc-PAB-MMAF with drug loading of 0, 2, 4, 6; (second from top) trastuzumab-MC-vc-PAB-MMAF with drug loading of 6; (middle) trastuzumab-MC-vc-PAB-MMAF with drug loading of 4; (second from bottom) trastuzumab-MC-vc-PAB-MMAF with drug loading of 2; (bottom) trastuzumab.

FIGS. 32-36 show the results of a comparison pharmacokinetic study of the drug loading effect. A single lot of antibody-drug conjugate trastuzumab-MC-vc-PAB-MMAF was prepared. Peaks from the chromatogram were identified by MS that indicated drug loadings of 2, 4, and 6 MMAF per antibody, trastuzumab (FIG. 32). FIG. 32 shows the hydrophobic interaction chromatograms (HIC) of: (top) crude mixture of trastuzumab-MC-vc-MMAF with drug loading of 0, 2, 4, 6; (second from top) ti astuzumab-MC-vc-MMAF with drug loading of 6; (middle) trastuzumab-MC-vc-MMAF with drug loading of 4; (second from bottom) trastuzumab-MC-vc-MMAF with drug loading of 2; (bottom) trastuzumab.

Figure 33:
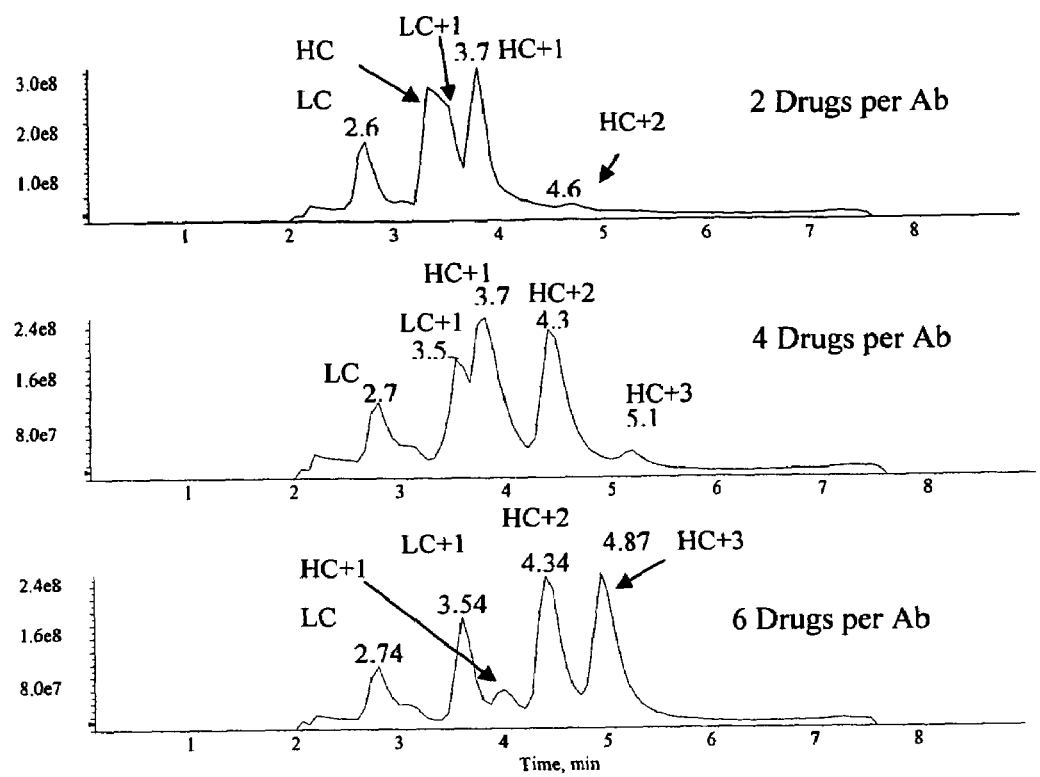
FIG. 33 shows LC/MS analysis after reduction of: (top) trastuzumab-MC-vc-PAB-MMAF with drug loading of 2; (middle) trastuzumab-MC-vc-PAB-MMAF with drug loading of 4; (bottom) trastuzumab-MC-vc-PAB-MMAF with drug loading of 6.
Figure 34:
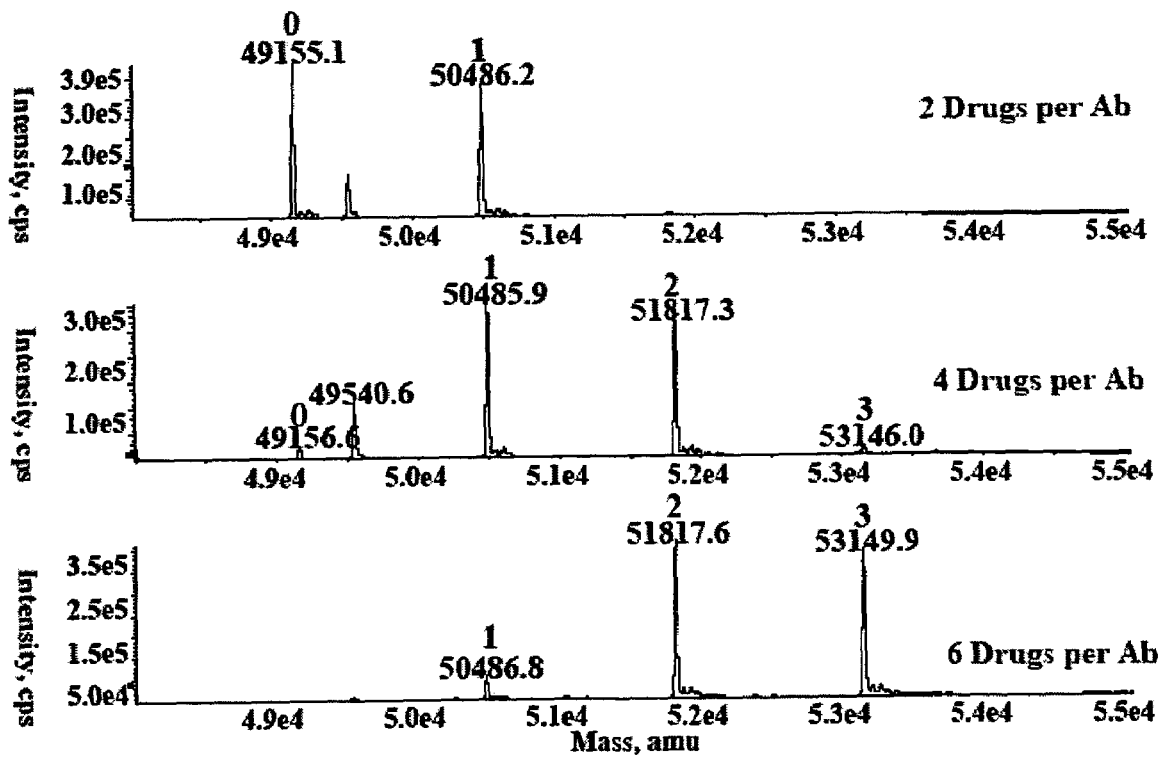
FIG. 34 shows MS analysis of the heavy chain of: (top) trastuzumab-MC-vc-PAB-MMAF with drug loading of 2; (middle) trastuzumab-MC-vc-PAB-MMAF with drug loading of 4; (bottom) trastuzumab-MC-vc-PAB-MMAF with drug loading of 6.

The components under each major peak were separated, isolated, and characterized by LC/MS. FIG. 33 shows LC/MS analysis after reduction and denaturation of: (top) trastuzumab-MC-vc-PAB-MMAF with drug loading of 2; (middle) trastuzumab-MC-vc-PAB-MMAF with drug loading of 4; (bottom) trastuzumab-MC-vc-PAB-MMAF with drug loading of 6. The sample with drug loading of 2 (top) showed 53.1% LC and 46.9% LC+1 of light chain fragments and 51% HC and 49.0% HC+1 of heavy chain fragments. Total areas for LC, LC+1, HC, and HC+1 gave a calculated total drug loading of 1.9 MMAF/Ab. The sample with drug loading of 4 (middle) showed 60.1% LC and 39.9 LC+1 of light chain fragments and 49.1% HC+1, 48.1% HC+2, 2.8% HC+3 of heavy chain fragments. Total areas for LC, LC+1, HC+1, HC+2, and HC+3 gave a calculated total drug loading of 3.9 MMAF/Ab. The sample with drug loading of 6 (bottom) showed 55.2% LC and 44.9% LC+1 of light chain fragments and 7.6% HC+1, 46.7% HC+2, 45.7% HC+3 of heavy chain fragments. Total areas for LC, LC+1, HC+1, HC+2, and HC+3 gave a calculated total drug loading of 5.5 MMAF/Ab. FIG. 34 shows MS analysis with characterization by mass of fragments with 0, 1, 2, and 3 MMAF drug moieties on the heavy chain of: (top) trastuzumab-MC-vc-PAB-MMAF with drug loading of 2; (middle) trastuzumab-MC-vc-PAB-MMAF with drug loading of 4; (bottom) trastuzumab-MC-vc-PAB-MMAF with drug loading of 6.

Free drug, MMAF, was detected in plasma from the rats dosed with trastuzumab-MC-vc-PAB-MMAF with drug loading of 2 (51.73 gm ADC/kg); trastuzumab-MC-vc-PAB-MMAF with drug loading of 4 (26.12 mg ADC/kg); and trastuzumab-MC-vc-PAB-MMAF with drug loading of 6 (17.59 mg ADC/kg). At day 5, free MMAF was 1.80 ng/ml in rats receiving trastuzumab-MC-vc-PAB-MMAF with drug loading of 2. At day 5, free MMAF was 9.09 ng/ml in rats receiving trastuzumab-MC-vc-PAB-MMAF with drug loading of 4. At day 4, free MMAF was 50.81 ng/ml in rats receiving trastuzumab-MC-vc-PAB-MMAF with drug loading of 6. The presence of free drug in plasma is consistent with the measured decrease in the drug/Ab ratio over time detected in plasma from the rats dosed with the three trastuzumab-MC-vc-PAB-MMAF conjugates with 2, 4, and 6 drug loadings (Example 9).

Figure 35:
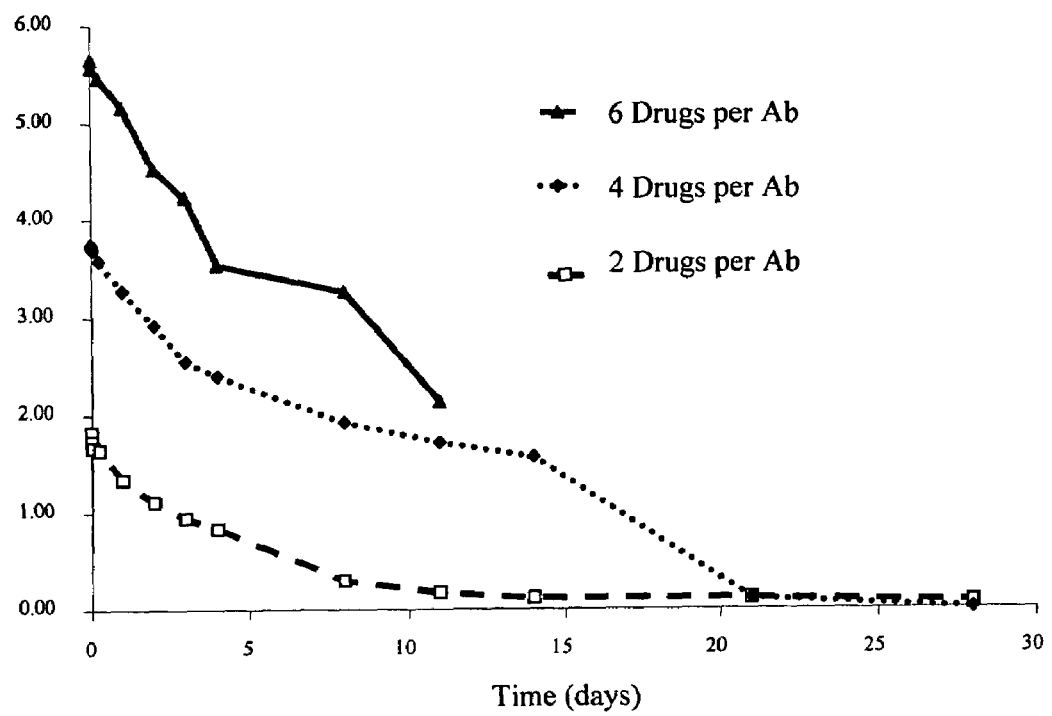
FIG. 35 shows a comparison of drug (MMAF) to antibody (trastuzumab) ratio changes over time for clearance of trastuzumab-MC-vc-PAB-MMAF with drug loading of 2; trastuzumab-MC-vc-PAB-MMAF with drug loading of 4; and trastuzumab-MC-vc-PAB-MMAF with drug loading of 6 from rat plasma samples analyzed by immunoaffinity membrane selection membrane/LC/MS.
Figure 36:
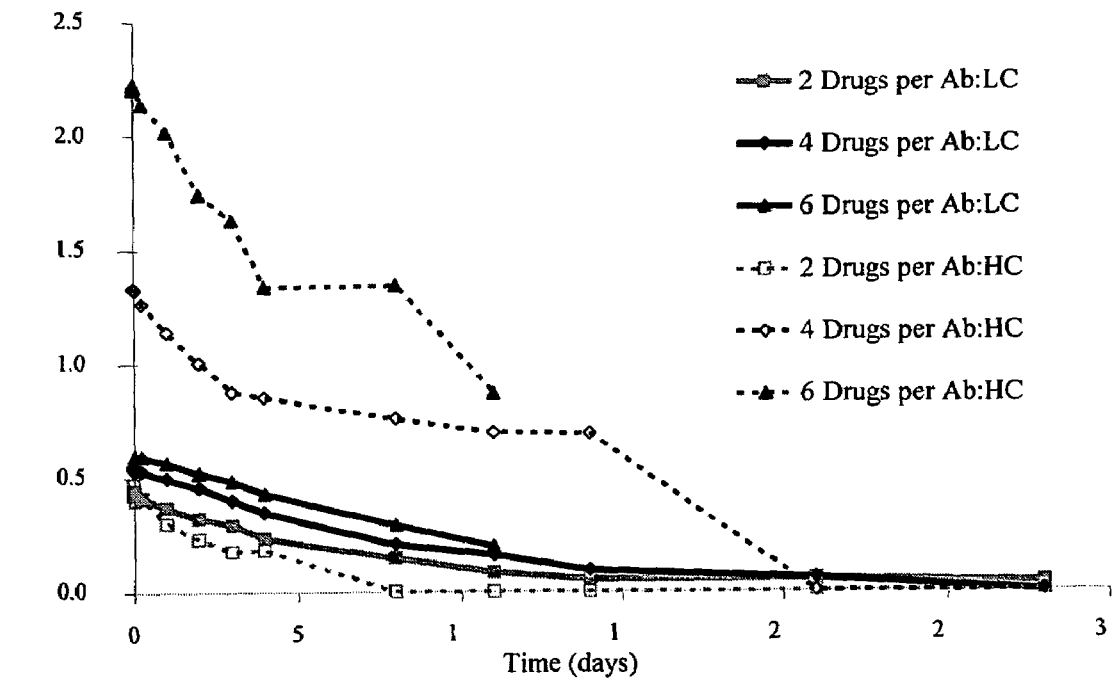
FIG. 36 shows a comparison of drug (MMAF) to LC (light chain) and drug (MMAF) to HC (heavy chain) ratio changes over time for clearance of trastuzumab-MC-vc-PAB-MMAF with drug loading of 2; trastuzumab-MC-vc-PAB-MMAF with drug loading of 4; and trastuzumab-MC-vc-PAB-MMAF with drug loading of 6 from rat plasma samples analyzed by immunoaffinity membrane selection membrane/LC/MS.

FIG. 35 shows a comparison of drug (MMAF) to antibody (trastuzumab) ratio changes over time for cleared trastuzumab-MC-vc-MMAF with drug loading of 2; trastuzumab-MC-vc-PAB-MMAF with drug loading of 4; and trastuzumab-MC-vc-PAB-MMAF with drug loading of 6 from rat plasma samples analyzed by immunoaffinity membrane selection/LC/MS (Example 2). FIG. 36 shows in further detail the changes of drug to antibody ratio by a comparison of the conjugation levels of light and heavy chain over time for trastuzumab-MC-vc-PAB-MMAF with drug loadings of 2, 4 and 6 from rat plasma samples analyzed by immunoaffinity membrane selection membrane/LC/MS.

Figure 37:
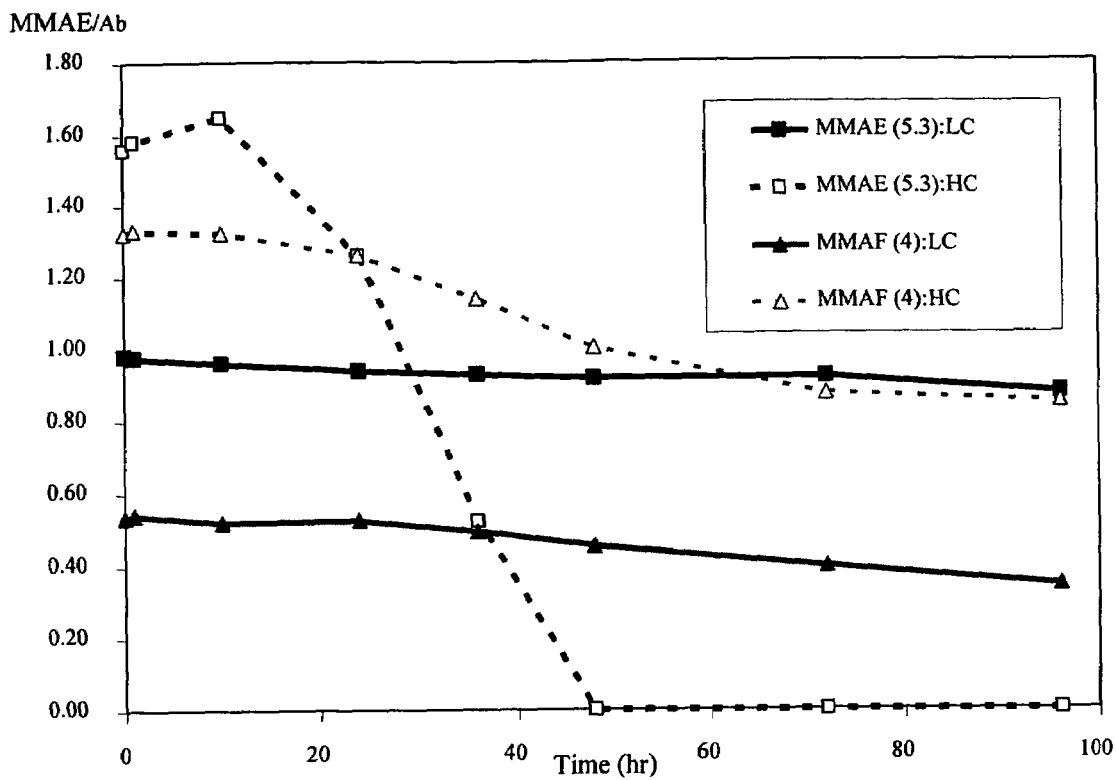
FIG. 37 shows a comparison of drug (MMAE) to LC (light chain) and drug (MMAE) to HC (heavy chain) ratio changes over time for trastuzumab-MC-vc-PAB-MMAE rat plasma samples, with average drug loading of 5.3; and trastuzumab-MC-vc-PAB-MMAF with drug loading of 4.
Figure 38:
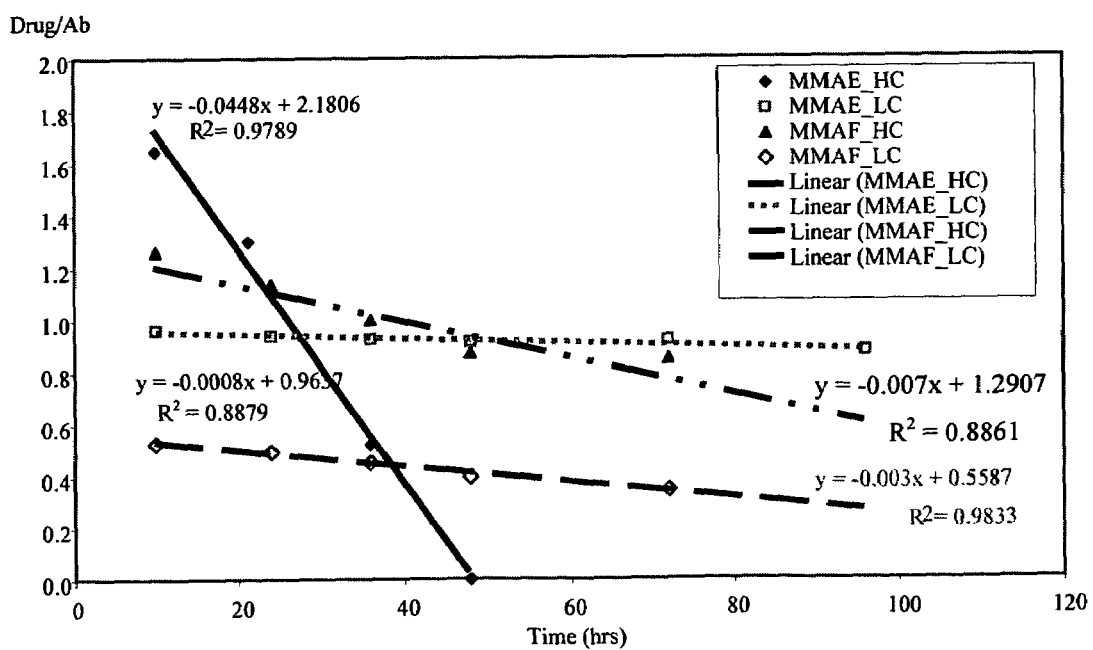
FIG. 38 shows the relative rate of drug loss from the LC (light chain) and drug (MMAE) loss from the HC (heavy chain) of trastuzumab-MC-vc-PAB-MMAE rat plasma samples, with average drug loading of 5.3; and trastuzumab-MC-vc-PAB-MMAF with drug loading of 4.

FIGS. 37 and 38 show the results of a comparison pharmacokinetic study of the differences between the drug moieties MMAE and MMAF in an antibody-drug conjugate, with similar drug loadings. Rats were dosed with Vehicle Control; 20.2 mg ADC/kg trastuzumab-MC-vc-PAB-MMAE with average drug loading of 5.3; and 26.12 mg/kg trastuzumab-MC-vc-PAB-MMAF with drug loading of 4. The dosages essentially normalize the amount of administered drug. LC/MS analysis at day 4 showed that the cleared trastuzumab-MC-vc-PAB-MMAE plasma samples showed the heavy chain fragments had essentially no drug remaining conjugated, and the light chain fragments had 0.9 MMAE per LC. LC/MS analysis at day 4 showed that the trastuzumab-MC-vc-PAB-MMAF plasma samples showed the heavy chain fragments had 0.9 MMAF per HC, and the light chain fragments had 0.4 MMAF per LC. FIG. 37 shows a comparison of the change to drug/antibody ratios over time in the drug to LC (light chain) and drug to HC (heavy chain) ratio changes over time for trastuzumab-MC-vc-PAB-MMAE with average drug loading of 5.3 and trastuzumab-MC-vc-PAB-MMAF with drug loading of 4. The graph shows that relative rates of degradation of the fragment groups are: HC-MMAE>HC-MMAF>LC-MMAF>LC-MMAE. FIG. 38 shows the relative rate of drug loss from the LC (light chain) and HC (heavy chain) of trastuzumab-MC-vc-PAB-MMAE samples with average drug loading of 5.3, and trastuzumab-MC-vc-PAB-MMAF with drug loading of 4.

Figure 40:
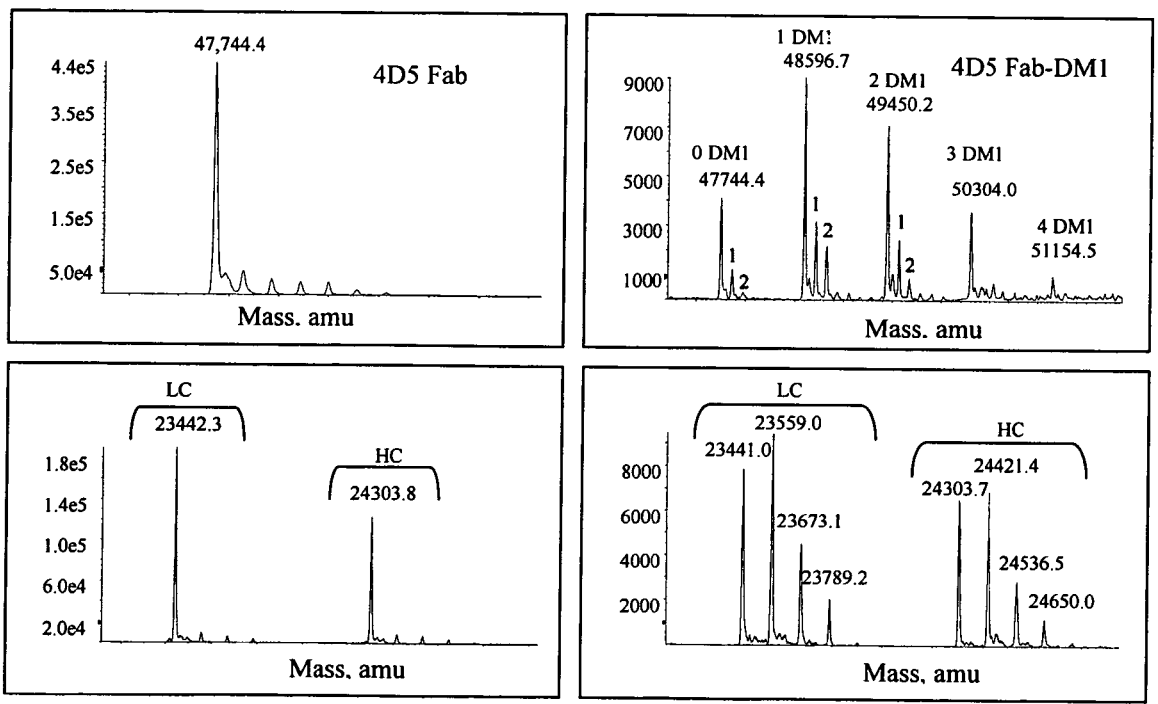
FIG. 40 shows deconvoluted mass spectrometry analysis plotting intensity in counts per second (cps) versus atomic mass units (amu) of: 4D5 Fab (top left), 4D5 reduced (bottom left), 4D5 Fab-DM1 (top right), and 4D5 Fab-DM1 reduced (bottom right).

An anti-HER2 antibody Fab, 4D5, was analyzed before and after conjugation with a maytansinoid drug moiety, DM1. FIG. 40 shows deconvoluted mass spectrometry analysis plotting intensity in counts per second (cps) versus atomic mass units (amu) of the samples. Naked 4D5 Fab (top left) shows primarily a single mass. After reduction of disulfide group, naked 4D5 separates into light chain and heavy chain (bottom left). A preparation of the antibody-drug conjugate, 4D5 Fab-SPP-DM1, shows a distribution of species, with 0, 1, 2, 3, and 4 DM1 drug moieties (top right). After reduction of antibody disulfide groups and the disulfide bond of the SPP linker, the preparation of 4D5 Fab-SPP-DM1 showed fragments that can be assigned to heavy and light chain species (bottom right), with partial linker (SP) remaining on the fragments.

Figure 42:
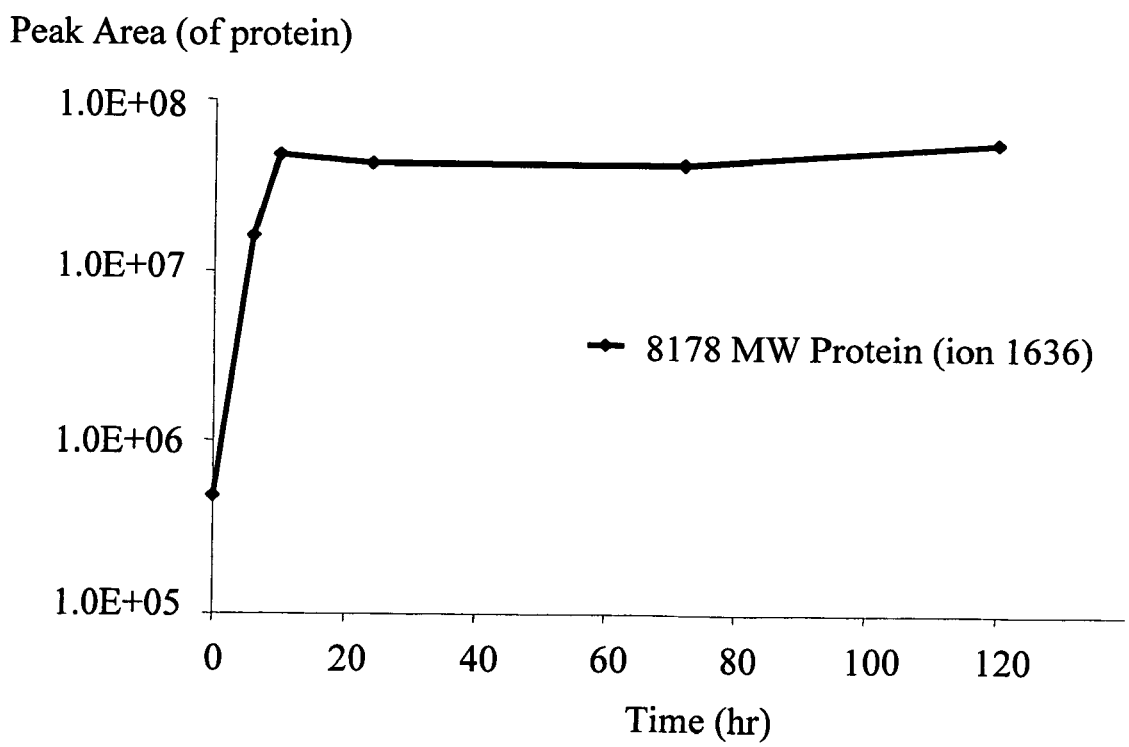
FIG. 42 shows the peak area of the 8178 mass unit (+5 ion of 1636 m/z) metabolite captured on an anti-auristatin antibody affinity membrane from in vivo plasma samples from cynomolgus monkey, collected at time points up to 120 hours after administration of trastuzumab-MC-MMAF.

Metabolites of antibody-drug conjugates can be isolated and characterized by the methods of the invention from pharmacokinetic samples. For example, FIG. 41 shows mass spectrometry analysis plotting intensity in counts per second (cps) versus atomic mass units (amu) of a metabolite of trastuzumab-MC-MMAF with a mass of about 8178 amu, captured on an anti-auristatin antibody affinity membrane from an in vivo plasma sample from cynomolgus monkey. FIG. 42 shows the peak area of the 8178 mass unit (+5 ion of 1636 m/z) metabolite captured on an anti-auristatin antibody affinity membrane from an in vivo plasma sample from cynomolgus monkey, collected at time points up to 120 hours after administration of trastuzumab-MC-MMAF.

Figure 43:
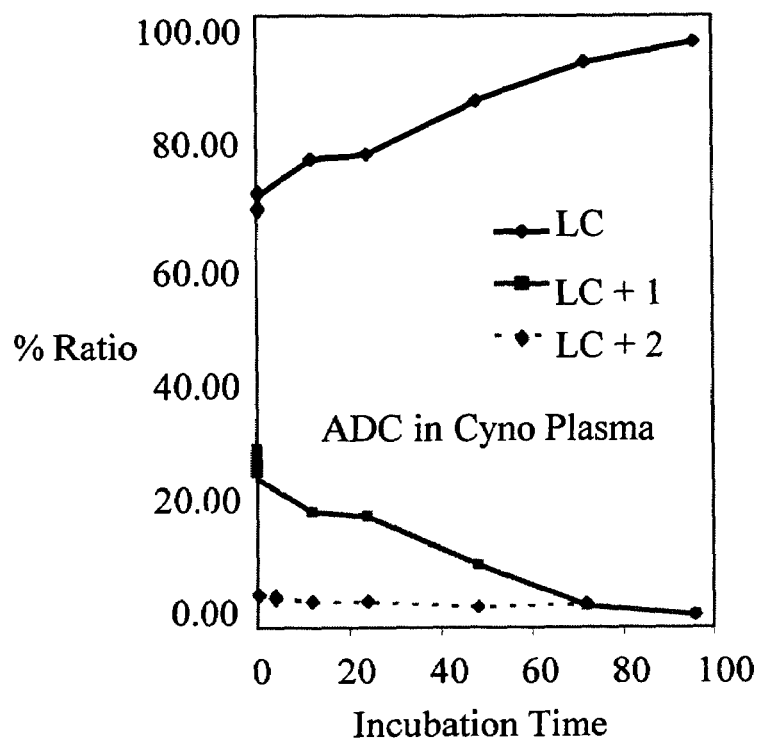
FIG. 43 shows a plot of light chain fragments detected by mass spectrometry from plasma samples collected at time points (hours) after administration of trastuzumab-SMCC-DM1 to cynomolgus monkey. The light chain fragments are characterized by their mass as conjugated to 0, 1, and 2 DM1 drug moieties, and assigned a percent ratio to total light chain fragments from trastuzumab-SMCC-DM1.

FIG. 43 shows a plot of light chain fragments detected by mass spectrometry from plasma samples collected at time points (hours) after administration of trastuzumab-SMCC-DM1 to cynomolgus monkey. The light chain fragments are characterized by their mass as conjugated to 0, 1, and 2 DM1 drug moieties, and assigned a percent ratio to total light chain fragments from trastuzumab-SMCC-DM1.

Figure 44:
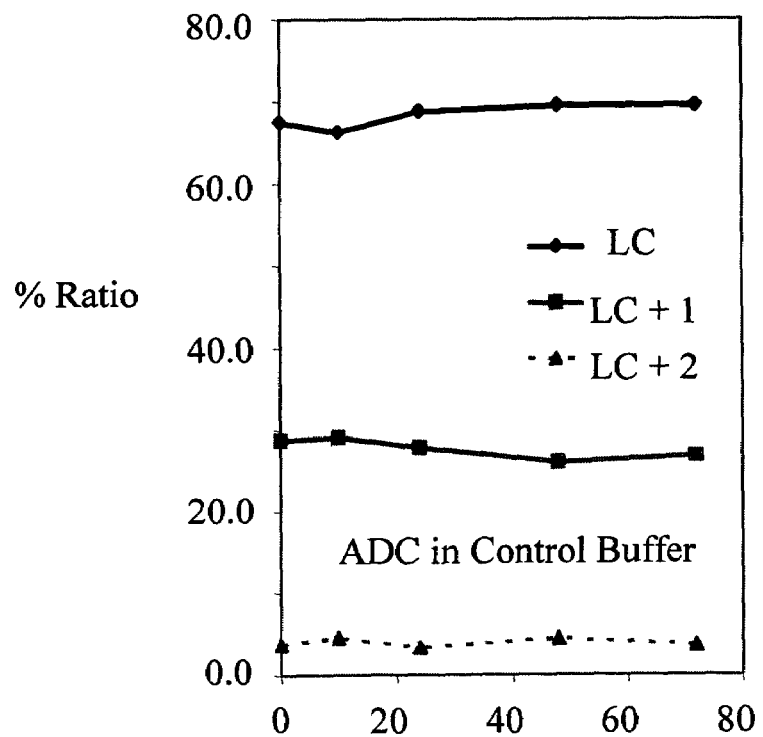
FIG. 44 shows a plot of light chain fragments detected by mass spectrometry from samples of trastuzumab-SMCC-DM1 in buffer, at incubation time points (hours). The light chain fragments are characterized by their mass as conjugated to 0, 1, and 2 DM1 drug moieties, and assigned a percent ratio to total light chain fragments from trastuzumab-SMCC-DM1.

FIG. 44 shows a plot of light chain fragments detected by mass spectrometry from samples of trastuzumab-SMCC-DM1 in buffer (PBS and 0.5% BSA), at incubation time points (hours). The light chain fragments are characterized by their mass as conjugated to 0, 1, and 2 DM1 drug moieties, and assigned a percent ratio to total light chain fragments from trastuzumab-SMCC-DM1.

Figure 45:
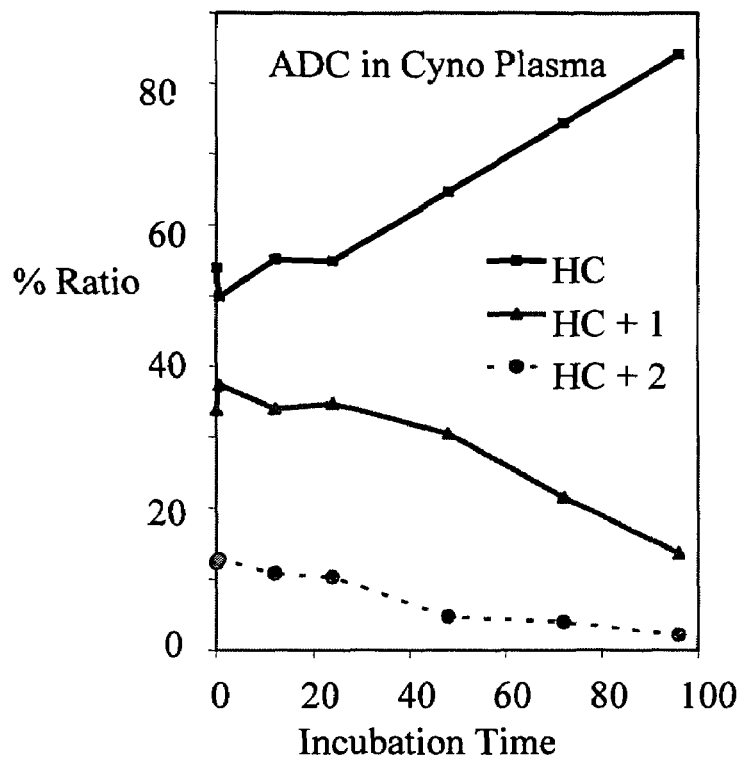
FIG. 45 shows a plot of heavy chain fragments detected by mass spectrometry from plasma samples collected at time points (hours) after administration of trastuzumab-SMCC-DM1 to cynomolgus monkey. The heavy chain fragments are characterized by their mass as conjugated to 0, 1, and 2 DM1 drug moieties, and assigned a percent ratio to total heavy chain fragments from trastuzumab-SMCC-DM1.

FIG. 45 shows a plot of heavy chain fragments detected by mass spectrometry from plasma samples collected at time points (hours) after administration of trastuzumab-SMCC-DM1 to cynomolgus monkey. The heavy chain fragments are characterized by their mass as conjugated to 0, 1, and 2 DM1 drug moieties, and assigned a percent ratio to total heavy chain fragments from trastuzumab-SMCC-DM1.

Figure 46:
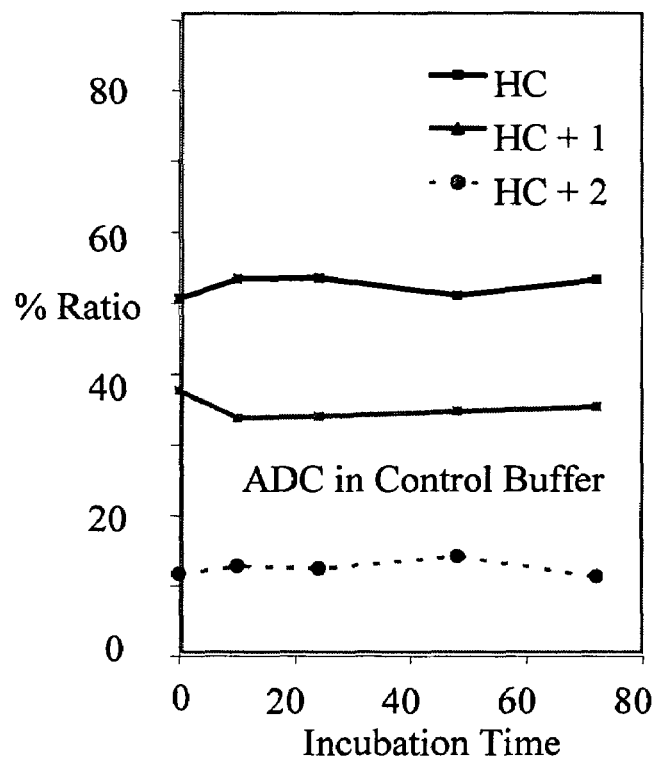
FIG. 46 shows a plot of heavy chain fragments detected by mass spectrometry from samples of trastuzumab-SMCC-DM1 in buffer, at incubation time points (hours). The heavy chain fragments are characterized by their mass as conjugated to 0, 1, and 2 DM1 drug moieties, and assigned a percent ratio to total heavy chain fragments from trastuzumab-SMCC-DM1.

FIG. 46 shows a plot of heavy chain fragments detected by mass spectrometry from samples of trastuzumab-SMCC-DM1 in buffer, at incubation time points (hours). The heavy chain fragments are characterized by their mass as conjugated to 0, 1, and 2 DM1 drug moieties, and assigned a percent ratio to total heavy chain fragments from trastuzumab-SMCC-DM1.

Figure 47:
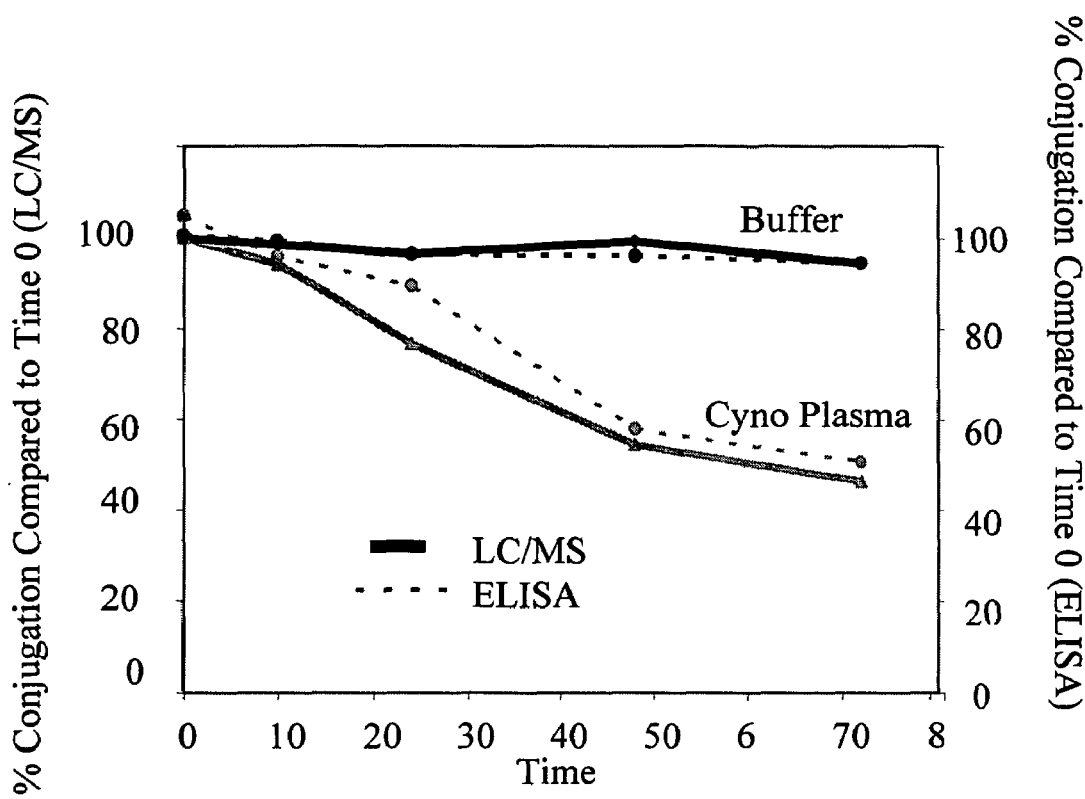
FIG. 47 shows a plot of the antibody remaining conjugated to a drug moiety in: (top lines) buffer samples of the antibody drug conjugate, trastuzumab-MC-MMAF; and (bottom lines) plasma samples collected from cynomolgus monkeys after administration of trastuzumab-MC-MMAF, at time points up to 70 hours. The fraction of antibody conjugated to a drug moiety was measured by the LC/MS method (solid lines) and by a double ELISA test (dotted lines).

FIG. 47 shows a plot of the antibody remaining conjugated to a drug moiety in: (top lines) buffer samples of the antibody drug conjugate, trastuzumab-MC-MMAF; and (bottom lines) plasma samples collected from cynomolgus monkeys after administration of trastuzumab-MC-MMAF, at time points up to 70 hours. The fraction of antibody conjugated to a drug moiety was measured by the LC/MS method (solid lines) and by a double ELISA test (dotted lines). The LC/MS and ELISA methods correlate well for both the buffer and in vivo, pharmacokinetic samples.

Figure 48:
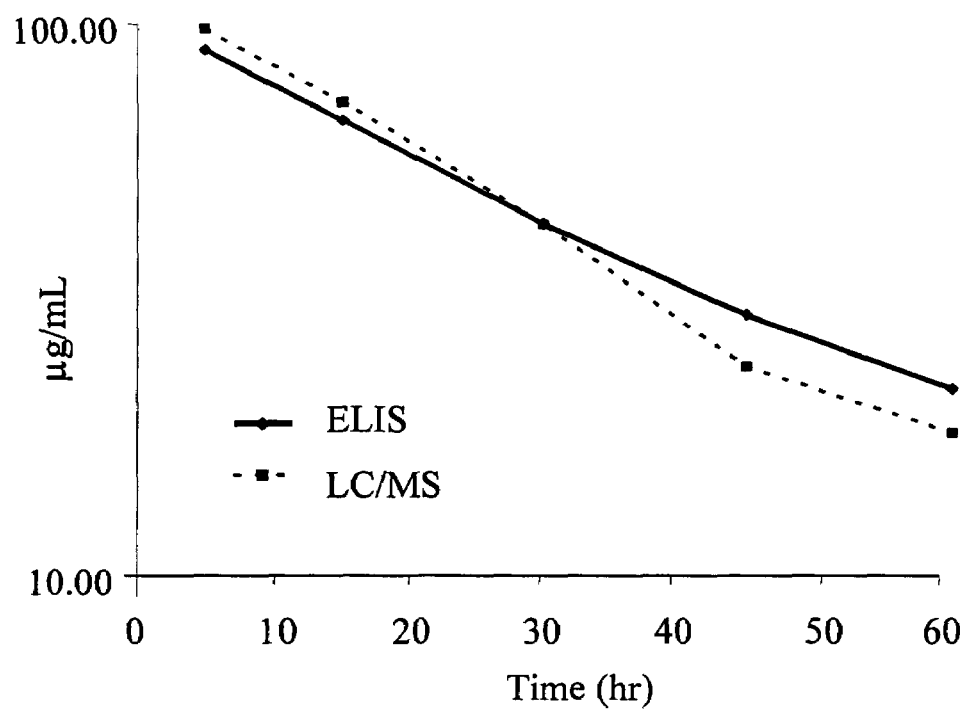
FIG. 48 shows a plot of quantitation in μg/mL of a Fab antibody drug conjugate, 4D5 Fab-MC-vc-PAB-MMAE in plasma samples collected from cynomolgus monkeys after administration of trastuzumab-MC-MMAF, at time points up to 60 hours by the LC/MS (dotted line) and ELISA test (solid line).

FIG. 48 shows a plot of quantitation in µg/mL of a Fab antibody drug conjugate, 4D5 Fab-MC-vc-PAB-MMAE in plasma samples collected from cynomolgus monkeys after administration of trastuzumab-MC-MMAF, at time points up to 60 hours by the LC/MS (dotted line) and ELISA test (solid line). A comparison of the results is provided in Table 2.

TABLE 2

| Time (hours) | ELISA total Fab (µg/mL) | LC/MS total Fab (µg/mL) | % difference between ELISA and LC/MS |
|---|---|---|---|
| 5 | 89.84 | 100.23 | 11.6 |
| 15 | 67.05 | 72.46 | 8.1 |
| 30 | 44.01 | 43.91 | −0.2 |
| 45 | 30.42 | 24.67 | −18.9 |
| 60 | 22.49 | 18.83 | −16.3 |

EXAMPLES

Samples and Reagents

HPLC grade acetonitrile was purchased from Burdick and Jackson (Muskegon, Mich.). Formic acid (FA) was purchased from Mallinckrodt (Phillipsburg, N.J.). Trifluoroacetic acid (TFA) and 1,4-dithio-DL-threitol (DTT) was purchased from Avocado Research Chemicals Ltd. (Ward Hill, Mass.). PNGaseF enzyme was purchased from Prozyme (San Leandro, Calif.). PLRP-S polymer columns were purchased from Polymer Laboratories (Amherst, Mass.).

Instrumentation

An API3000 mass spectrometer was used for the embodiments of the invention described herein and was purchased from Applied Biosystems (Foster City, Calif.). A CTC HTS-PAL autosampler was purchased from Leap Technologies (Carrboro, N.J.). Shimadzu high performance liquid chromatography (HPLC) pumps (LC-10AD) and system controller (SCL-10A) were purchased from Shimadzu Corporation (Columbia, Md.). A Keystone Scientific hot-pocket column heater was purchased from Thermo (Waltham, Mass.). A switching valve was purchased from Valco Instruments Co. Inc. (Houston, Tex.).

HPLC Method for Small Proteins

A reverse phase HPLC method was used for reduced antibody detection using a PLRP-S 8μ, 1000 Å, 2.0×50 mm cross-linked polystyrene/divinyl-benzene column. Mobile phase A and B consisted of 0.05% TFA in water and acetonitrile, respectively. The column temperature was heated to 70° C. A 9-minute gradient is used for standards and samples analysis: (0.0-1.0 min, 500 μL/min, 0% B; 1.0-1.1 min, 500-250 μl/min, 0-30% B; 1.0-1.1 min, 250 μl/min, 30% B; 1.1-1.5 min, 250 μl/min, 30% B; 1.5-5.5 min, 30-50% B; 5.5-6.5 min, 250 μl/min, 50-80% B; 6.5-7.5 min, 250 μl/min, 80% B; 7.5-7.6 min, 250 μl/min, 0% B; 7.6-9.0, 250 μl/min, 0% B). Injection volume for this method is 100-300 μl because the samples were dilute. Injection volumes for characterization may be 10-20 μl whereas injection volumes for membrane samples may be 200-500 μl. A switching valve (Valco Instruments, Co, Inc., Houston, Tex.) is used to divert sample buffers to waste (0.0-1.8 minutes). The light chain (LC), and heavy chain (HC) of the antibody elutes at approximately 4.41 and 4.76 minutes, respectively.

HPLC Method for Large Proteins

A reverse phase HPLC method was used for intact antibody detection using a PLRP-S 8μ, 4000 Å, 2.0×50 mm cross-linked polystyrene/divinyl-benzene column. Mobile phase A and B are 0.1% FA in water and acetonitrile, respectively. The column temperature was heated to 70° C. An 8-minute gradient is used for standards and samples analysis: (0.0-2.5 min, 500 μL/min, 0% B; 2.5-3.5 min, 500 μl/min, 50% B; 3.5-5.0 min, 500 μl/min, 50-% 100 B; 5.0-6.4 min, 500 μl/min, 100% B; 6.4-6.5 min, 500 μl/min, 100-0% B; 6.5-8.0, 500 μl/min, 0% B). Injection volume for this method is 10 μl. A switching valve diverts sample buffers to waste (0.0-2.5 minutes). The intact antibody elutes at approximately 3.5 minutes.

Mass Spectrometer (MS) Conditions

The Q1 scan mode (1200-2500 m/z for small protein, and 1800-3000 m/z for large proteins) was used to acquire data on the API 3000 for the full scan mode. The declustering potential (DP) was ramped from 30 to 120 or 70 to 250 volts depending on the flow rate solutions at the source. The following additional parameters were used: nebulizer gas (NEB) was 12.0, curtain gas (CUR) was 10.0, the ionspray voltage (IS) was 5500, temperature (TEM) was 300-500 depending on the column flow rate, focusing potential (FP) was 400V, entrance potential was 10.0V, and the deflector (DF) was −100V. Single ion monitoring (SIM) methods of the reduced antibody used a DP voltage of 75 V.

Example 1

Immunoaffinity Chromatography and Reverse Phase HPLC Column Switching Method

A column switching, immunoaffinity/LC/MS method was used for analysis of ADC and quantitating the small molecule drug moiety and metabolites. A PROSPEKT-2® instrument (Chromatographic Specialties, Inc., Brockville, Ontario) was used for automated column washing and switching prior to introduction into the mass spectrometer. The immunoaffinity/LC/MS method. The immunoaffinity/LC/MS method performs affinity isolation of the antibody conjugate, online SPE extraction of the free drug, reverse phase separation of the small molecule, followed by reversed phase separation of the conjugated antibody. The waste stream from the immunoaffinity column (which contains the free drug) is directed through the C18 SPE cartridge before it is discarded. The SPE cartridge is eluted while the plasma is washed from the affinity column and finally the affinity column is eluted. Two data files are generated from one plasma injection and provide valuable quantitation data for the conjugated antibody species in vivo.

The LC/MS/MS method employs the PROSPEKT-2 instrument for online SPE (solid phase extraction), reverse phase chromatography (SYNERGI C12) for chromatographic separation, and an API 3000 mass spectrometer for detection. The small molecule method had a range of 0.3 to 750 ng/ml for the MMAE and MMAF auristatin drugs. Linear curves in plasma were obtained, $R^2=0.999$ (Kadkhodayan, M. and Mann, E. "New Strategies in Characterization and Quantitation of Antibody-targeted Drug Conjugates in Plasma using LC/LC/MS", 51st Conference on Mass Spectrometry and Allied Topics, American Society for Mass Spectrometry, Montréal, Québec, Jun. 8-12, 2003). Additionally, the antibody portion of the method had a range of 0.14 to 300 μg/mL and was linear ($R^2=0.999$) in both solution and plasma.

Example 2

Immunoaffinity Membrane Selection and Reverst Phase HPLC Method

An immunoaffinity membrane (IAM) selection and reverse phase HPLC method was developed to characterize and quantitate biological samples (Mann, E. and Kadkhodayan, M. "Antibody Isolation and Quantitation using LC/MS and a Novel 96-Well Immunoaffinity Membrane", 52nd Conference on Mass Spectrometry and Allied Topics, American Society for Mass Spectrometry, Nashville, Tenn., May 23-27, 2004). A commercially available affinity membrane was used in a 96-well format, which allows simultaneous cleanup of 96 samples. A vacuum manifold equipped with a pressure gauge (Aldrich) was used for membrane loading, washes and elution. The pressure gauge was kept at 20 psi for all washes and at 5 psi for the critical steps, such as immobilization of the antigen, application of plasma samples and protein elution. Biological samples such as plasma were delivered to each well, incubated, washed, and eluted from the membrane with 0.2% trifluoroacetic acid (TFA) into a 2-ml square well 96-well plate which was directly placed into the autosampler for sample analysis by LC/MS.

An API 3000 triple quadrapole mass spectrometer equipped with a reversed phase column (PLRP-S, 2.0×50 mm, 8 u, 1000 Å) was used for LC/MS sample analysis. An 8-min HPLC gradient using acetonitrile and water with 0.05% TFA was utilized.

Antigen immobilization and antibody capture conditions were evaluated and adjusted (buffer choice, concentration, and pH). The immobilization chemistry involving stable bond formation between azolactone functional groups on the EMPORE membrane and amine groups on the antibody antigen (Ab) is below. For capture of trastuzumab, an extracellular domain (ECD) fragment of anti-HER2, human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens et al (1985) Science 230:1132-9; Slamon, et al (1989) Science 244:707-12). The number and sequence of washes (PBS, dilute tween20 detergent, and Millipore™ water) were optimized to determine the most efficient cleanup strategy. The optimal elution volume needs to be optimized for each antigen-antibody system. The EMPORE membranes are normally reusable, e.g. up to 30 times without adverse effects.

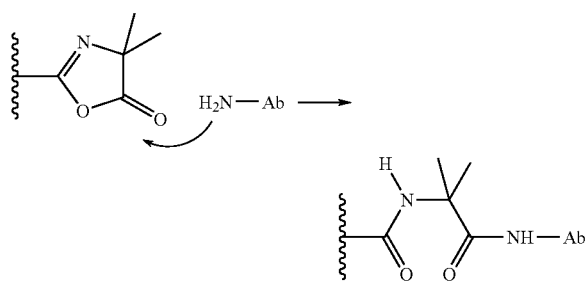

An azalactone affinity membrane was prepared utilizing the optimized conditions and tested for linearity and whole plate variability. The antibody calibration curve from antibodies recovered from this membrane demonstrated great linearity ($R^2$=0.9993) for a range of 75 μg/ml to 0.14 μg/ml (FIG. 10). The whole plate variability experiment resulted in 6.0% CV for the entire plate and 2.5 to 8.0% CV for the following rows and columns representing the 96 wells (8×12) in FIG. 11. The area under the curve counts thus show acceptable precision across the entire plate.

Certain antibodies are glycosylated with one or more sugar residues. The monoclonal antibody analyzed in FIG. 12 shows spectra of the glycosylated antibody before (top) and after deglycosylation (bottom). Heterogeneity of the charged ions is greatly diminished by sugar removal resulting in greater accuracy and sensitivity. On-membrane enzymatic reactions can be conducted, such as deglycosylation using PNGaseF (FIG. 12).

Affinity Membrane Immobilization Procedure

1) Preparation of Antigen Compound for Immobilization. An antigen or antibody appropriate for capture of the analyte of interest is selected and, the protein should be exchanged into a high salt solution of either (1M sodium sulfate & 0.1M sodium phosphate pH=7.5) or (1M ammonium citrate & 0.1 M sodium phosphate pH=7.5), prior to immobilization. The reaction efficiency with the azlactone affinity membrane may increase with higher pH (up to pH=9). However since proteins are unstable at high pH levels, a pH of 7.5 to 8.0 may be an optimal compromise between reactivity and stability. NAP 5, 10 or 25 columns (Pharmacia) are used to buffer exchange the samples. The protein should also be kept at the highest concentration possible for the best reaction conditions.

2) Immobilization of the antigen/antibody to 3M Empore™ Affinity 96-Well plate. The affinity membrane should stay in the sealed container right up until the addition of the protein. A typical target amount of protein is 100 μg per well (although more or less may be added based on intended use). The volume of high salt protein solution (step 1) needed per well is calculated with a minimum volume of 80 μL. The package containing the affinity membrane is opened and 100 μg protein per well is added. The membrane is incubated at 37° C. for two hours. Within the first 5 minutes following addition of the solution, the membranes may visibly swell.

3) Quenching the 3M Empore™ Affinity Membrane. The protein solution should be pulled though the membrane with a light vacuum (−10 mm Hg). Ethanolamine is used for quenching the unreacted azlactone sites on the membrane. About 500 μL 3 M ethanolamine is added to adjust to pH 8 and pulled through the membrane using a vacuum manifold. Another 500 μL 3 M ethanolamine pH=8 is added and the membrane is incubated for one hour at 37° C. The ethanolamine is drawn by vacuum through the membrane and each well is washed with 500 μL PBS (phosphate buffered saline).

4) Blocking of Non-Specific Binding Sites. About 1 mL of 0.5% bovine serum albumin (BSA) was added to each well of the affinity membrane. This was allowed to incubate for 15 minutes at room temperature. The BSA solution was pulled though each well by vacuum and then washed additionally with 1 mL PBS. The membrane is now ready for use. The membrane is stored in solution covered at 4° C. with 200 μL 0.02% sodium azide in PBS per well. Additional PBS is added if necessary to prevent the wells from drying out.

Affinity Membrane Procedure for Use

1) Target Capture on the 3M Empore™ Affinity 96-Well Membrane. A prepared immunoaffinity membrane with immobilized antigen/antibody is used for capturing a target protein or antibody in plasma. Target protein/antibody in solution can be captured using the membrane, however non-specific binding to the wells can be an issue. Wash each well with 1 mL PBS (phosphate buffered saline) prior to use. Add 100 μL of neat plasma or serum containing the target protein/antibody to the membrane. Incubate the membrane at 37° C. for 30 minutes. Pull the sample through the membrane with a gentle vacuum (−10 mmHg).

2) Wash/Dealycosylate the Captured Target. Each well should be washed with the following consecutive 1-mL washes: once with PBS, once with PBS+1.6% Tween 20, and three times with water. If deglycosylation of the captured compound is desired, add 100-μL deglycosylation solution to each well of the membrane and incubate on the membrane for 2 days at 37° C. Wash each well twice with 1 mL of water following an on membrane deglycosylation reaction. (Deglycosylation Solution=110 μL N-Glycanase enzyme (*Prozyme*)+8140 μL water+2750 μL 80 mM sodium phosphate pH=7.5)

3) Target Elution. Each antibody-antigen pair has a unique elution volume based on the affinity.

Experimentally determine the required elution volume for your compounds prior to use. Treat a 2-mL square well deep well 96-well plate with 3M Empore blocking buffer by adding 2-mL to each well, incubate the plate for 15 minutes at 37° C., rinse the plate five times with water and dry the plate. This coats the plate to prevent sticking of the target. This coating can only be used in aqueous solutions, as it will dissolve in organic solvents. Elute the target using high pH (typical is 300-500 μL of 0.2% TFA) into the blocked 96-well plate with a gentle vacuum. The eluted target is ready for analysis.

4) Sample Reduction. If sample reduction is required, add 8 μL of reducing solution to sample in the 96-well plate. Gently mix with a pipet. Incubate the covered 96-well plate for 1 hour at 37° C. (Reducing Solution=900 μL 5 M ammonium acetate and 100-μL of 1M tris-(2-carboxy-ethyl)-phosphine hydrochloride (TCEP))

Example 3

Nanomate ESI Chip Method

An automated nanoelectrospray chip method for mass spectrometry analysis of antibody-drug conjugate plasma samples was developed (Kadkhodayan, M. and Mann, E. "Rapid Antibody Characterization and Quantitation using Automated Chip-based Nanoelectrospray/MS", 52nd Conference on Mass Spectrometry and Allied Topics, American Society for Mass Spectrometry, Nashville, Tenn., May 23-27, 2004).

An API 3000 equipped with NANOMATE 100 and the ESI CHIP was used. The NANOMATE 100 instrument system is a commercially available nanospray interface that utilizes an ESI chip containing 100 individual nozzles for automated nanospray infusion into the mass spectrometer, resulting in a low and controlled flow rate with higher sensitivity (lower LOQ), reduced sample consumption, automation, and elimination of sample carryover benefits. The sample is aspirated through conductive pipette tips and delivered to the back of a nozzle on the chip. High voltage is applied to the pipette, forming a 100 nl/min electrospray plume. The NANOMATE settings were 5-mL sample aspiration followed by a 3-mL air-gap to provide 0.2 minutes of baseline prior to the sample peak. Gas pressure used was 0.4 psi and the applied voltage for nanospray was 1.6 kV in the positive mode. One-minute infusion time was found to have optimum S/N (signal to noise) ratio.

Two different solvent systems were employed for separations of intact and reduced antibodies, respectively, with the NANOMATE® (Advion BioSciences, Inc., Ithaca, N.Y.) ESI chip method. The reduction procedure involved using Tris (2-carboxyethyl)-phosphine hydrochloride as the reducing agent, and N-ethylmaleimide as the alkylating agent. All samples were solvent exchanged using NAP 5 columns. The final composition was 2.5 mM ammonium acetate in 50% acetonitrile with 0.1% formic acid.

Ionization conditions for the intact and reduced antibodies were optimized by investigating various parameters such as acid percentage, ion pair agent concentration and organic solvent choice. The DP voltage was an important parameter in obtaining high quality data. Using the optimized conditions, characterization of various antibodies revealed information about carbohydrate distribution.

Calibration curves obtained by nanoelectrospray flow rates (100 n/min) showed a 40-fold increase in sensitivity when compared to conventional LC/MS flow rates (300 μl/min) with % CV's ranging from 5 to 15%. The linear range of this method was 4 to 300 pg/μl with absolute sensitivity of 400 femtograms (2.7 attomoles) using a 1-minute infusion time.

Example 4

Preparation of Trastuzumab-MC-MMAE by Conjugation of Trastuzumab and MC-MMAE

Trastuzumab, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, maleimidocaproyl-monomethyl auristatin E (MMAE), i.e. MC-MMAE, dissolved in DMSO, is diluted in acetonitrile and water at known concentration, and added to the chilled reduced antibody trastuzumab in PBS. After about one hour, an excess of maleimide is added to quench the reaction and cap any unreacted antibody thiol groups. The reaction mixture is concentrated by centrifugal ultrafiltration and trastuzumab-MC-MMAE is purified and desalted by elution through G25 resin in PBS, filtered through 0.2 μm filters under sterile conditions, and frozen for storage.

Example 5

Preparation of Trastuzumab-MC-MMAF by Conjugation of Trastuzumab and MC-MMAF

Trastuzumab-MC-MMAF was prepared by conjugation of trastuzumab and MC-MMAF following the procedure of Example 4.

Example 6

Preparation of Trastuzumab-MC-val-sit-PAB-MMAE by Conjugation of Trastuzumab and MC-val-cit-PAB-MMAE Trastuzumab-MC-val-cit-PAB-MMAE was prepared by conjugation of trastuzumab and MC-val-cit-PAB-MMAE following the procedure of Example 4.

Example 7

Preparation of Trastuzumab MC-val-cit-PAB-MMAF by Conjugation of Trastuzumab and MC-val-cit-PAB-MMAF Trastuzumab-MC-val-cit-PAB-MMAF was prepared by conjugation of trastuzumab and MC-val-cit-PAB-MMAF ("Monomethylvaline Compounds Capable of Conjugation to Ligands", U.S. Ser. No. 10/983,340, filed Nov. 5, 2004) and following the procedure of Example 4.

Example 8

Pharmacokinetic Study of Trastuzumab-MC-val-cit-PAB-MMAE in Rats

Forty two female Sprague-Dawley rats (75-80 grams each) were each administered with Vehicle (Group 1), the antibody-drug conjugate trastuzumab-MC-vc-PAB-MMAE (Groups 2-6), or free drug, monomethylvaline auristatin, MMAE (Group 7). Groups 2 and 3 were administered a preparation of Tr-MC-val-cit-PAB-MMAE with average drug loading of 8.7 MMAE/Tr. Groups 4, 5, and 6 were administered a preparation of Tr-MC-val-cit-PAB-MMAE with average drug loading of 5.3 MMAE/Tr. Dosages of ADC were adjusted to deliver comparable exposure to drug moiety, i.e. Groups 2 and 4 (840 μg MMAE/m$^2$), and Groups 3 and 5 (2105 μg MMAE/m$^2$). Group 6 received the highest dose of 4209 μg MMAE/m$^2$.

| Group | Sample Administered | mg ADC/kg | μg MMAE/m²* | MMAE/Tr | N/sex |
|---|---|---|---|---|---|
| 1 | Vehicle (PBS) | 0 | 0 | 0 | 6/F |
| 2 | Tr-MC-val-cit-PAB-MMAE | 5.0 | 841 | 8.7 | 6/F |
| 3 | Tr-MC-val-cit-PAB-MMAE | 12.5 | 2103 | 8.7 | 6/F |
| 4 | Tr-MC-val-cit-PAB-MMAE | 8.06 | 840 | 5.3 | 6/F |
| 5 | Tr-MC-val-cit-PAB-MMAE | 20.2 | 2105 | 5.3 | 6/F |
| 6 | Tr-MC-val-cit-PAB-MMAE | 40.4 | 4209 | 5.3 | 6/F |
| 7 | Free MMAE | 0.206 | 840 | NA | 6/F |

*Body surface area calculated using MW 718 MMAE and MW 145167 trastuzumab, and as follows: [{(body weight in grams to 0.667 power) × 11.8}/10000]

The dose solutions were administered by a single intravenous bolus tail-vein injection on Study Day 1 at a dose volume of 10 ml/kg. All dose solutions were within 10% of the intended concentration. Body weights of the animals were measured pre-dose on Study Day 1 and daily thereafter. Whole blood was collected into EDTA containing tubes for hematology parameters and complete blood counts. Whole blood was collected into serum separator tubes for clinical chemistry parameters. Blood samples were collected pre-dose on Study Day 4, and on Study Days 3 and 5. Whole blood was also collected into lithium heparin containing tubes and the plasma was frozen at −70° C. for later analysis.

All animals in dose groups 1, 2, 3, 4, 5, and 7 appeared healthy throughout the 5 days on study. Two animals in Group 6 administered 40.4 mg/kg trastuzumab-MC-val-cit-PAB-MMAE (5.3, cysteine) were found dead on Study Day 4. The remaining 4 animals in that group were moribund (lethargy and yellow discharges in the urogenital area) and were euthanized and necropsied on Day 4. Animals in groups 2, 4, and 7 were administered comparable amounts of MMAE (840 ug/m²) and had comparable changes in body weight. Animals administered higher amounts of MMAE (2105 ug/m²) in dose group 3 administered 12.5 mg/kg trastuzumab-MC-val-cit-PAB-MMAE (8.7 drugs/antibody) and dose group 5 administered 20.2 mg/kg trastuzumab-MC-val-cit-PAB-MMAE (5.3 drugs/antibody) however did have significantly different changes in body weight by Day 5 ($p<0.05$).

Example 9
Pharmacokinetic Study of
Trastuzumab-MC-val-cit-PAB-MMAF in Rats

Sprague-Dawley rats (75-80 grams each) were each administered with an HPLC isolated form of the antibody-drug conjugate trastuzumab-MC-vc-PAB-MMAF (Groups 1, 2, 3), or naked, unconjugated antibody trastuzumab (Group 4). Group 1 rats received the HPLC purified, 2 drug/Ab conjugate. Group 1 rats received the HPLC purified, 4 drug/Ab conjugate. Group 1 rats received the HPLC purified, 6 drug/Ab conjugate. Each rat received a single bolus injection at time 0.

| Group | Sample Administered | mg ADC/kg | MMAF/Tr | N |
|---|---|---|---|---|
| 1 | Tr-MC-val-cit-PAB-MMAF | 2.0 | 2 | 4 |
| 2 | Tr-MC-val-cit-PAB-MMAF | 2.0 | 4 | 4 |
| 3 | Tr-MC-val-cit-PAB-MMAF | 2.0 | 6 | 4 |
| 4 | Tr (trastuzumab, rhu4D5) | 2.0 | 0 | 4 |

Blood (0.2 mL) was collected at the following timepoints: Groups 1-4: 0, 3-min 1, 6 and 24 hrs and 2, 3, 4, 8, 11, 14, 21, 28 days post-dose. Plasma samples were analyzed by the immunoaffinity membrane selection and reverse phase HPLC method of Example 2. The pharmacokinetic results are plotted in FIGS. 35 and 36.

Example 10

Cymomolgus Monkey Toxicity/Safety

Similar to the rat pharmacokinetic studies, cynomolgus monkeys were treated with ADC followed by analysis of plasma samples, as well as liver enzyme measurements, and inspection and analysis of the effects on various organs. Gross observations included changes in body weights and signs of lesions and bleeding. Clinical pathology parameters (serum chemistry and hematology), histopathology, and necropsy were conducted on dosed animals.

We claim:

1. A method for detecting an antibody-drug conjugate comprising:
   (i) separating the antibody-drug conjugate from a sample matrix by affinity separation wherein the antibody-drug conjugate comprises a monomethyl auristatin drug and a thio-ether linkage and wherein the thio-ether linkage is formed by reducing the interchain disulfide bonds of the antibody and conjugating the monomethyl auristatin drug to a cysteine thiol group of the reduced antibody, and wherein the antibody of the antibody-drug conjugate is an immunoreactive protein having an immunoglobulin structure;
   (ii) eluting the separated antibody-drug conjugate; and
   (iii) detecting the separated and eluted antibody-drug conjugate by electrospray, selective ion monitoring mass spectrometry.

2. The method of claim 1 wherein the antibody-drug conjugate is separated from the sample by immunoaffinity separation and reverse phase liquid chromatography.

3. The method of claim 1 wherein the sample matrix is plasma.

* * * * *